(12) United States Patent
Juncker et al.

(10) Patent No.: US 8,838,462 B2
(45) Date of Patent: Sep. 16, 2014

(54) SYSTEMS AND METHODS FOR ANALYZING WORKFLOW ASSOCIATED WITH A PATHOLOGY LABORATORY

(75) Inventors: Flemming Juncker, Vallensbaek (DK); Mats Grahn, Ystad (SE); Nihad Hasagic, Wermatswil (CH)

(73) Assignee: Dako Denmark A/S (DK)

( * ) Notice: Subject to any disclaimer, the term of this patent is extended or adjusted under 35 U.S.C. 154(b) by 844 days.

(21) Appl. No.: 12/468,943

(22) Filed: May 20, 2009

(65) Prior Publication Data

US 2009/0316977 A1    Dec. 24, 2009

Related U.S. Application Data

(60) Provisional application No. 61/071,852, filed on May 21, 2008.

(51) Int. Cl.
  *G06K 9/00*  (2006.01)
  *G06F 19/00*  (2011.01)

(52) U.S. Cl.
  CPC .................................. *G06F 19/366* (2013.01)
  USPC ................. 705/2; 382/133; 422/63; 422/537; 705/3

(58) Field of Classification Search
  USPC ................... 422/63, 537; 435/286.4; 705/2, 3
  See application file for complete search history.

(56) References Cited

U.S. PATENT DOCUMENTS

| | | | |
|---|---|---|---|
| 7,517,698 B2 * | 4/2009 | Dussauze et al. | 436/178 |
| 7,691,326 B2 * | 4/2010 | Sorenson et al. | 422/537 |
| 7,850,912 B2 * | 12/2010 | Favuzzi et al. | 422/63 |
| 2006/0148063 A1 * | 7/2006 | Fauzzi et al. | 435/286.4 |
| 2008/0103720 A1 * | 5/2008 | White et al. | 702/127 |
| 2008/0235055 A1 * | 9/2008 | Mattingly et al. | 705/3 |
| 2008/0243394 A1 * | 10/2008 | Petricoin et al. | 702/19 |
| 2009/0178004 A1 * | 7/2009 | Stoval et al. | 715/812 |

* cited by examiner

*Primary Examiner* — Hiep V Nguyen
*Assistant Examiner* — Teresa Woods
(74) *Attorney, Agent, or Firm* — Finnegan, Henderson, Farabow, Garrett & Dunner LLP.

(57) ABSTRACT

A computer system for analyzing a specimen processing workflow in a pathology laboratory including a display and a processor configured to provide a first interface, a second interface, and a third interface to the display, receive, via the first interface, a first set of parameters associated with an existing specimen processing workflow in a pathology laboratory, the first set of parameters including a workflow process and a workflow scale, and determine, based on the first set of parameters, current performance data of the existing specimen processing workflow having an associated current cost information and current time utilization. The processor may further be configured to receive, via the second interface, a second set of parameters associated with a proposed modification to the existing specimen processing workflow, the second set of parameters including parameters associated with at least one laboratory device, determine, based on the first and second sets of parameters, revised performance data having an associated revised cost information and revised time utilization, and provide an output comprising a comparison between revised performance data and the current performance data.

14 Claims, 44 Drawing Sheets

SYSTEMS AND METHODS FOR ANALYZING WORKFLOW ASSOCIATED WITH A PATHOLOGY LABORATORY

RELATED APPLICATIONS

This application claims the benefit of priority from U.S. Provisional Application No. 61/071,852 filed on May 21, 2008, the entire contents of which are incorporated herein by reference.

FIELD OF THE INVENTION

The present disclosure relates to pathology laboratory workflow and, more particularly, to systems for analyzing economic and performance-related workflow data and making workflow modifications in a pathology laboratory.

BACKGROUND OF THE INVENTION

Advances in analytical science have made it possible to extract a wide variety of information from a biological specimen. For example, it may be possible to assess the health, identify possible future health issues, and provide information related to the genetic makeup of an individual from which the specimen was obtained.

Many of these biological specimens may be processed in laboratories. The laboratory may receive such specimens from institutions, including, for example, hospitals, clinics, and/or the police, and also, to a lesser extent, from individuals themselves. These specimens may include, for example, tissue removed during a surgical procedure, tissue from crime scenes, and test materials from a home testing kit (e.g., an HIV test), among other things.

In a laboratory, many resources, including labor and consumable items, may be utilized to process, prepare, and test a specimen. Each specimen may also pass through many lab stations and may be handled by many operators, each working at his/her own pace, resulting in difficulty determining costs and error rates associated with each station of the lab. For example, a laboratory may use an accessionist at an accessioning station to receive and prep the specimen (e.g., by labeling the specimen, listing the requested tests, etc.) before further analysis. After accessioning, a technician may carry a specimen to a grossing station to measure, cut, and record a description of the specimen. The specimen may then be manually altered by a histotech (e.g., by embedding, sectioning, staining, imaging, etc.) at subsequent stations where process and utilization data may be tracked. Then, a pathologist may review primary specimen output pieces (e.g., slides) for a diagnosis. Because pathology lab workflows vary greatly from lab to lab, obtaining an accurate accounting of the costs associated with a lab may be difficult, if not impossible, without analyzing each employee at each station over a period of time.

Some laboratories have utilized processes for tracking performance and economics by exclusively measuring use of consumables (e.g., knives, specimen stains, reagents, etc.). However, such processes fail to accurately assess variables such as employee labor cost, machine use, service, depreciation, and error rates.

SUMMARY OF THE INVENTION

According to some aspects of the invention, the present disclosure may provide a computer system for analyzing a specimen processing workflow in a pathology laboratory. The computer system may include a display and a processor. The processor may be configured to provide a first interface, a second interface, and a third interface to the display to receive, via the first interface, a first set of parameters associated with an existing specimen processing workflow in a pathology laboratory, the first set of parameters including a workflow process and a workflow scale, and determine, based on the first set of parameters, current performance data associated the existing specimen processing workflow having an associated current cost information and current time utilization. The processor may further be configured to receive, via the second interface, a second set of parameters associated with a proposed modification to the existing specimen processing workflow, the second set of parameters including parameters associated with at least one laboratory device, determine, based on the first and second sets of parameters, revised performance data having an associated revised cost information and revised time utilization, and provide an output comprising a comparison between revised performance data and current performance data.

According to another aspect of the invention, the present disclosure may provide a method for analyzing a workflow in a pathology laboratory. The method may include executing with a processor a software analysis tool configured to provide a first interface, a second interface, and a third interface, wherein the first and second interfaces each include at least one data entry form. The method may also include generating on a display the first interface, the second interface, and the third interface and providing, via the first interface, a set of parameters related to a workflow in a pathology laboratory, the first set of parameters including a workflow process and a workflow scale, and selecting, via the second interface, a proposed modification to the set of parameters, wherein the proposed modification reflects at least one laboratory device. The method may further include initiating an analysis of the workflow in the pathology laboratory based on the set of parameters and the proposed modification, and reviewing, within the third interface, a set of results generated by the analysis, wherein the set of results reflects an estimated effect of the proposed modifications.

According to yet another aspect of the invention, the present disclosure may provide an analysis tool for validating forecasted performance data of a pathology lab workflow. The analysis tool may include a display and a processor. The processor may be configured to retrieve data reflecting a machine time, a number of specimen output pieces, and timestamp information associated with a laboratory device in a pathology lab, determine, based on the retrieved data, actual performance data associated with the pathology lab, and provide an output representing the actual performance data associated with the pathology lab to the display.

According to yet another aspect of the invention, the present disclosure may provide a computer implemented method for optimizing a pathology lab workflow based on one or more user parameters. The method may include receiving one or more user parameters related to a desired outcome for a pathology lab, retrieving captured data related to a current pathology lab workflow, and executing with a processor a performance analysis tool to produce a criteria set based on the one or more user parameters and the captured data. The method may further include determining a revision to the current pathology lab workflow based on the criteria set, wherein the revised workflow reflects a laboratory device and achieves the desired outcome. The method may also include providing on a display an output related to the revision.

BRIEF DESCRIPTION OF THE DRAWINGS

The accompanying drawings, which are incorporated in and constitute a part of this specification, show certain aspects of the present invention and, together with the description, help explain some of the principles associated with the invention. In the drawings.

DESCRIPTION OF THE EMBODIMENTS

Figure 1A:
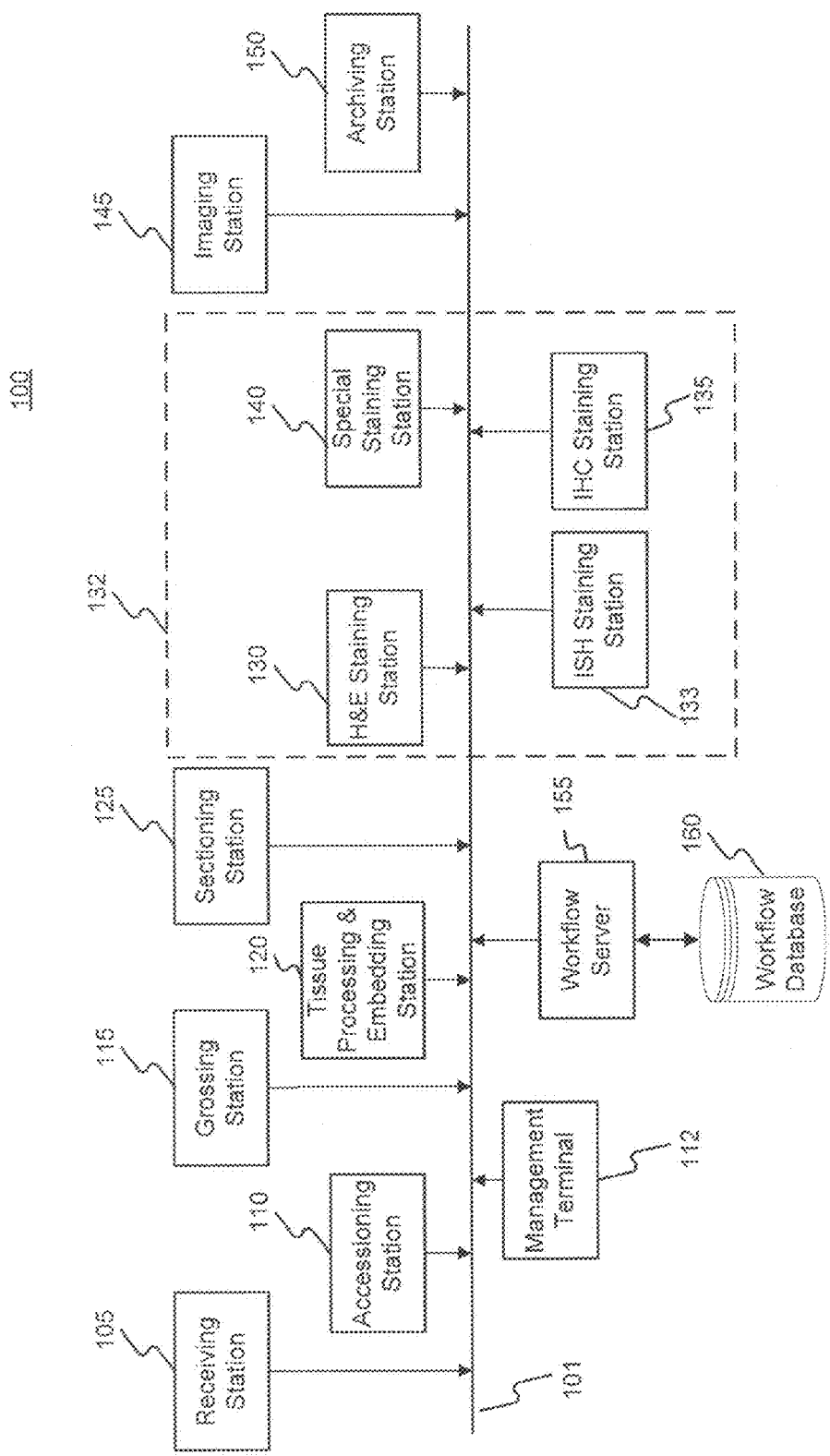
FIG. 1A is a block diagram representing an exemplary physical laboratory configuration according to some embodiments of the present disclosure.

Reference will now be made in detail to the invention, examples of which are illustrated in the accompanying drawings. The implementations set forth in the following description do not represent all implementations consistent with the claimed invention. Instead, they are merely some examples consistent with certain aspects related to the invention. Wherever possible, the same reference numbers will be used throughout the drawings to refer to the same or like parts.

Systems and methods consistent with the invention may determine performance data associated with one or more aspects of a pathology laboratory handling one or more specimens. As used herein, the term "specimen" broadly refers to any material or piece of material obtained for the purpose of performing an operation in a laboratory. For example, the laboratory may receive a specimen removed from a living being and prepare the specimen for analysis, testing, and/or storage. Exemplary types of specimens include tissue or other biologic samples taken from an animal or human. Further, as used herein, the term "workflow" broadly refers to a path or order of operations that a specimen may follow in a laboratory and laboratory devices included for purposes of carrying out operations on a specimen. For example, the term workflow may reflect the order in which a series of laboratory stations may process the specimen and/or a series of laboratory devices (e.g., microtomes, stainers, etc.) that may be included within the workflow. The term "laboratory device" as used herein shall mean any tool or implement used in a pathology laboratory including, but not limited to, autostainer devices, microtomes, specimen identifying devices (e.g., bar code scanner/reader), specimen marking devices (e.g., barcode printer), image scanning and sharing devices, image analysis devices, cover slipping devices, slide pretreatment devices, tissue processing devices (e.g., an autoprocessor), information display devices (e.g., computers) and any software associated therewith. The term "workflow information" may broadly refer to any information and/or data related to a specimen's workflow and/or data received from one or more laboratory devices present in the workflow. The term "performance data," as used herein shall mean any data related to laboratory performance and performance metrics including, but not limited to, cost information, error information, time utilization information, and device utilization information, among others.

In one exemplary implementation, systems and methods consistent with the invention may provide computer-implemented interfaces and analysis tools for providing, analyzing, validating, and optimizing performance data associated with a pathology laboratory. For example, a performance analysis tool may be accessed from a virtual laboratory interface, which represents an actual or physical laboratory or laboratories for processing a specimen. Through the performance analysis tool, a user may provide data associated with a current laboratory workflow as well as one or more proposed revisions to that workflow (e.g., addition of a new staining device), and be provided a performance forecast based on the revisions. A performance analysis system may function as a Pathology Economic Modeling system, hereinafter PEM, that provides performance forecasts about the operational characteristics (e.g., economics) of a current or projected pathology workflow. As described in more detail below, exemplary embodiments further include tools for validating a previously forecast performance and optimizing an existing workflow to meet one or more desires of a user.

Figure 1B:
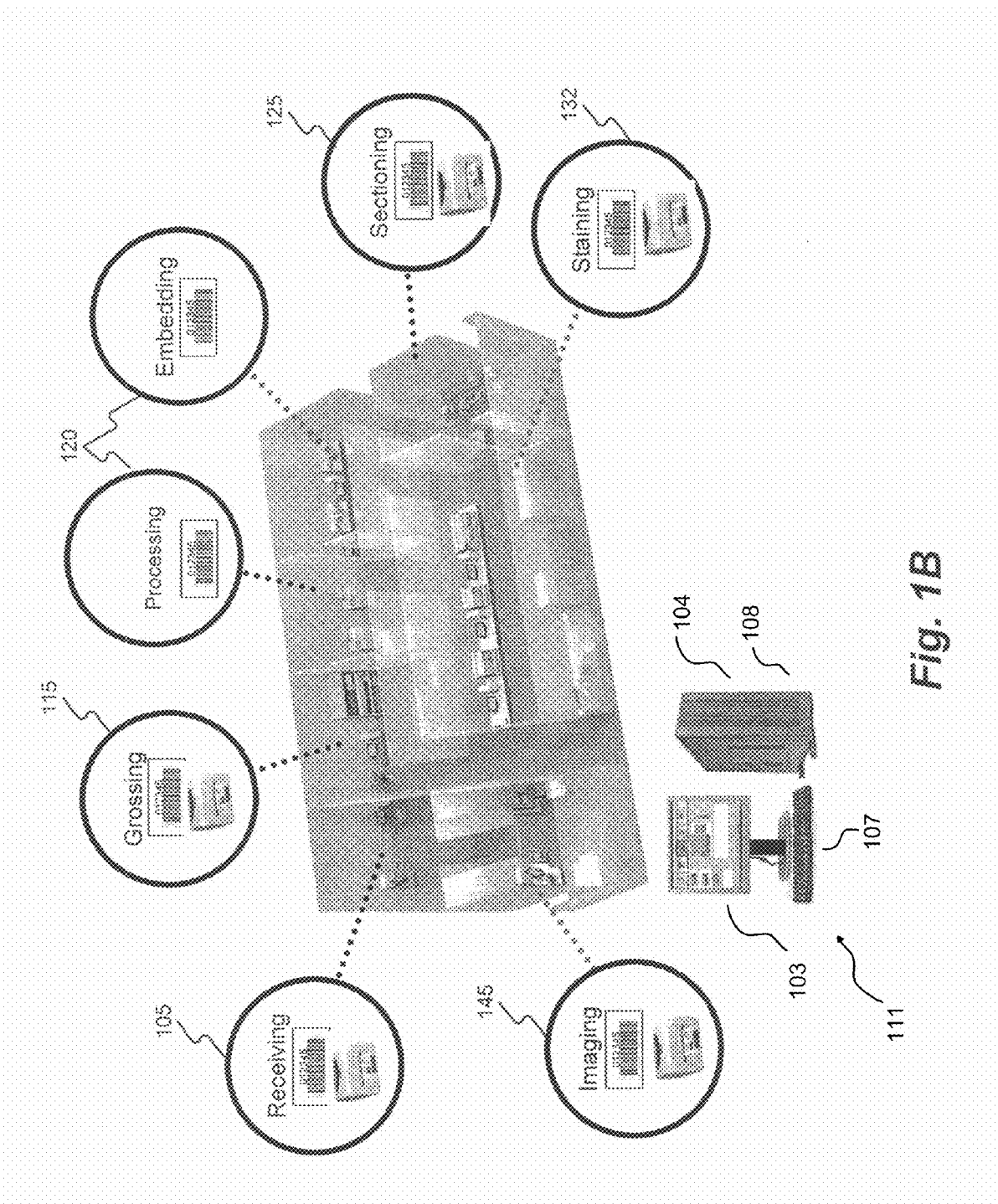
FIG. 1B is a representation of an exemplary pathology lab and associated stations.

FIG. 1A is a block diagram of an exemplary physical laboratory environment 100 consistent with exemplary embodiments of the present disclosure. FIG. 1B is an exemplary illustration of a virtual laboratory representation including exemplary stations associated with a physical laboratory. The exemplary configuration shown in FIG. 1A generally relates to a pathology laboratory; however, systems and methods consistent with the invention equally apply to other types of laboratories. Thus, as used herein, the term "laboratory" and/or "lab" broadly refer to any type of actual laboratory (or laboratories) for handling specimens. The term "virtual laboratory," as used herein, broadly refers to a virtual illustration or depiction of a physical laboratory or laboratories. For example, a virtual laboratory may be a computer-implemented graphical representation or model of a physical laboratory. The virtual laboratory may depict the appearance or organization of the physical laboratory, or may include logical components substantially similar to an actual laboratory.

As shown in FIGS. 1A and 1B, laboratory environment 100 may include a network 101, a receiving station 105, an accessioning station 110, a grossing station 115, a tissue processing and embedding station 120, a sectioning station 125, staining stations 132 (e.g., an H&E staining station 130, an IHC staining station 135, and a special staining station 140), an imaging station 145, and an archiving station 150. Each of these stations may include one or more process specific laboratory devices. For example, a microtome may be present at sectioning station 125, microscopes and automated microscopes at imaging station 145, an automated tissue processor and a paraffin embedder at tissue processing and embedding station 120, and one or more stainers at staining stations 132. In addition, each station may include specimen identification devices such as, for example, a barcode reader, identification software, and a barcode/label printer for providing identification services related to each specimen and/or output piece (e.g., the specimen output piece may be a specimen bag or specimen jar at the accessioning station, a tissue cassette at the grossing station, a specimen slide at the sectioning station, etc.).

In addition to the stations associated with the laboratory, a management terminal 112, a workflow server 155, and a workflow database 160 also may be included. Management terminal 112, workflow server 155, and workflow database 160 may each be implemented on any computing device 111, such as, for example, a personal computer (PC), personal digital assistant (PDA), mainframe, mainframe terminal, or other computer-implemented device suitable for interfacing with a user. In one example, management terminal 112, workflow server 155, and workflow database 160 may all be implemented on a single computing device 111. Therefore, the following description of server 155 may apply to any other computing devices 111 associated with laboratory environment 100.

In one implementation (as seen in FIG. 1B), a computing device 111, such as workflow server 155, may include a central processing unit 104, as well as other components, such as, for example, a display 103, an input device 107 and a network controller (108). Workflow server 155 may display information on a display or at other remote locations, such as, for example, a remote computing device 111 connected via a network.

In the following discussion, it is important to note that each of receiving station 105, accessioning station 110, grossing station 115, tissue processing station 120, sectioning station 125, staining stations 132, imaging station 145, and archiving station 150, and any other lab station present may include one or more computing devices 111 for purposes of interfacing with a user, (e.g., displaying information related to a specimen, receiving input from a bar code reader, and providing output to a bar code printer). The implementation of such computing devices 111 at stations in a lab may on an as-desired basis and may be determined by a user, lab manager, or any suitable decision maker.

Further, stations 105 to 150 and associated devices (e.g., automated microtome, auto stainer, etc.), workflow server 155, and management terminal 112, may each communicate with one another via network 101. By enabling communication among the many laboratory devices associated with the laboratory stations, data regarding a specimen as well as operation of the devices (e.g., hours in use, timestamp information, operator ID, materials consumed, etc.) may be provided to workflow server 155 for storage in workflow database 160 and desired processing (e.g., validation of previously forecast performance data). As used herein, the term "timestamp information" shall mean any information related to date and/or time and associated with a process and/or specimen. For example, timestamp information may include a time into a station (e.g., 11:00 AM), a time out of a station (e.g., 11:30 AM), and a time in a machine (e.g., 30 minutes), among others.

Laboratory environment 100 may include more or fewer stations than those shown in the exemplary diagram of FIG. 1. For example, exemplary arrangements may use only accessioning station 110, tissue processing station 120, H&E staining station 130, and imaging station 145. In addition, the order in which the various stations are shown in FIGS. 1A and 1B, and described throughout the present disclosure, is not intended to be limiting. One of ordinary skill in the art will recognize that such stations may be organized in any desirable order without departing from the scope of the present disclosure.

Network 101 may enable communicative connections between devices within a physical laboratory and may be any suitable network enabling information transfer among electronic devices. For example, network 101 may include an Ethernet LAN, a wide-area network (WAN), and/or the Internet, among other things. Each station or server associated with laboratory environment 100, and each device within a station, may include a communicative connection with network 101, and therefore may be communicatively connected to other laboratory devices present within a physical laboratory. This may allow each laboratory device to request and share data with workflow server 155, among other things.

Workflow database 160 may include relational database management software (e.g., MS SQL Server, Oracle, MySql, etc.), flat file storage, and/or any suitable systems for enabling data persistence. For example, workflow server 155 may include software associated with a relational database management system, allowing persistent storage of workflow data associated with a current workflow in a pathology laboratory. Alternatively, such data may be persisted through storage methods implemented via spreadsheet software, word processing software, or any other suitable package enabling storage (e.g., basic file system i/o commands).

Receiving station 105 and/or accessioning station 110 may be configured to receive specimens from various sources, including, for example, hospital staff, couriers, and commercial shippers, among others. Receiving station 105 and/or accessioning station 110 may include numerous laboratory devices configured for accomplishing tasks related to receiving and initial preparation of specimens. For example, stations may include a barcode scanner, a printer (e.g., configured for barcode and label printing), and/or a computing device 111 configured to receive input from an operator and provide identification services, among others. The term True Positive ID, hereinafter TPID, refers to a True Positive Identification system that may track specimen input pieces and specimen output pieces through the pathology workflow. A TPID system may also display or automatically execute station-specific instructions at the stations.

As noted above, some or all of the devices of receiving station 105 and/or accessioning station 110 may communicate with workflow server 155 via network 101. Stations 105 and/or 110 may then provide specimen data (e.g., patient name, specimen weight, etc.) and operational data (e.g., timestamped time in/time out information, operator id, etc.) to workflow server 155. Further, one or more of the laboratory devices associated with receiving station 105 and/or accessioning station 110 may include automated features, and/or may involve some manual interaction from an operator.

Because functionality associated with receiving station 105 and/or accessioning station 110 may be similar, stations 105 and 110 may be combined as one station. In such an embodiment, personnel and laboratory devices associated with receiving station 105 and accessioning station 110 may be utilized for performance of the related processes at both stations.

Grossing station 115 may be configured for performing an examination of a specimen, preparing a related description of the specimen according to shape, size, and pathoanatomic findings, and cutting a specimen to fit a specimen cassette or other suitable container. Therefore, grossing station 115 may include one or more laboratory devices, such as, for example, a low power microscope, a barcode scanner and a cassette printer configured to print barcode information to a specimen cassette. The laboratory devices associated with grossing station 115 may also communicate with workflow server 155 via network 101 or other suitable connection, and provide specimen and operational data (e.g., timestamp information, operator id, etc.), among other things, to a user. Further, one or more of the laboratory devices associated with grossing station 115 may include automated features, and/or may involve some manual interaction from an operator.

Tissue processing and embedding station 120 may be configured for processing and embedding a specimen in preparation for sectioning station 125. Tissue processing and embedding station 120 may include one or more laboratory devices, for example, a tissue processor configured to dehydrate a specimen, a paraffin embedding device, and a barcode reader, among other things. The laboratory devices associated with tissue processing and embedding station 120 may communicate with workflow server 155 via network 101 or other suitable connection and provide specimen data and operational data (e.g., timestamp information, operator id, etc.), among other things. Further, one or more of the laboratory devices associated with tissue processing and embedding station 120 may include automated features, and/or may involve some manual interaction from an operator.

Sectioning station 125 may be configured to receive an embedded specimen from tissue processing and embedding station 120 and produce slides of a specimen sectioned based on common practice and/or additional instructions. It is important to note that the term "sectioning" may also be referred to as "cutting" and/or "microtoming," among other things by those of ordinary skill in the art. The term "sectioning" is therefore not intended to be limiting. Sectioning station 125 may include one or more laboratory devices, for example, a microtome (i.e., a sectioning device), an oven or other heating device, a barcode reader, and a printer (e.g., a slide label printer), among other things. The laboratory devices associated with sectioning station 125 may communicate with workflow server 155 via network 101 or other suitable connection and provide specimen data and operational data (e.g., timestamp information, operator id, etc.), among other things. Further, one or more of the laboratory devices associated with sectioning station 125 may include automated features, and/or may involve some manual interaction from an operator.

H&E staining station 130, ISH staining station 133, IHC staining station 135, and special staining station 140 may be configured for staining primary specimen output pieces (e.g., slides) in accordance with well known practices to those skilled in the art. H&E staining station 130, ISH staining station 133, IHC staining station 135, and special staining station 140 may include one or more stainers (e.g., automated and/or manual devices configured to apply measured amounts of stain and/or other chemicals to particular specimen slides), a pre-treatment system, stain kits and reagents, and a barcode scanner, among others. The laboratory devices associated with H&E staining station 130, ISH staining station 133, IHC staining station 135, and special staining station 140 may communicate with workflow server 155 via network 101 or other suitable connection and provide specimen data (e.g., stains used, number of primary specimen output pieces processed, etc.) and operational data (e.g., timestamp information, operator id, etc.), among other things. Further, one or more of the laboratory devices associated with H&E staining station 130, ISH staining station 133, IHC staining station 135, and special staining station 140 may include automated features, and/or may involve some manual interaction from an operator. One of ordinary skill in the art will recognize that the staining stations described herein are exemplary, and more or fewer staining stations may be utilized as desired.

Imaging station 145 may be configured for examination of one or more primary specimen output pieces (e.g., slides) for diagnosis. Imaging station 145 may include laboratory devices, such as a microscope, a slide scanner/etcher, a barcode scanner, and a printer (e.g., configured to print reports), among other things. The laboratory devices associated with imaging station 145 may communicate with workflow server 155 via network 101 or other suitable connection and provide specimen data (e.g., specimen images) and operational data (e.g., timestamp information, operator id, etc.), among other things. Further, one or more of the laboratory devices associated with imaging station 145 may include automated features, and/or may involve some manual interaction from an operator.

Archiving station 150 may be configured to archive primary specimen output pieces produced from a particular specimen for reference at a later time, and may also archive images stored for a period of time via imaging station 145. Archiving station 150 may include laboratory devices, for example, a barcode scanner, a printer (e.g., barcode printer), and storage facilities, among other things. The laboratory devices associated with archiving station 150 may communicate with workflow server 155 via network 101 or other suitable connection and provide specimen data (e.g., specimen images) and operational data (e.g., process time for a specimen, time in use, operator id, etc.), among other things. Further, one or more of the laboratory devices associated with archiving station 150 may include automated features, and/or may involve some manual interaction from an operator.

Management terminal 112 may be configured to provide an analysis tool 300 for processing performance data related to a laboratory as well as virtual lab interface for accessing numerous aspects of a workflow associated with a lab.

Figure 1C:
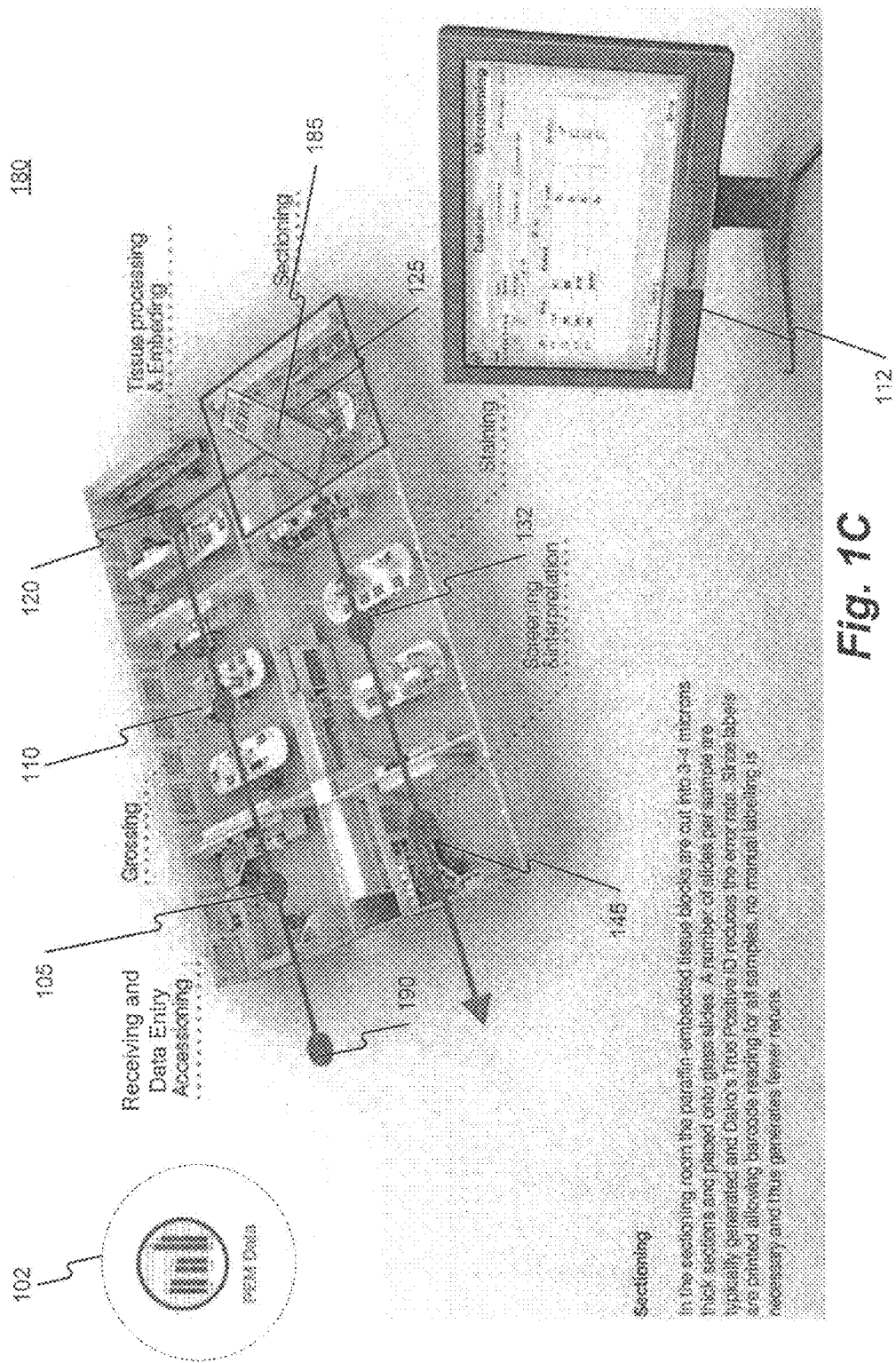
FIG. 1C is a representation of an exemplary virtual lab interface consistent with some embodiments of the present invention.
Figure 1D:
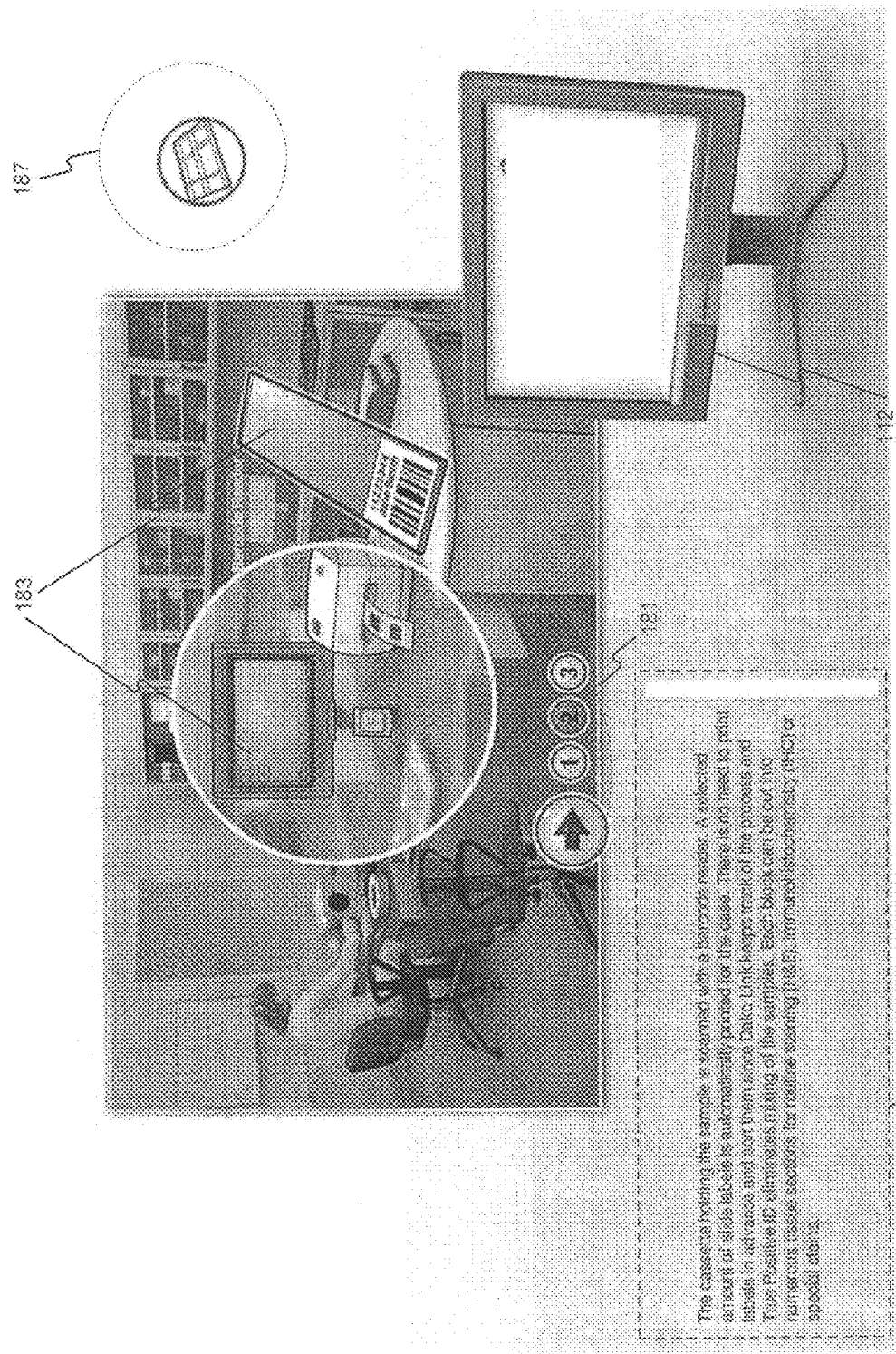
FIG. 1D is a representation of an exemplary station interface associated with the virtual lab of FIG. 1C.

FIG. 1C is a representation of an exemplary virtual lab interface consistent with some embodiments of the present invention, while FIG. 1D is a representation of an exemplary station interface associated with the exemplary virtual lab interface shown in FIG. 1C. Virtual laboratory 180 may include one or more virtual laboratory stations representing the actual physical stations present within an actual laboratory. This is show in FIG. 1C by virtual representations of receiving and accessioning station 105, grossing station 110, tissue processing and embedding station 120, sectioning station 125, staining stations 132, and imaging station 145. Virtual laboratory 180 may also display a specimen indicator 185, a workflow indicator 190, and PEM selector 102 enabling access to analysis tool 300.

Specimen indicator 185 may be configured to indicate a specimen location, a specimen station, and a specimen flow in relation to the one or more of the virtual laboratory stations. Such indication may be accomplished by applying various visual techniques to specimen indicator 185 and may allow a user to visualize a workflow. For example, in FIG. 1C, a specimen is depicted as having arrived at sectioning station 125. Therefore, specimen indicator 185 is shown as a slide, representing that a specimen may be sectioned and placed onto a slide for imaging/viewing at sectioning station 125. One of ordinary skill will recognize that such depictions or appearances are exemplary only and other appearances may be applied to specimen indicator 185 to demonstrate a specimen's state, among other things.

In some embodiments, upon selection of a virtual representation of a lab station (e.g., sectioning station 125), a supplemental view of the selected laboratory station may be provided as shown in FIG. 1D. This supplemental view may be a more detailed representation of a station, such as sectioning station 125. In FIG. 1D, such a representation of sectioning station 125 is shown following, for example, a user mouse-clicking the virtual representation of sectioning station 125 within the virtual lab 180. Supplemental views may show one or more virtual representations of laboratory devices 183 present in the related physical laboratory (e.g., label printer, barcode reader, microtome, etc.). Further, the supplemental views may include one or more additional active components 181, a text component 186, and return component 187, among other things. While supplemental component views may be discussed in the context of "zoomed-in" and "detailed," additional visual effects may be utilized for providing such components.

Return component 187 may allow a user selection indicating a return to a view level above the currently selected view. For example, where a user has selected an active component indicating a drilldown view of a virtual laboratory station from virtual laboratory 180, return component 187 may cause a return to a view of virtual laboratory 180 within the interface.

Additional active components 181 may include an arrow component and two numbered components (e.g., 1 and 2). Where a user desires to see a step-by-step of the workflow associated with the current laboratory station and obtain related information to each step, the user may select the arrow component as desired, and each process in the current laboratory station may be displayed within the interface and described in text component 186. Alternatively, if a user wishes to review an individual process associated with the currently selected virtual laboratory station, the user may click one of the available numbered components (e.g., 1 and/or 2) to be taken directly to a data and description associated with the selected step.

Additionally, a user may access performance data associated with a particular station from the supplemental view. For example, where a user desires to review an average cost per slide at sectioning station 125, the user may access a performance reporting module from within the supplemental view (not shown). Note that the description related to sectioning station 125 is exemplary only, and such functionality may be provided for any station associated with a laboratory. For example, any of receiving station 105, grossing station 115, staining stations 132, imaging station 145, and archiving station 150, among others, may be accessed and workflow information retrieved. In addition, performance data associated with any of the stations may be analyzed and/or workflow elements modified from within the interface. This may allow a forecasted performance for the station and/or the lab as a whole to be provided and compared to existing performance data.

Figure 2:
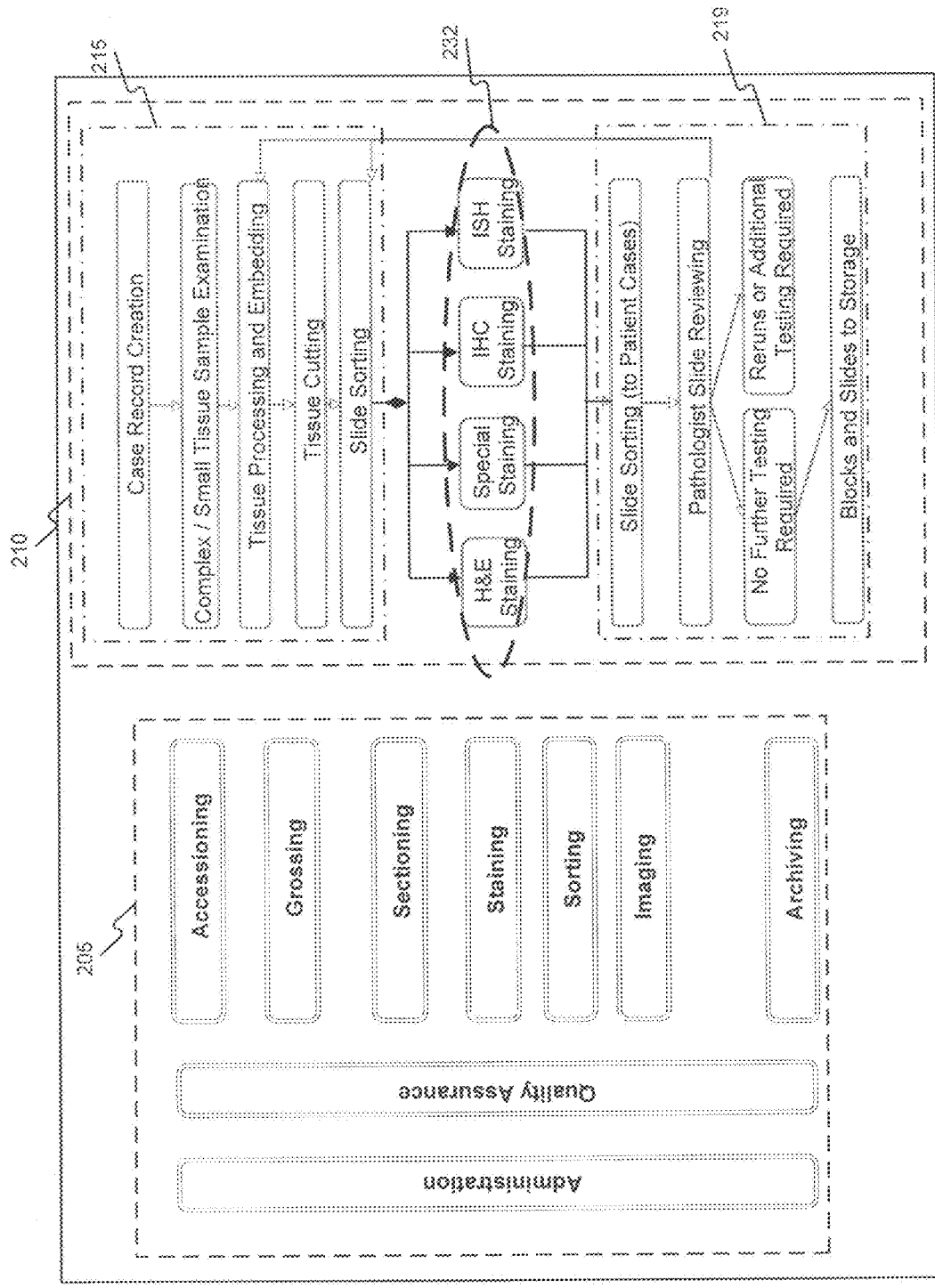
FIG. 2 is an exemplary block diagram representing an exemplary workflow of a pathology laboratory as related to exemplary processes carried out in the laboratory.

A user may access an analysis tool 300 configured to analyze a work flow and proposed modifications to a workflow via PEM selector 102. FIG. 2 shows a schematic representation of an exemplary relationship between workflow processes and an exemplary workflow upon which an exemplary analysis tool may be based. Workflow processes, as described above may include accessioning, grossing, sectioning, staining, sorting, imaging, and archiving. Process diagram 205 provides an exemplary representation of a collection of such workflow processes. In addition, administration and quality assurance may be carried out as a function of each of these workflow processes, and is therefore shown as such. One exemplary workflow configuration can be seen at workflow 210. Case record creation may occur during the accessioning process. Complex and small tissue sample examination may take place during the grossing process. A sectioning process may include tissue processing and embedding as well as tissue sectioning (cutting). Note that other workflows may separate or combine one or more of these processes into a single process and/or lab station.

Workflow 210 highlights a workflow on which an analysis tool for a pathology laboratory may be based. It has been determined that in some embodiments, a work product of a pathology lab can be determined based on primary specimen output pieces (e.g., slides) from the staining stations 132. The term "specimen output piece," as used herein, shall include the deliverable of any particular lab station and/or process. For example, a specimen output piece from grossing station 115 may be a specimen cassette, while a specimen output piece from tissue processing station 120 may be a tissue block (e.g., specimen from cassette cut and encased in paraffin). The term "primary specimen output piece," as used herein, shall mean the specimen output piece that may be considered the product goal of a particular laboratory. For example, in a pathology laboratory, staining stations 132 may produce stained specimen slides for subsequent review by a pathologist. Such specimen slides may be considered the primary specimen output pieces of the pathology lab. Each of pre-stain processes 215 and post-stain processes 219, although producing specimen output pieces of their own, operate for the purpose of preparing and/or evaluating primary specimen output pieces of existing staining processes 232. Therefore, by allocating workflow costs associated with each of pre-stain processes 215 and post-stain processes 219 across a total number of primary specimen output pieces from staining stations 132 (e.g., slides), while allocating only those costs incurred for a particular primary specimen output piece in each of the staining processes 232 through which it passed, creation of a highly accurate model of a pathology lab workflow may be enabled.

Figure 3A:
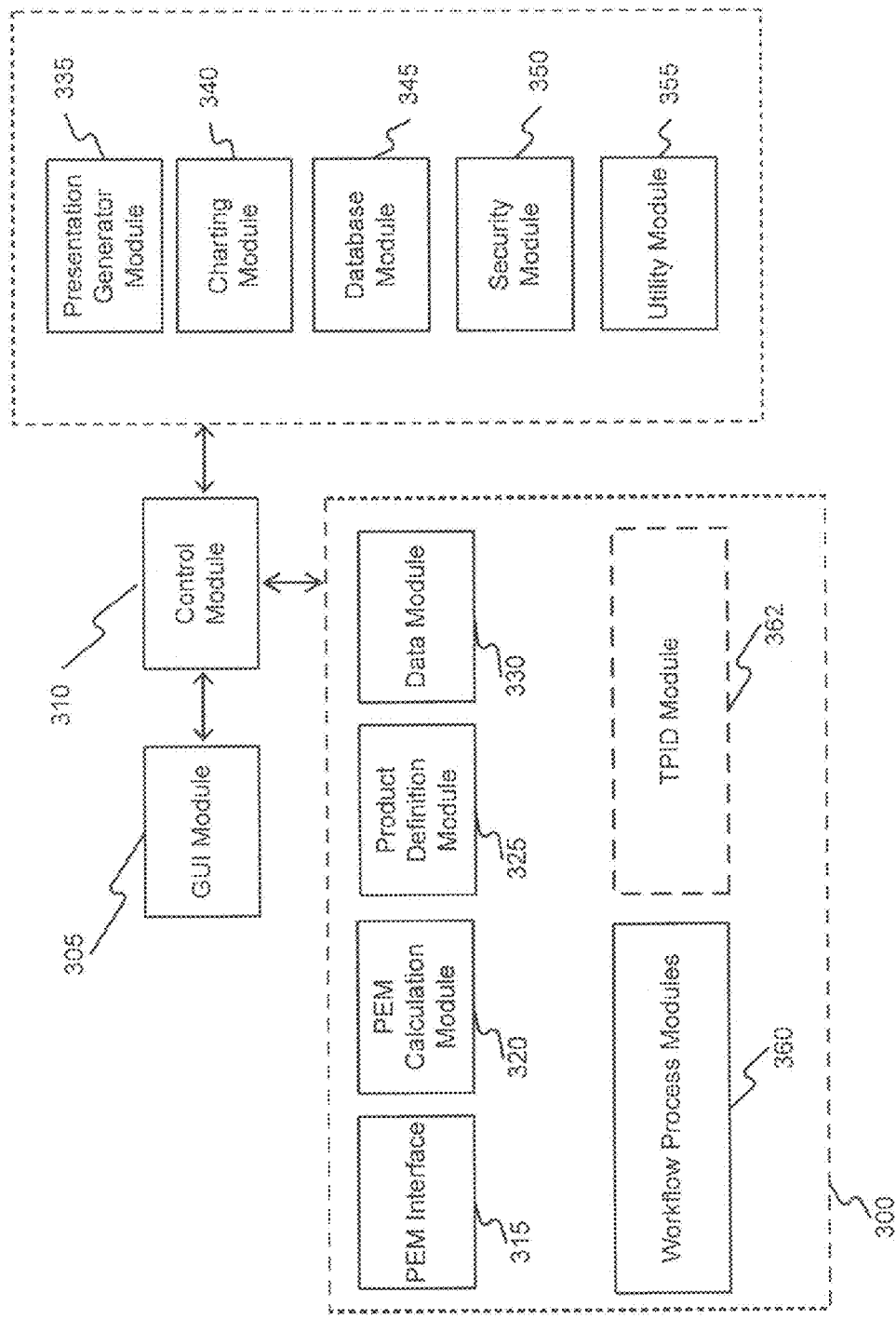
FIG. 3A is an exemplary block diagram representing functional modules that may be associated with a performance analysis tool for purposes of providing functionality associated with an analysis of a workflow.

FIG. 3A is an exemplary block diagram representing functional modules that may be associated with a performance analysis tool 300 for purposes of providing functionality associated with an analysis of a workflow. Such modules may enable capture, processing, analysis, and display of workflow and performance data related to a laboratory. In one arrangement, these functional modules may be stored on a disk in workflow server 155 and/or on a server separate from workflow server 155. Such modules may include compiled computer code providing functions related to visualization (e.g., GUI module 305), lab operations (e.g., workflow process modules 360), utilities (e.g., utility module 355), and performance analysis (e.g., PEM calculation module 320). The modules may be implemented using any programming language and/or data structure, such as, for example Java, C++, Basic, VBA, spreadsheet macros, etc. Each module may also present an application programming interface (API) for purposes of data transfer and method access, and may be enabled for remote procedure calls (RPC) and instantiation.

Figure 3B:
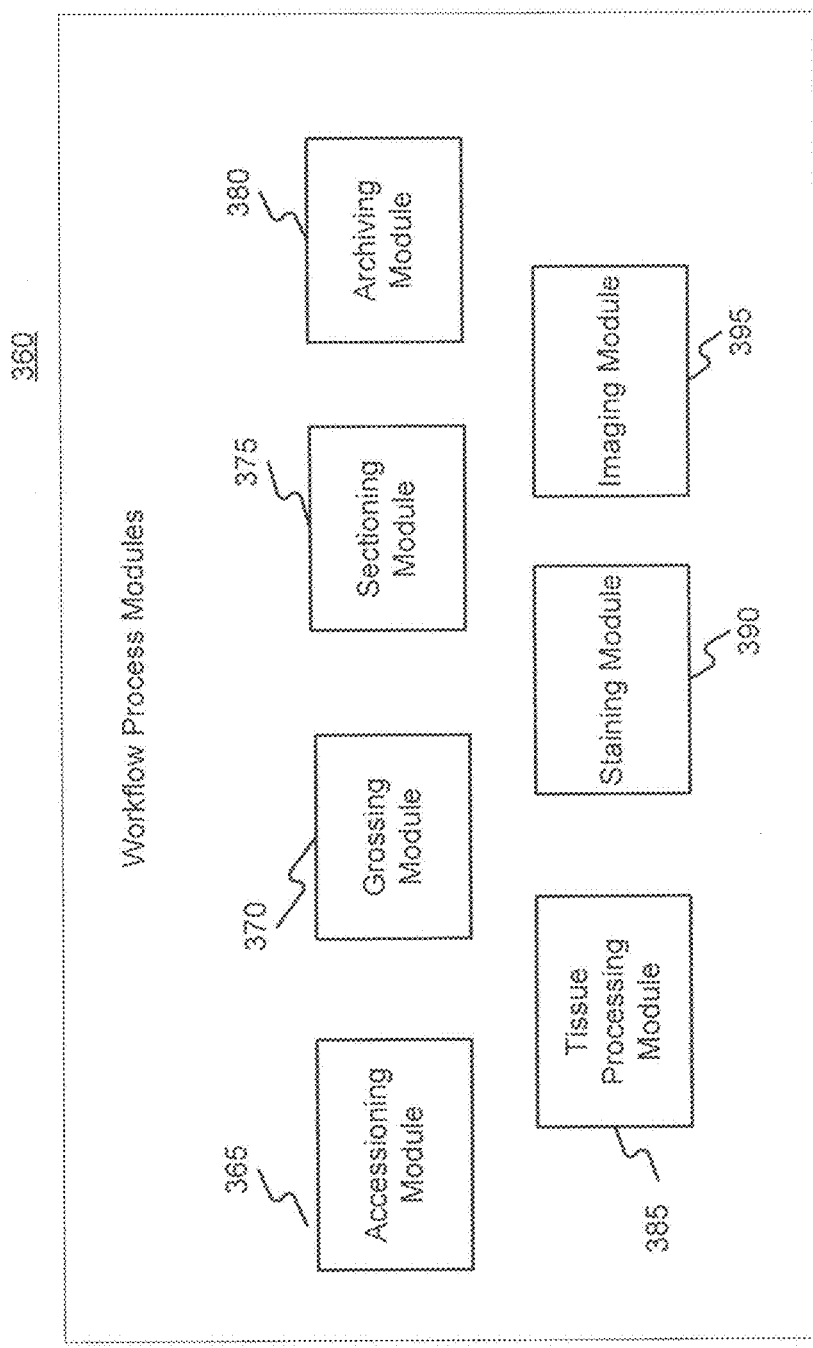
FIG. 3B is a block diagram highlighting the functional modules associated with the various stations of a laboratory workflow.

The following includes a brief overview of the modules described at FIGS. 3A and 3B, and is intended to be exemplary only. One of ordinary skill in the art will recognize that more or fewer functions and data structures may be available from any particular module, that functionality associated with the modules may be allocated differently, and that different packages and class hierarchies may be utilized during development, as desired.

GUI module 305 may provide processing for display of interfaces (e.g., data entry interfaces), display of output data (e.g., performance data), and receipt of selections from users related to one or more workflow modifications. For example, GUI module 305 may generate a graphical user interface (GUI) displaying a first interface presenting a data entry form allowing a user to configure a workflow associated with a physical laboratory. Upon receipt of workflow data, GUI module 305 may provide the user data to control module 310 for storage through database module 330, PEM interface module 315, or other suitable module. In addition, GUI module 305 may provide various charts, tables, and graphs generated by presentation generator module 335, charting module 340, or other suitable module, and related to output associated with current performance and/or outlook data, among other things. Graphical input and output related to GUI module 305 will be discussed in greater detail below with regard to FIGS. 9A-12I.

GUI module 305 may utilize numerous formats and programming languages for providing an interface. For example, in some embodiments, a graphics/animation tool (e.g., iLOG JViews, Adobe Flash, etc.), HTML, spreadsheet tools, and/or XML may be utilized for implementing a particular GUI through GUI module 305. One of skill in the art will recognize that various combinations may be used without departing from the scope of the present invention.

Control module 310 may be configured to receive and interpret user inputs, manage data flow through analysis tool 300, and manipulate GUI module 305 to render graphical output, as desired. For example, GUI module 305 may provide user input to controller module 310 for provision to data module 330 and storage by database module 345 at workflow database 160. In another example, data resulting from calculations described below may be provided by PEM calculation module 345 to control module 310, whereby controller module 310 may provide such data to charting module 340, presentation generator module 335 and/or GUI module 305 for providing output of the results in a desired format. One of ordinary skill in the art will recognize that controller module 310 may perform more or fewer operations, as desired.

PEM interface module 315 may be configured to enable interaction between functional modules of analysis tool 300 and for generating data related to an interface currently displayed via GUI module 305. For example, PEM interface 315 may include code for rendering a first, second, and third interface related to analysis tool 300 and providing input received via the first and second interfaces to analysis tool 300. In such an exemplary embodiment, PEM interface module 315 may provide a first interface having one or more data sections related to configuring an existing workflow associated with a pathology lab. These data sections may include one or more controls (e.g., textbox controls, button controls, dropdown controls, etc.) used for inputting data related to a current workflow. Therefore, PEM interface module 315 may generate a definition of the first interface for provision to control module 310 and GUI module 305. In addition, PEM interface module 315 may provide a second interface having one or more data sections enabling a user to provide a proposed modification to the existing workflow. Therefore, PEM interface module 315 may provide definition of controls related to entry of these modifications (e.g., textbox controls, button controls, etc.) to control module 310 for provision to GUI module 305 or other suitable module. Further, PEM interface module also may provide a third interface for viewing results of one or more calculations performed by analysis tool 300. For example, one or more charts, graphs, tables, etc. may be displayed showing data related to a performance position of a lab and/or forecasted performance data of a lab, among other things. PEM interface module 315 may therefore include code for generating such displays for provision to control module 310 and GUI module 305. It is contemplated that PEM interface module 315 may also be configured to generate additional interfaces. The additional interfaces may provide, for example, other data associated with the laboratory, laboratory devices, laboratory workflow, etc.

PEM calculation module 320 may be configured to perform various calculations associated with generating result sets associated with current performance data, forecasted performance, performance validation, and workflow optimization. For example, PEM calculation module 320 may include computer code and data structures directed to determining a performance condition based on one or more parameters of a current workflow, determining a performance outlook based on one or more proposed workflow modifications, validating a previously forecast performance, and optimizing a workflow based on one or more user parameters, among others. PEM calculation module 320 may have a series of properties, functions and methods including the data structures and computer code for accomplishing these determinations. Calculations and determinations will be discussed in greater detail below with regard to FIGS. 4-8.

Product definition module 325 may include functionality for providing, editing, and deleting a data representation of one or more laboratory devices that may be used for proposed workflow modifications, among other things. For example, numerous lab devices (e.g., autostainer devices, microtome devices, specimen identifying devices, specimen marking devices, image sharing devices, image analysis devices, cover slipping devices, slide pretreatment devices, tissue processing devices, etc.) may be stored in workflow database 160 with various parameters defining functionality and benefits associated with each device. Product definition module 325 may provide access to the various products allowing display of associated parameters, editing of such parameters, and/or adding/deleting of a laboratory device from the collection. In such an example, a user may wish to propose a modification to an existing workflow via a second interface provided by PEM interface module 315. Therefore, product definition module 325 may provide data associated with one or more laboratory devices available for adding to a configured workflow to PEM interface module 315 for providing to control module 310. Further, control module 310 may provide, through PEM interface module 315, modifications to various parameters that should be stored with a particular device provided by product definition module 325. One of ordinary skill in the art will recognize that more or fewer functions may be provided by product definition module 325 without departing from the scope of the present disclosure.

Data module 330 may be configured to parse requests related to data associated with the analysis tool 300. For example, data module 330 may receive a request from control module 310 and/or PEM calculation module 320 to assemble a data set including parameters associated with a current workflow associated with a laboratory. Data module 330 may instantiate one or more modules from workflow process modules 360 and retrieve data based on the request. Data module 330 may then analyze the data (e.g., validate the data) and provide the data to control module 310 and/or PEM calculation module 320, among others, for processing. Similarly, where a request to store data is initiated by a module associated with analysis tool 300, data module 330 may receive and analyze the data for a determination of validity, among other things, and provide the data to control module 310 and/or database module 345, among others.

Presentation generator module 335 may be configured to receive data related to a first, second, and/or third interface associated with analysis tool 300 (e.g., from PEM interface module 315) and format such data into output for presentation to a user via control module 310 and GUI module 315. For example, in response to a user request through GUI module 305 and/or control module 310, presentation generator module 335 may receive data from PEM interface module 315 and a request to format such data based on parameters associated with the request. Such parameters may indicate that the data should be formatted in tabular, chart, textbox, or other controls for presentation to the user. One of ordinary skill in the art will recognize that numerous functions and methods may be available through presentation generator module 335 for formatting output based on user desires.

Charting module 340 may contain functions and methods for providing presentation generator module 335, among others, with graphical charts of data related to performance data and performance outlooks associated with a pathology laboratory. Charting module 340 may include third-party software for providing such functionality (e.g., iLog JViews, Microsoft Excel, etc.), and/or may include custom developed software capable of forming data into charts configured to demonstrate results. For example, charting module 340 may receive a request for a bar chart showing a current cost per primary specimen output piece from a laboratory for an executive summary view. Charting module 340 may prepare bar chart output relating the data to axes within the chart and provide the output presentation generator module 335, control module 310, and/or any other suitable module for output via GUI module 305. Likewise, charts related to numerous other data views to be described in greater detail below may be prepared via charting module 340.

Database module 345 may be configured to function as an interface between workflow database 160 and workflow server 155, among other things. For example, database module 345 may implement properties and methods enabling storage and retrieval of data from workflow database 160 via various connection methods (e.g., ODBC). Therefore, database module 345 may provide query processing and dataset return methods configured to standardize data access across modules of workflow server 155. In such an example, one of workflow modules 360 may provide a series of data to database module 345, and database module 345 may be responsible for executing a query causing the data to be stored in workflow database 160. Alternatively, when a request for data is made by, for example, data module 330, database module 345 may parse the request and execute a query related to the request and return the requested data.

Security module 350 may provide functionality related to authentication of users, encryption of data, and access to functionality associated with analysis tool 300, among other things. For example, GUI module 305 may provide a user login screen prior to allowing access to functionality associated with analysis tool 300. Upon providing user authentication information (e.g., username/password) GUI module 305 may cause the authentication information via control module 310 to security module 350 for authentication. Where authentication is made, security module 350 may subsequently analyze user requests for functionality associated with analysis tool 300 and determine whether the user's authentication information allows access to functionality. For example, a user may request to edit parameters associated with a laboratory device through product definition module 325. Where such a request is made, security module 350 may be provided the request via control module 310 and determine if the user is allowed to access the functionality, denying or allowing the request based on the determination.

Utility module 355 may be configured to provide various utility functions associated with analysis tool 300. For example, functionality associated with data imports and exports may be provided by utility module 355. In such an example, where a user desires to export data related to current performance, a performance outlook, proposed workflow modifications, etc., a request may be made to utility module 355 to export the data into, for example, a presentation format (e.g., MS PowerPoint). Upon initiating such a request, utility module may interface with available APIs to output the data as requested by a user. In another example, utility module 355 may provide functionality enabling a user to import data from various sources, for example, from spreadsheets (e.g., Excel), text documents (e.g., comma delimited), etc.

TPID module 362 may include functionality enabling an interface between workflow modules 360 and analysis tool 300. As described below, each workflow module in workflow modules 360 may provide actual specimen processing data to workflow server 155 and workflow database 160. Such data may include operator ID, machine time, timestamp information, etc. Through TPID module 362, data associated with actual specimens being processed at each lab station in a physical laboratory may be accessed and provided to analysis tool 300 for varied purposes. For example, for purposes of validating previously forecast performance data, data captured by workflow modules 360 over a particular time period (e.g., one month) may be accessed through TPID module 362 for purposes of determining the accuracy of the previously forecast performance data. TPID module 362 may enable various other functionality, as desired.

Workflow modules 360 may be included with analysis tool 300 and further linked into various laboratory devices available within a laboratory workflow. FIG. 3B is a block diagram highlighting the functional modules within workflow modules 360. Accessioning module 365 may be configured to provide functionality related to shipping and receiving station 105 and/or accessioning station 110. For example, in some embodiments, accessioning module 365 may be configured to receive information related to a received specimen (e.g., patient name, patient ID, timestamp information, etc.) and store such information in workflow database 160 so that the information is associated with or linked to a current specimen. Data provided to accessioning module 365 may be received on an automated basis from laboratory devices associated with receiving station 105 and/or accessioning station 110, and/or from manual entry by a technician at receiving station 105 and/or accessioning station 110 through workflow server via network 101, or other suitable method.

Further, accessioning module 365 may be configured to provide accessioning data previously stored to database 160 in response to a request from workflow server 155 and/or analysis tool 300. Such requests may include, for example, timestamp information (e.g., time in/time out) for a specimen receiving/accessioning procedure.

Grossing module 370 may be configured to provide functionality associated with grossing station 115. For example, grossing module 370 may be configured to receive barcode information, specimen description, specimen test plan information, and specimen cassette information, among others, and store such information to workflow database 160 linked to a current specimen. Data provided to grossing module 370 may be received on an automated basis from laboratory devices associated with grossing station 115 (e.g., a cassette printer), and/or from manual entry by personnel associated with grossing station 115 through workflow server via network 101, or other suitable method.

Further, grossing module 370 may be configured to provide information related to grossing station 115 in response to a request from workflow server 155 and/or analysis tool 300. For example, such information may include providing timestamp information for a specimen, a specimen cassette ID, and an operator ID. In some embodiments, grossing module 370 may be configured to provide additional processing of related information, such as summarizing and/or averaging data entry and cutting times, providing average success rates (e.g., per user), and average cost per error, among others, to analysis tool 300.

Sectioning module 375 may be configured to provide functionality associated with sectioning station 125. For example, sectioning module 375 may be configured to receive barcode information, sectioning timestamp data, specimen slide data (e.g., number of slides produced), and sectioning success information, among others, and store such information to workflow database 160 linked to a current specimen. Data provided to sectioning module 375 may be received on an automated basis from laboratory devices associated with sectioning station 125 (e.g., a microtome), and/or from manual entry by a technician at sectioning station 125 through workflow server via network 101, or other suitable method.

Further, sectioning module 375 may be configured to provide information related to sectioning station 125 in response to a request from workflow server 155 and/or analysis tool 300. For example, such information may include providing specimen sectioning timestamp information, the number of sections from a specimen, and sectioning success status at sectioning station 125. In some embodiments, sectioning module 375 may be configured to provide additional processing of related information, such as summarizing and/or averaging machine times.

Archiving module 380 may be configured to provide functionality associated with archiving station 150. For example, archiving module 380 may be configured to receive barcode information, timestamp information, and specimen information, and store such information to workflow database 160. Data provided to archiving module 380 may be received on an automated basis from laboratory devices associated with archiving station 150, and/or from manual entry by personnel associated with archiving station 150.

Further, archiving module 380 may be configured to provide information related to archiving station 150 in response to a request from workflow server 155 and/or analysis tool 300. For example, such information may include providing timestamp information and specimen location information.

Tissue processing module 385 may be configured to provide functionality associated with processing and embedding station 120. For example, tissue processing module 385 may be configured to receive barcode information, operator ID, timestamp information, storage cassette information, and dehydration time, among others, and store such information to workflow database 160 linked to a current specimen. Data provided to tissue processing module 385 may be received on an automated basis from laboratory devices associated with tissue processing and embedding station 120 (e.g., an automated dehydrator), and/or from manual entry by technicians associated with tissue processing and embedding station 120 by any suitable method.

Further, tissue processing module 385 may be configured to provide information related to tissue processing and embedding station 120 in response to a request from workflow server 155 and/or analysis tool 300. For example, such information may include providing timestamp information, embedding success rate, and operator ID at tissue processing and embedding station 120. In some embodiments, tissue processing module 385 may be configured to provide additional processing of related information, such as summarizing and/or averaging dehydrating machine times based on timestamps, determining average success rates, and breaking out possible critical points by highlighting errors associated with tissue processing and embedding tasks, among others.

Staining module 390 may be configured to provide functionality associated with H&E staining station 130, ISH staining station 133, IHC staining station 135, and special staining station 140, as well as any other staining stations that may be utilized by the physical laboratory. For example, staining module 390 may be configured to receive barcode information, operator ID, timestamp information, stains and reagents used, and the number of primary specimen output pieces stained, among others, and store such information to workflow database 160. Data provided to staining module 390 may be received on an automated basis from laboratory devices associated with H&E staining station 130, IHC staining station 135, and/or special staining station 140 (e.g., an automated stainer), and/or from manual entry by personnel associated with H&E staining station 130, IHC staining station 135, and/or special staining station 140.

Further, staining module 390 may be configured to provide information related to H&E staining station 130, IHC staining station 135, and/or special staining station 140—or other stainers present—in response to a request from workflow server 155 and/or analysis tool 300. For example, such information may include staining timestamp information, number of primary specimen output pieces stained, and staining success status, among others. In some embodiments, staining module 390 may be configured to provide additional processing of related information, such as summarizing and/or averaging staining times from individual stainers present, average batch size, number of batches, staining success rates, and other similar data.

Imaging module 395 may be configured to provide functionality associated with imaging station 145. For example, imaging module 395 may be configured to receive barcode information, specimen output piece data (e.g., number of slides per specimen), timestamp information, and imaging success status, and store such information to workflow database 160. Data provided to imaging module 395 may be received on an automated basis from laboratory devices associated with imaging station 145, and/or from manual entry by personnel associated with imaging station 145 through workflow server via network 101, or other suitable method.

Further, imaging module 395 may be configured to provide information related to imaging station 145 in response to a request from workflow server 155 and/or analysis tool 300. For example, such information may include providing specimen timestamp data at imaging station 145, imaging success status, and operator IDs. In some embodiments, imaging module 395 may be configured to provide additional processing of related information, such as summarizing and/or averaging imaging times per slide, imaging success rates, and identifying operator and imager errors, among other things.

Figure 4:
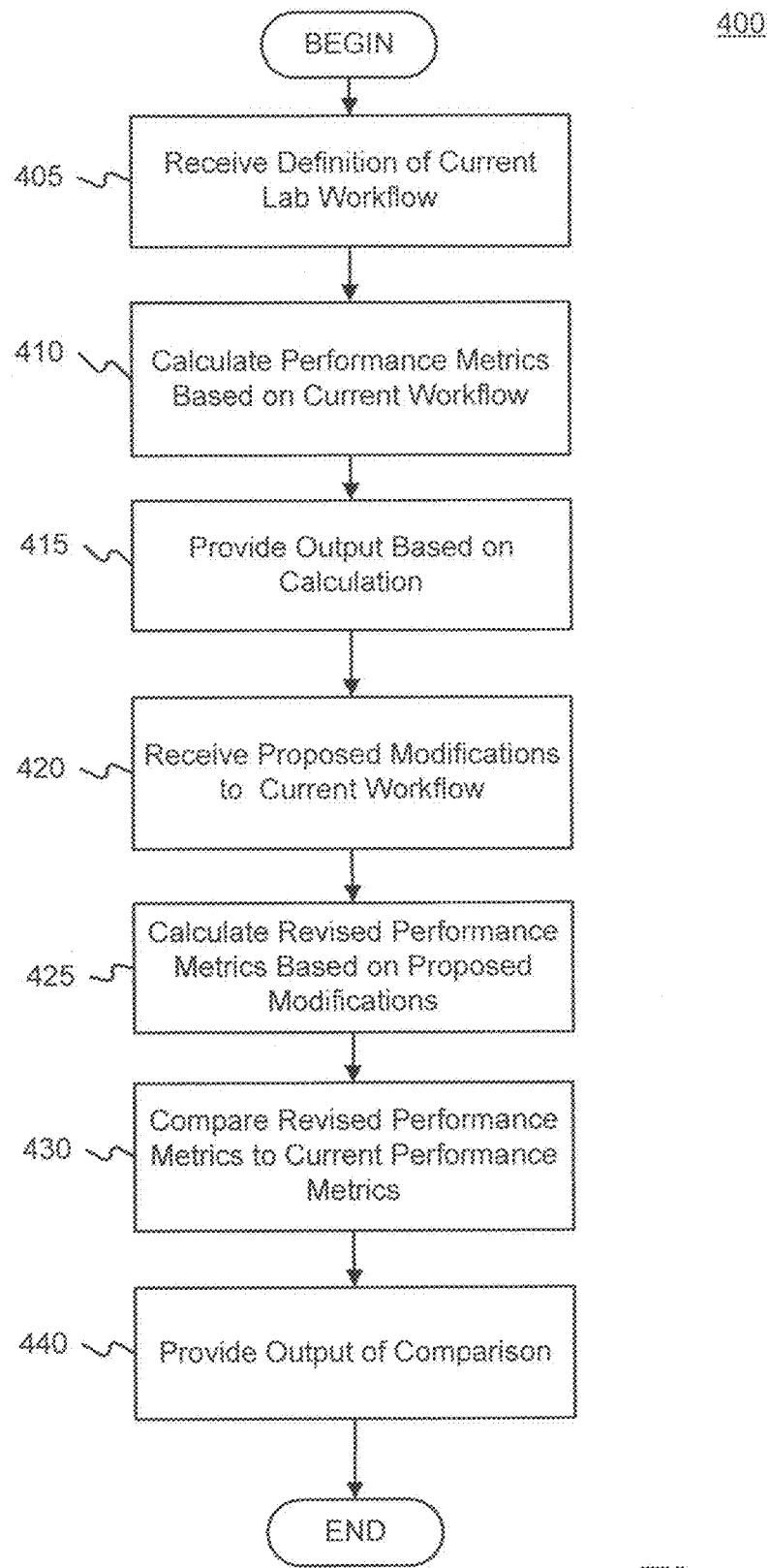
FIG. 4 is a block diagram of an exemplary method for analyzing performance data associated with existing and prospective workflows associated with a pathology laboratory.
Figure 9A:
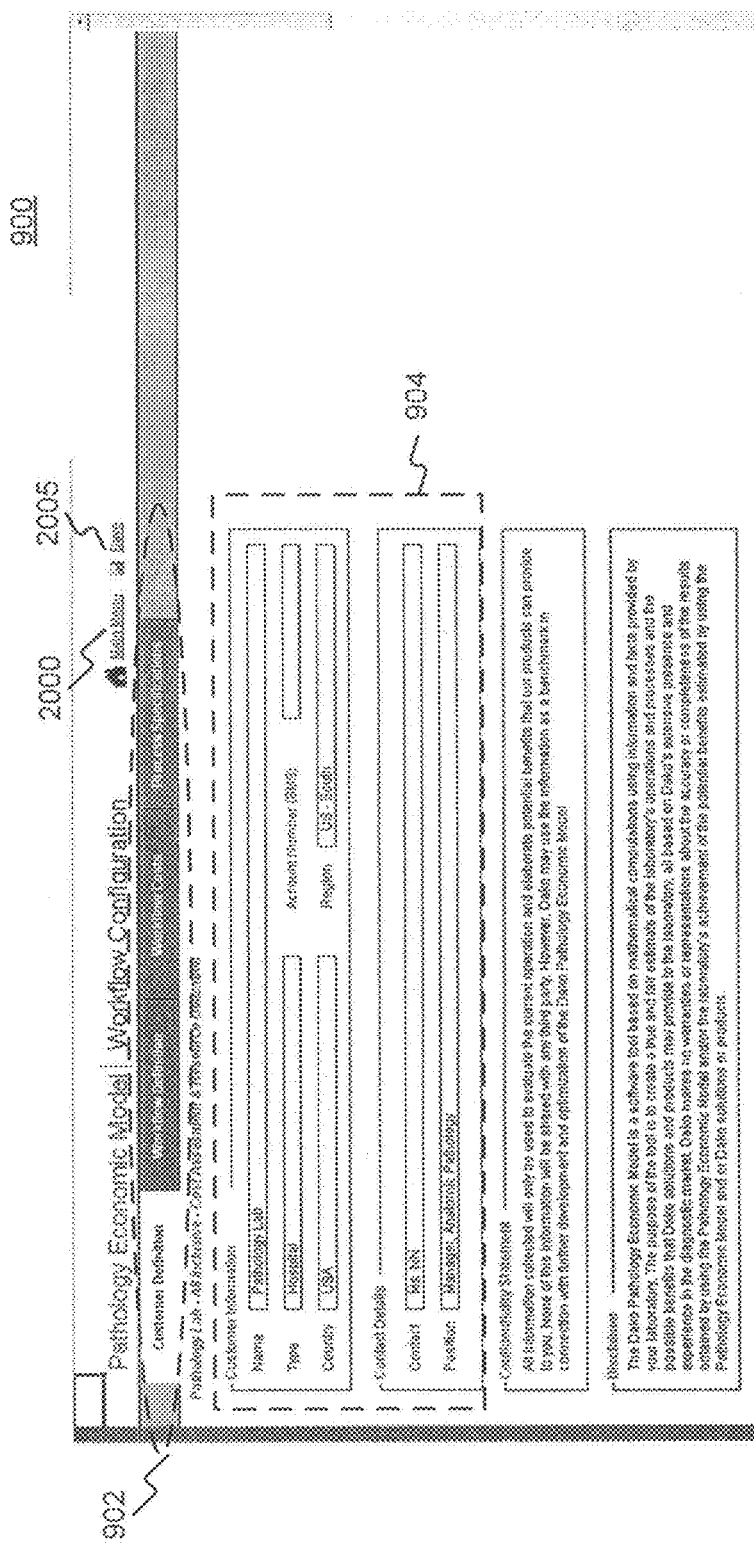
FIG. 9A is an exemplary depiction of a customer definition section of an interface enabling user definition of an existing workflow.

FIG. 4 is a block diagram of an exemplary method for analyzing performance data associated with existing and prospective workflows associated with a pathology laboratory. Upon executing analysis tool 300 for analyzing a workflow associated with a pathology lab, a user may be provided a first interface for entering a set of parameters associated with an existing workflow in the pathology laboratory (e.g., via GUI module 305) (step 405). Such parameters may include identifiers associated with the pathology laboratory, a workflow process and a workflow scale, among other things. FIGS. 9A-9J will be used to describe exemplary embodiments of a first interface for defining a pathology lab workflow. Such interfaces may be generated by PEM interface module 315, presentation generator module 335, control module 310, and GUI module 305, among others. FIG. 9A shows an exemplary depiction of a first interface 900 with a customer definition section 904 of an interface enabling user definition of an existing workflow. First interface 900 may provide a series of navigation tabs 902, a return control 2000, a save control 2005, and/or other controls for purposes of navigating, inputting, saving, and displaying data. Return control 2000 may enable a user to leave first interface 900 and return to an introduction screen or other suitable location provided by an analysis tool. Save control 2005 may enable a user to save the current data to a local hard drive, network server, or other suitable location (e.g., flash memory drive) for future access.

Navigation tabs 902 may include one or more tabs configured to enable a user to navigate through various sections of first interface 900 by clicking or otherwise actuating any of the associated tabs. For example, navigations tabs 902 may include a customer definition tab, a workflow definition tab, a workflow cost tab, and a process specification tab, each configured to display a particular section of first interface 900.

Upon clicking or otherwise actuating one of the tabs, GUI module 305 and control module 310, among others, may cause a user to be provided a particular section of first interface 900 consistent with the tab title. One of ordinary skill in the art will recognize that more or fewer tabs may be provided by first interface 900 and sections of first interface 900 may be broken out or combined as desired.

Customer definition section 904 may include a series of controls for purposes of receiving input and displaying data related to identifying information for a workflow associated with a particular lab. The terms "control" or "controls," as used herein, shall mean any graphical control used for receiving and/or displaying input, including but not limited to, button controls, textbox controls, radio button controls, checkbox controls, dropdown controls, list box controls, tab controls, hyperlink controls, chart controls, and any other suitable controls. Such controls may be provided via PEM interface module 315, presentation generator module 335, GUI module 305, or any other suitable module. For example, a series of textboxes may be provided via presentation generator module 335, which may allow entry of a customer name, a customer type (e.g., hospital lab), and various other information (e.g., contact information), among others. Such data may be useful when preparing a visit to a client site or for identifying for whom a particular workflow model has been prepared.

Figure 9B:
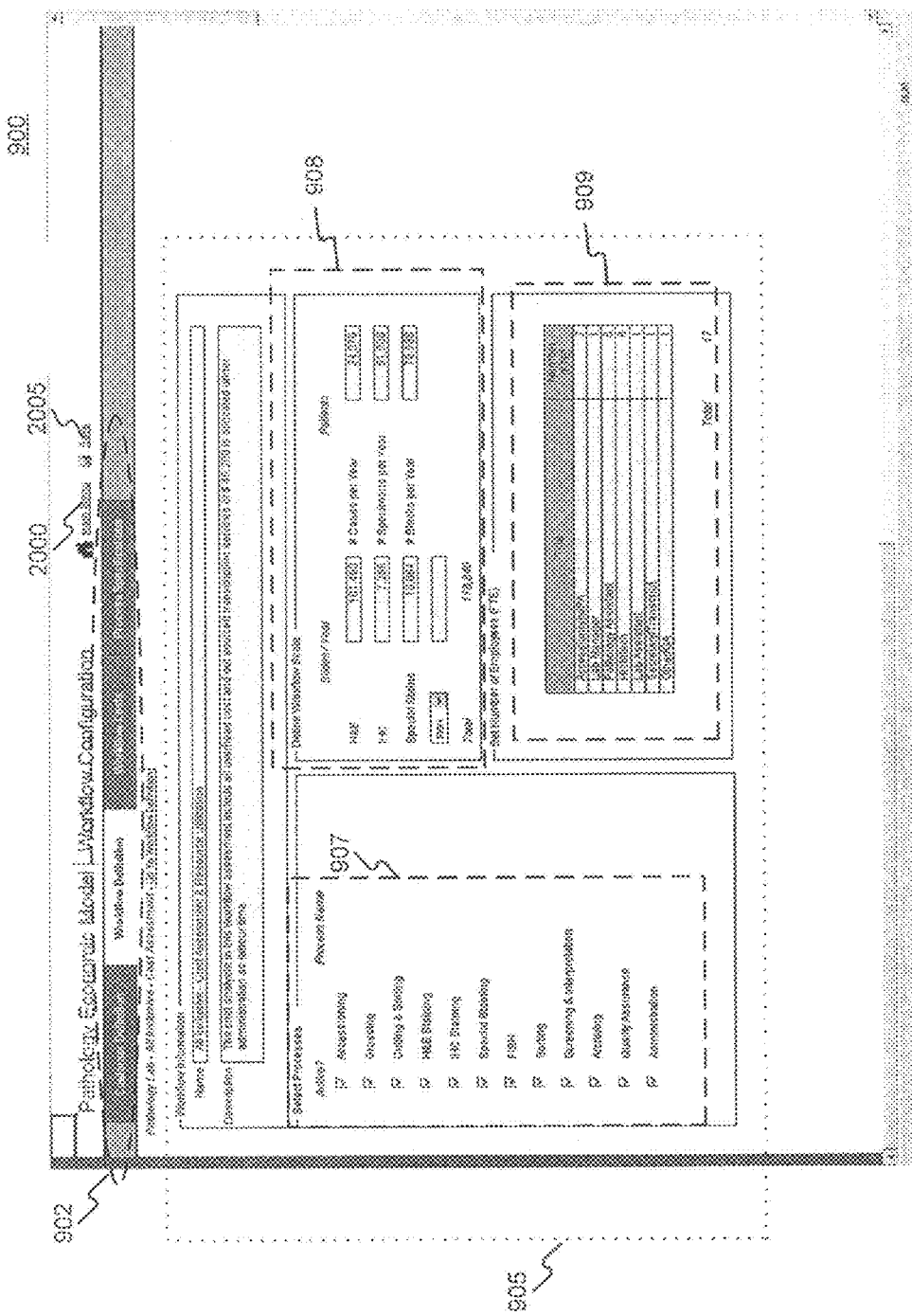
FIG. 9B is an exemplary depiction of a workflow definition section of an interface enabling user definition of an existing workflow.

FIG. 9B shows an exemplary depiction of a workflow definition section 905 of an interface enabling user definition of an existing workflow. Workflow definition section 905 may be displayed upon a user clicking workflow definition tab or other related navigation tab from within navigation tabs 902, or by any other suitable method. Workflow definition section 905 may be configured to enable entry and display of a workflow process and a workflow scale, among other things. Workflow definition section 905 may include workflow process controls 907 and workflow scale selectors 908, as well as any other desired controls (e.g., employee information controls 909). Workflow process controls 907 may include one or more controls configured to allow selection of one or more workflow processes. For example, a series of checkboxes may be provided, each labeled with an identifier indicating one or more of the workflow processes described above (e.g., accessioning, grossing, H&E staining, imaging, administration, etc.). By selecting (e.g., checking) particular checkboxes within workflow process controls 907, a user may define workflow processes included in a physical pathology laboratory that the user desires to model. One of ordinary skill in the art will recognize that other controls and/or other processes may be included within workflow process controls 907 without departing from the scope of the present disclosure.

Workflow scale controls 908 may be configured to receive and display data related to a workflow scale associated with a pathology lab and may include one or more controls (e.g., text box controls) configured to receive related parameters. Workflow scale may include a number of cases through the lab per unit time, a number of primary specimen output pieces from H&E staining station 130 per unit time, a number of primary specimen output pieces from IHC staining 135 per unit time, a number of primary specimen output pieces from special staining 140 per unit time, number of primary specimen output pieces from ISH staining 133 per unit time, and a number of tissue blocks per unit time. One of ordinary skill in the art will recognize that workflow scale may also include additional parameters, such as, for example, number of specimens received in the lab per unit time, without departing from the scope of the present disclosure.

In some embodiments, the unit of time for workflow scale may be one year. One of ordinary skill in the art will recognize that a longer (e.g., two years) or a shorter (e.g., one month) unit of time may be utilized for determining and inputting of workflow scale.

Employee information controls 909 may enable the input and display of data related to employees of the lab. Employee information controls 909 may include one or more text box controls, drop down controls, and/or other suitable controls to enable entry and display of such information. For example, a lab may employ one or more lab managers, one or more histotechs, assistants, secretaries, etc. Each of these employees may work full or part time. Therefore, the number of "Full Time Equivalents" for each type of these employees may be documented during workflow definition using employee information controls 909 to provide additional detail for modeling the workflow of the pathology laboratory.

Figure 9C:
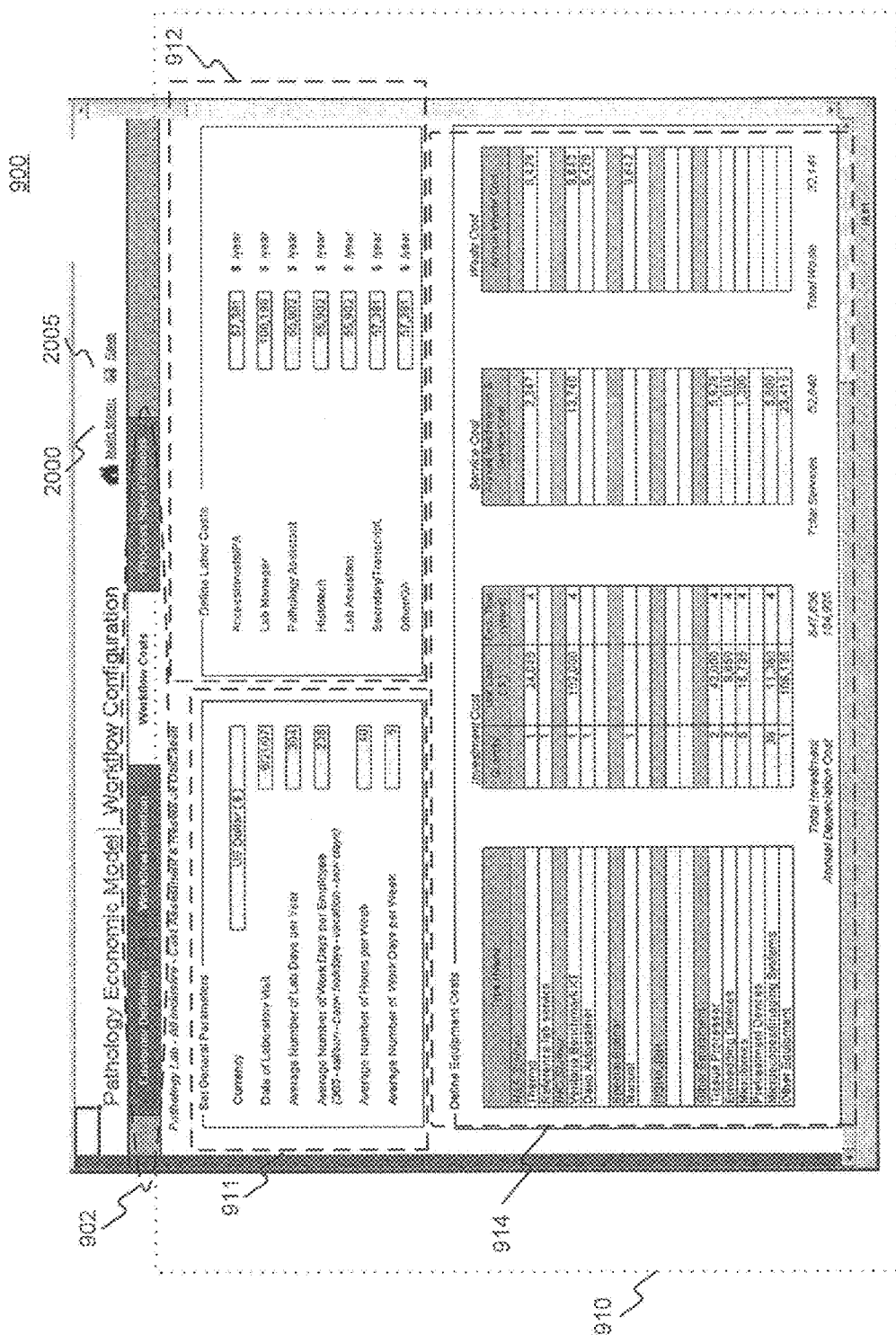
FIG. 9C is an exemplary depiction of a first portion of a workflow costs section of an interface enabling user definition of an existing workflow.
Figure 9D:
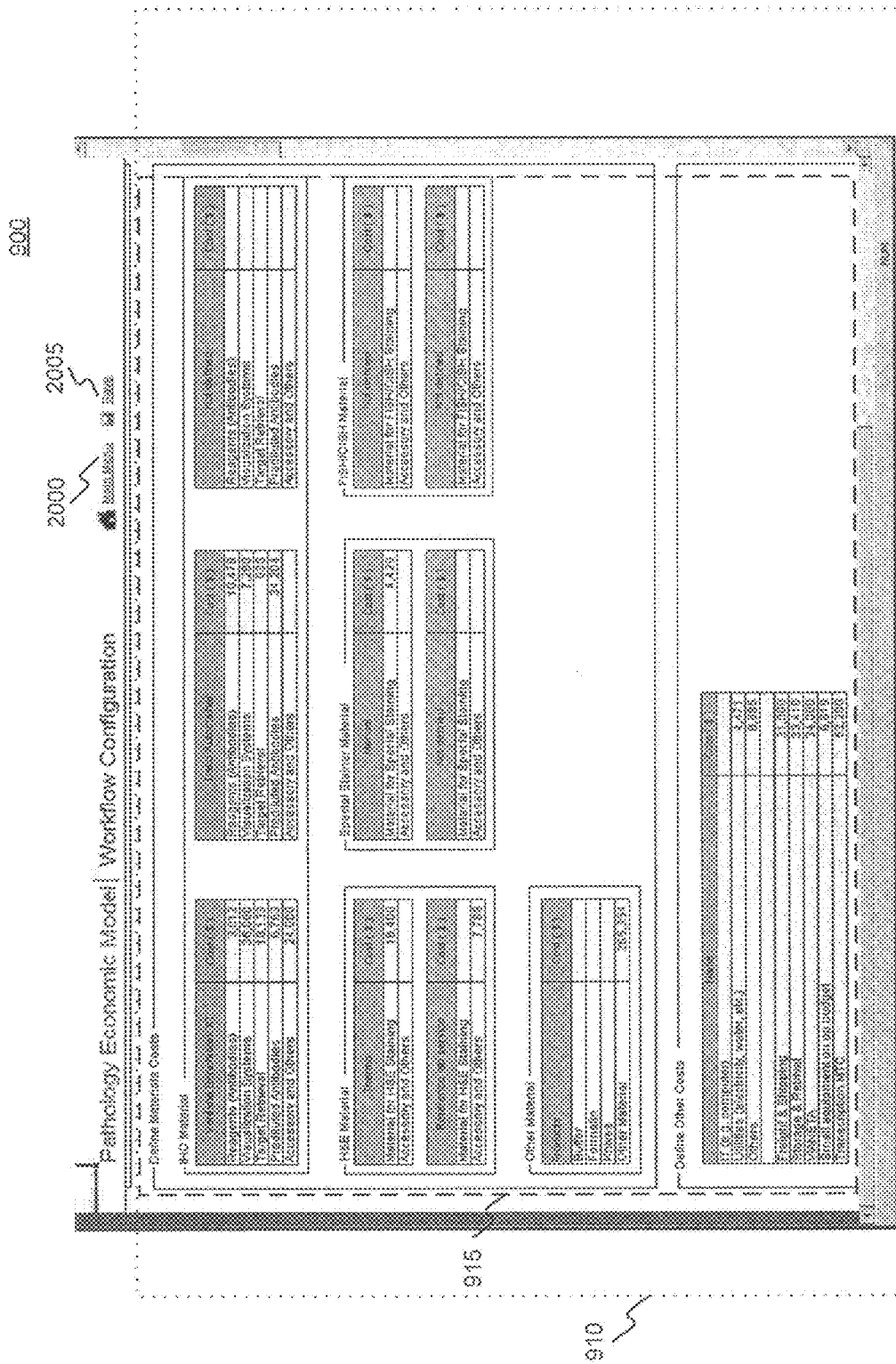
FIG. 9D is an exemplary depiction of a second portion of a workflow costs section of an interface enabling user definition of an existing workflow.
Figure 9E:
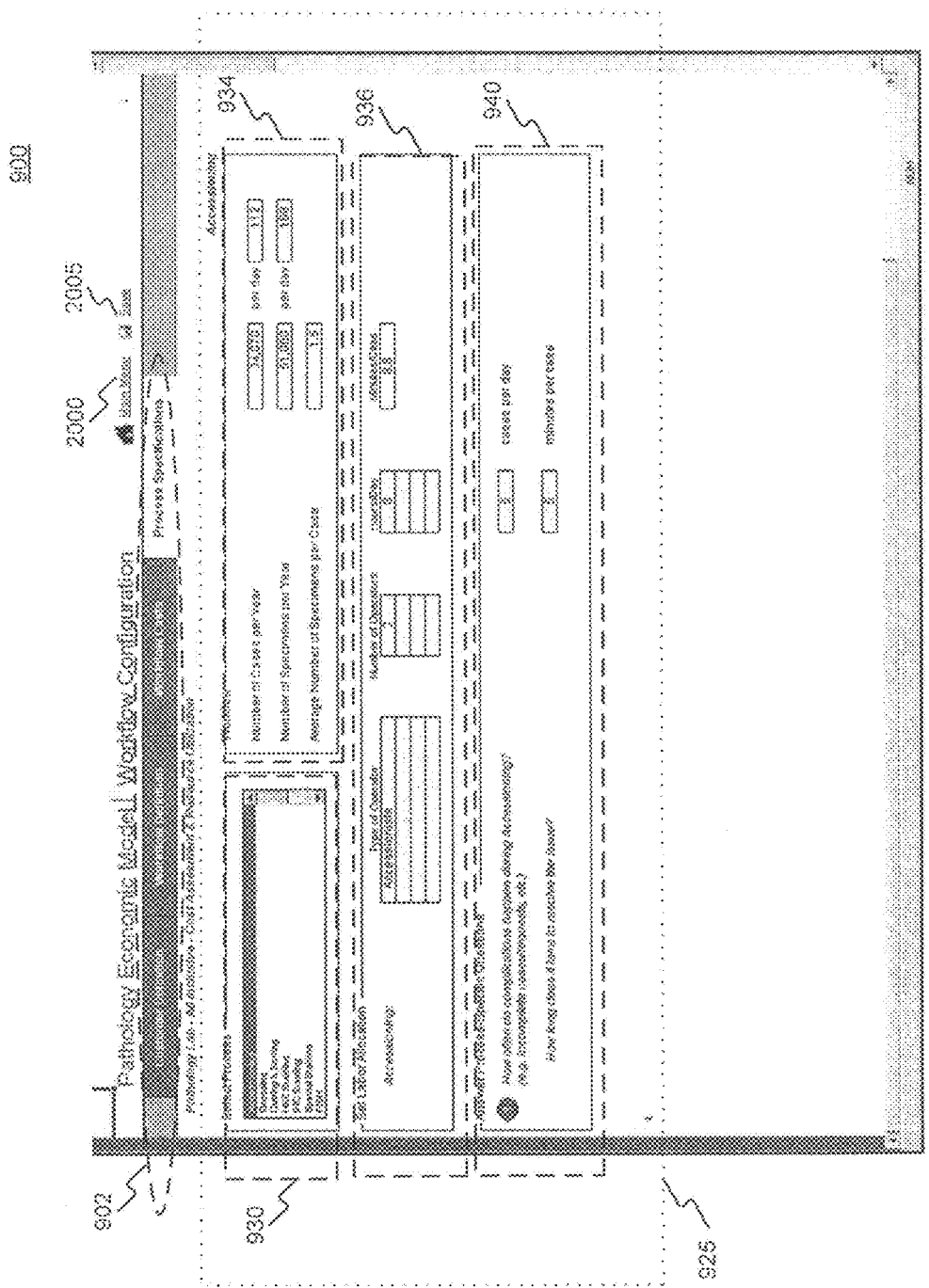
FIG. 9E is an exemplary depiction of a process specification section highlighting setup of the accessioning process of an interface enabling user definition of an existing workflow.
Figure 9F:
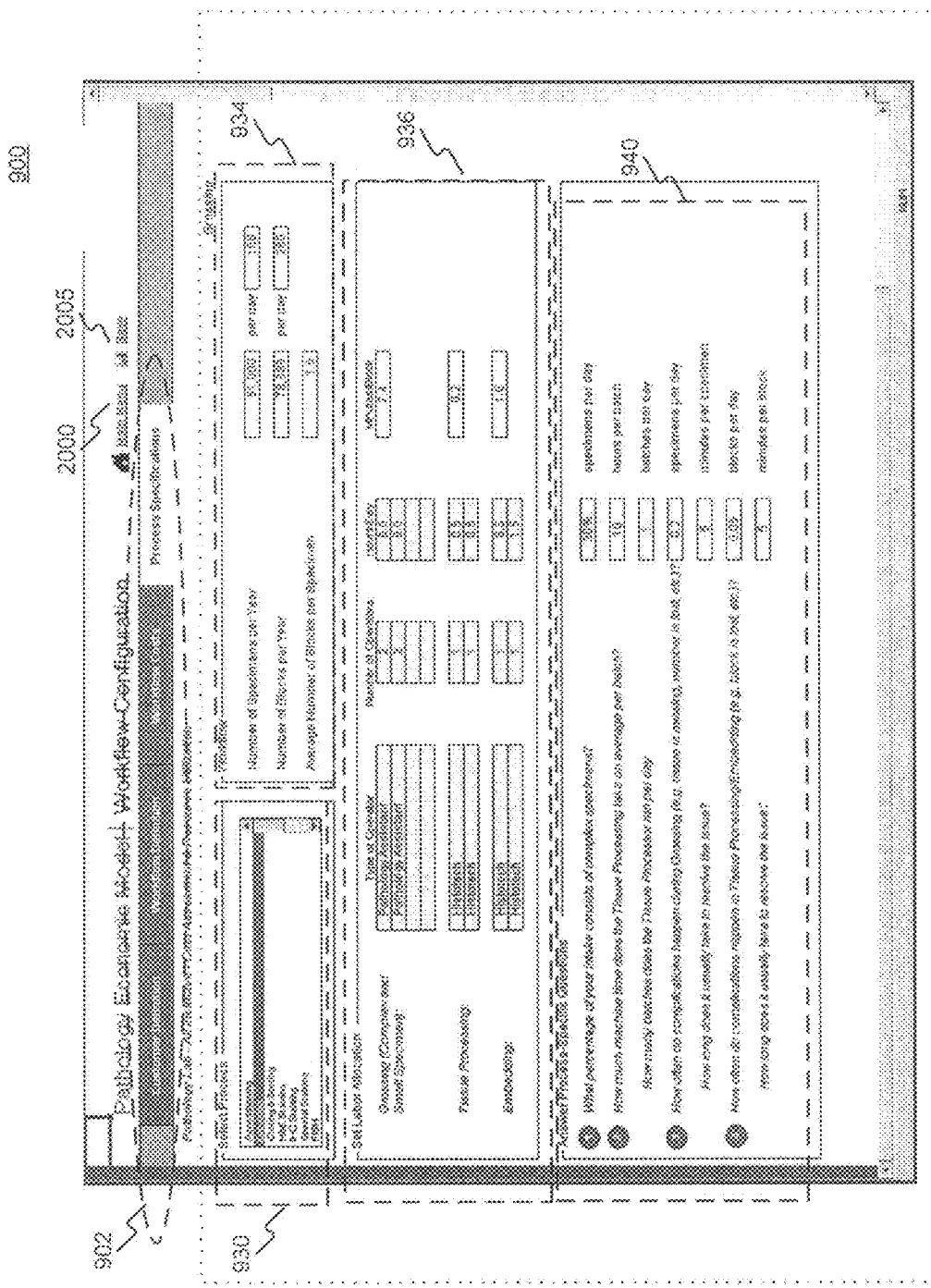
FIG. 9F is an exemplary depiction of a process specification section highlighting setup of the grossing process of an interface enabling user definition of an existing workflow.

FIG. 9C is an exemplary depiction of a first portion of a related expenses section of an interface enabling user definition of an existing workflow while FIG. 9D is a second portion of the workflow costs section. Workflow cost section 910 may be accessed by a user clicking on a workflow cost tab within navigation tabs 902, or by any suitable method. Workflow cost section 910 may be configured to receive and display data related to associated costs of a current workflow and may include general cost definition controls 911, labor cost controls 912, equipment cost controls 914, and materials/consumables cost controls 915. General cost definition controls 911 may provide controls (e.g., text box controls) that enable a user to input and review a general configuration associated with the costs for a pathology lab workflow. For example, general cost definition controls 911 may include one or more text boxes enabling input of a national currency used by a pathology lab (e.g., Euro, U.S. dollar, etc.), the average days in operation per unit time for the lab, an average number of workdays for employees of the lab, hours per week, and workdays per week. One of skill in the art will recognize that more or fewer controls may be provided based on the desired level of detail for general cost definition.

Labor cost controls 912 may provide controls (e.g., text box controls) that enable a user to input and review costs associated with the employee labor defined by employee information controls 909. For example, for each employee class (e.g., histotech, pathologist, accessionist, etc.) defined in employee information controls 909, a text box control may be displayed within labor cost controls 912 for purposes of inputting and reviewing salary or other cost information associated with the employee class. For example, in a lab with ten histotech employees, the average salary per histotech may be provided to labor cost controls 912. Alternatively, it may be possible to provide salary on a per employee basis as desired.

Equipment cost controls 914 may provide controls (e.g., tables, text box controls, etc.) that enable a user to input and review costs associated with equipment present in the current pathology lab workflow. For example, as described above, a lab may include various pieces of equipment (e.g., autostainer, microtome, etc.) utilized at different stations within the lab. Each of these pieces of equipment may be documented within equipment cost controls 914 and an investment cost, service cost, and waste cost, among others, assigned. In some embodiments, investment cost, service cost, and waste cost may be empirically determined and stored within analysis tool 300 for a variety of lab devices currently available in the market. For example, equipment cost controls 914 may include a dropdown control including a list of autostainers available in the market. Upon a user selecting one of the autostainers, equipment cost, service cost, and waste cost may all be auto populated based on information stored with analysis tool 300. In addition, by defining equipment in equipment costs controls 914, parameters associated with such equipment may be provided to the tool enabling precision of the tool to be enhanced. For example, by specifying a particular model of autostainer, capacity information may become available to analysis tool 300 based on publicly available specifications associated with the specified autostainer. Alternatively, a lab manager or other employee of the lab may edit and/or specify such information based on data obtained over the course of lab operations for the lab currently being modeled.

Materials/consumables cost controls 915 may provide controls (e.g., tables, text box controls, etc.) that enable a user to input and review costs associated with materials and consumables utilized in various processes of the current pathology lab workflow. For example, each staining process within staining stations 132 (e.g., IHC staining 135, H&E staining 130, ISH staining 133, and special staining 140) may each utilize different reagents, antibodies, accessories, and other consumable materials depending on the particular staining station. Costs for the consumables utilized at each of the staining stations may be entered and reviewed in materials/consumables cost controls 915. Such entry may be performed via one or more text boxes or other suitable controls. Further, costs may be combined into one number based on all materials utilized at each individual staining station, or based on a desired level of precision, broken out by the various consumable products and materials utilized at each individual station. In addition, consumable items that are common across staining stations 132 (e.g., formaldehyde, knives, buffers, etc.).

One of ordinary skill in the art will recognize that more or fewer costs may be received through workflow cost section 910 without departing from the scope of the present disclosure. For example, various other costs associated with operation of a lab may be tracked, including, infrastructure costs (e.g., utilities, rent, etc.), IT costs (e.g., computer support), and general shipping costs. Costs shown in FIGS. 9C and 9D are exemplary only.

FIGS. 9E-J show exemplary process specification section 925 of first interface 900. Process specification section 925 may be accessed by a user clicking on a process specification tab within navigation tabs 902, or by any suitable method. Process specification section 925 may enable a user to specify parameters associated with each workflow process previously specified via workflow process controls 907. For example where a user has indicated the presence of accessioning, grossing, sectioning, and H&E staining processes, such processes may be provided to the user via process selector control 930. Process selector control 930 may be a list box control, a drop down control, a radio button control, or any other suitable control. In some embodiments, a list box control may be used for process selector control 930 which may enable a user to select each workflow process currently defined through workflow process controls 907.

Upon selecting a particular workflow process available within process selector control 930, additional controls may become available within process specification section 925. Such controls may include, for example, process scale controls 934, process labor allocation controls 936, process specific device controls 938, and process specific question controls 940. Process scale controls 934 may enable a user to enter and review data related to workflow scale based on the selected process in process selector control 930. Similar to workflow scale defined with regard to FIG. 9B, workflow scale for a particular process may include, among others, a number of cases per unit of time, and/or multiple units of time (e.g., per year and per day), a number of output pieces per the specific station per unit time, an average number of specimens per case, and an average number of input pieces to the station (i.e., the output piece from a previous station in the workflow). A user may input the workflow scale data related to the specific workflow processes via one or more controls (e.g., textboxes available within process scale controls 934).

Process labor allocation controls 936 may be configured to allow a user to allocate labor associated with the workflow process selected within process selector controls 930 and the one or more employees defined via employee information controls 909. Depending on the selection within process selector controls 930, process labor allocation controls 936 may change to display desired labor categories. For example, where the grossing process is selected in process selector controls 930, a user may be allowed to assign a number of employees and their associated labor time for grossing, processing, and embedding processes. Such an assignment may be enabled by dropdown controls, list box controls, or any other suitable controls. In addition, textbox controls may be used for manual entry of labor time and other parameters. One of ordinary skill in the art will recognize that more or fewer data entry points may be provided depending on the needs of a particular lab.

Figure 9G:
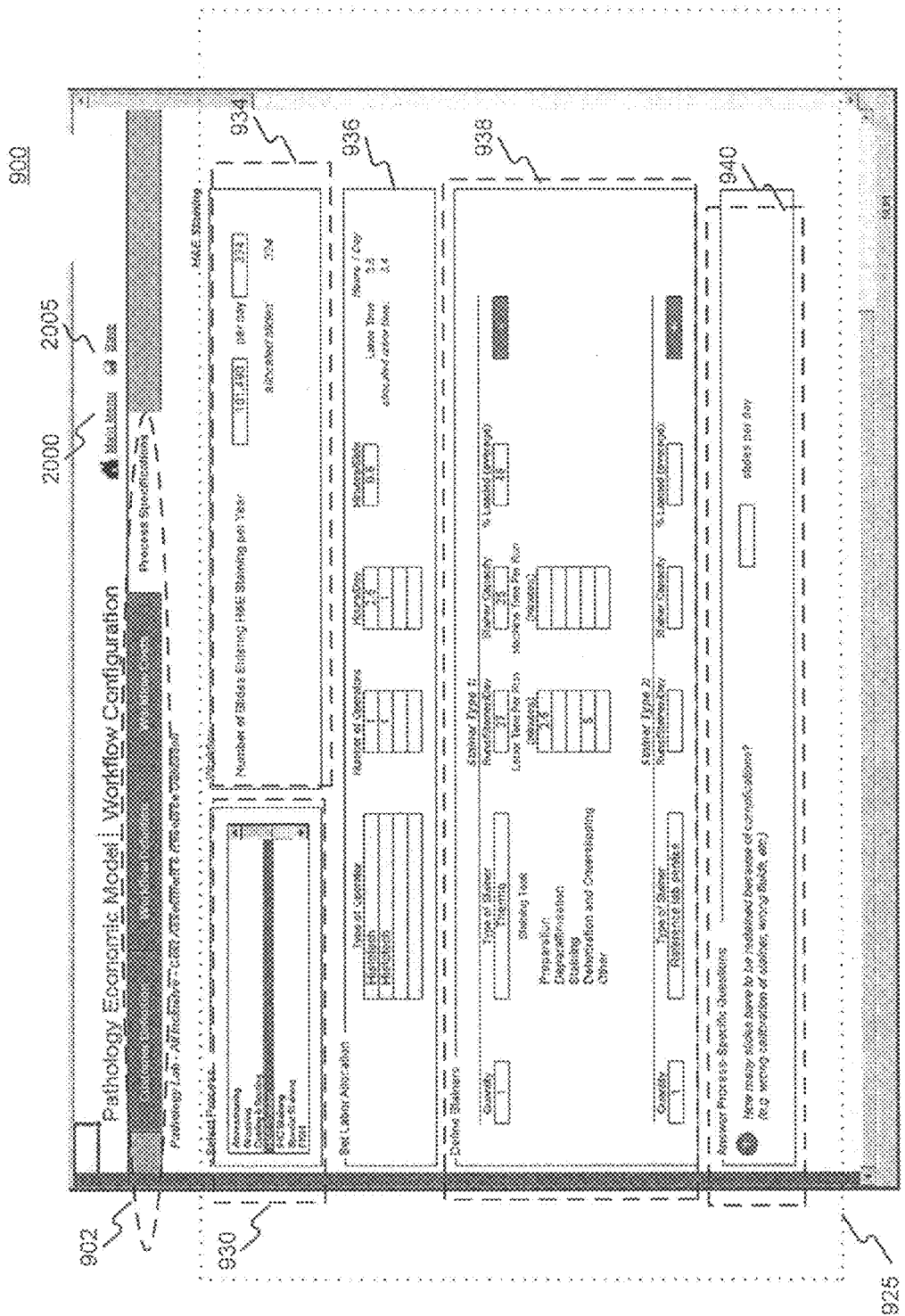
FIG. 9G is an exemplary depiction of a process specification section highlighting setup of the H&E staining process of an interface enabling user definition of an existing workflow.
Figure 9H:
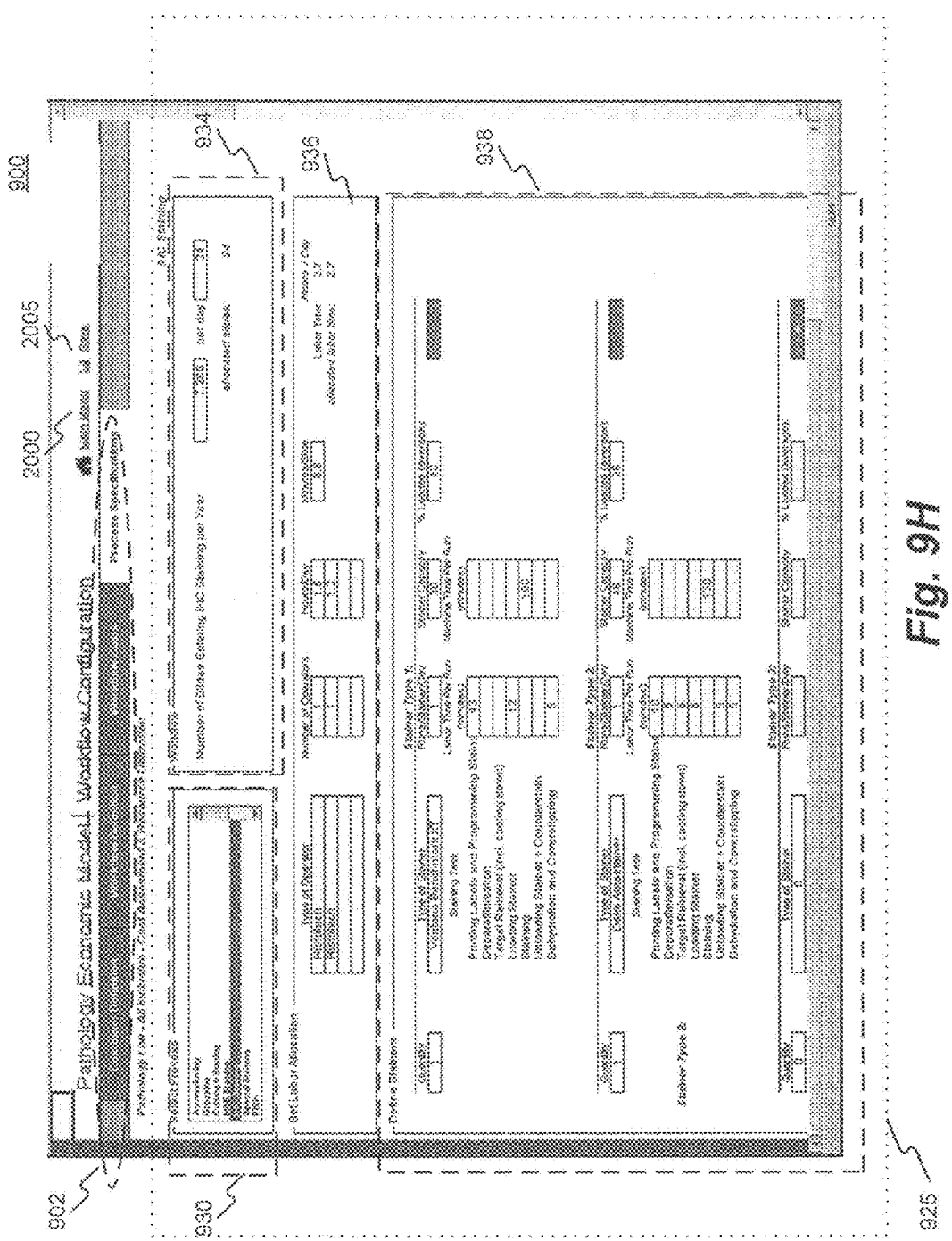
FIG. 9H is an exemplary depiction of a process specification section highlighting setup of the IHC staining process of an interface enabling user definition of an existing workflow.
Figure 9I:
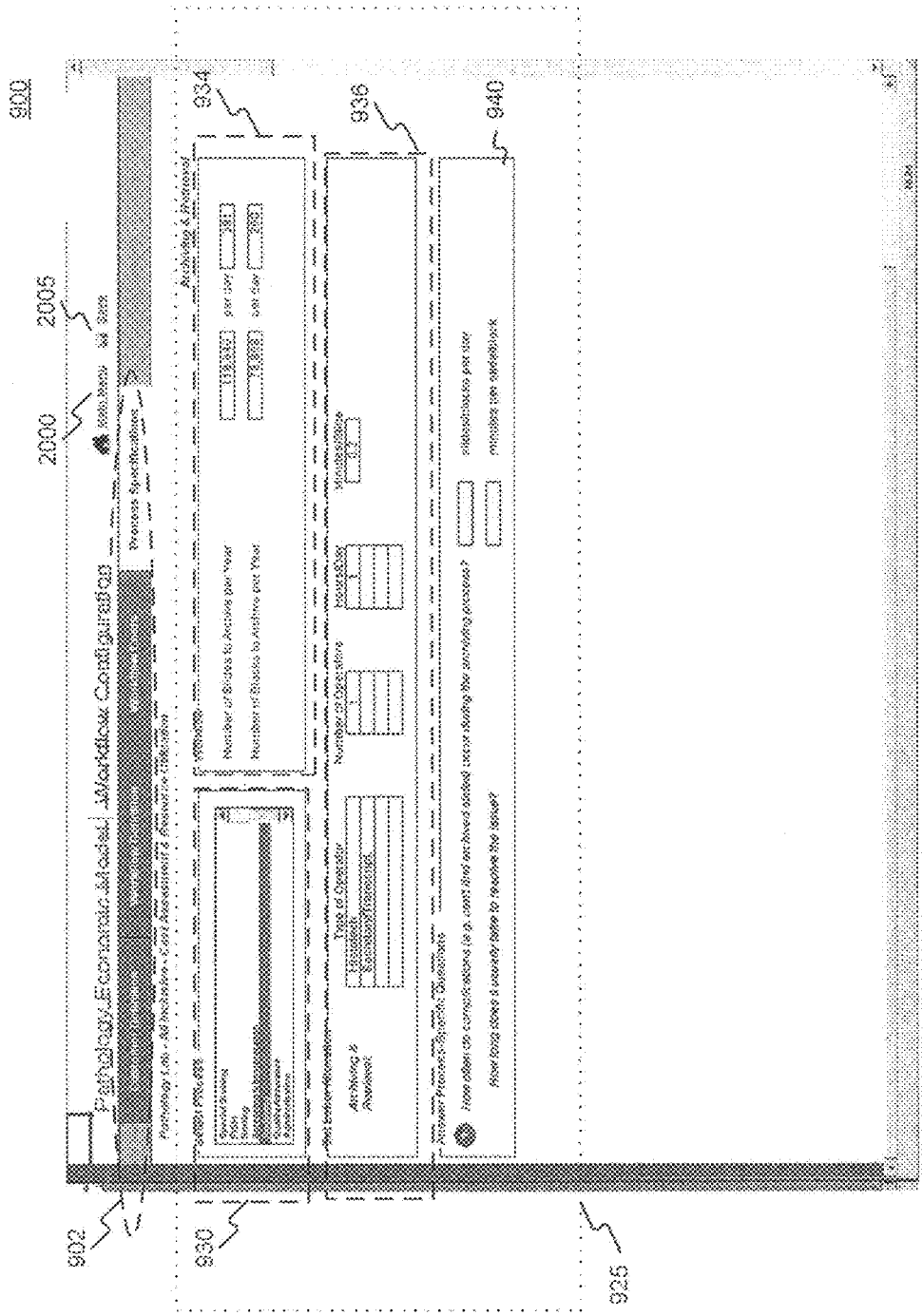
FIG. 9I is an exemplary depiction of a process specification section highlighting setup of the archiving process of an interface enabling user definition of an existing workflow.
Figure 9J:
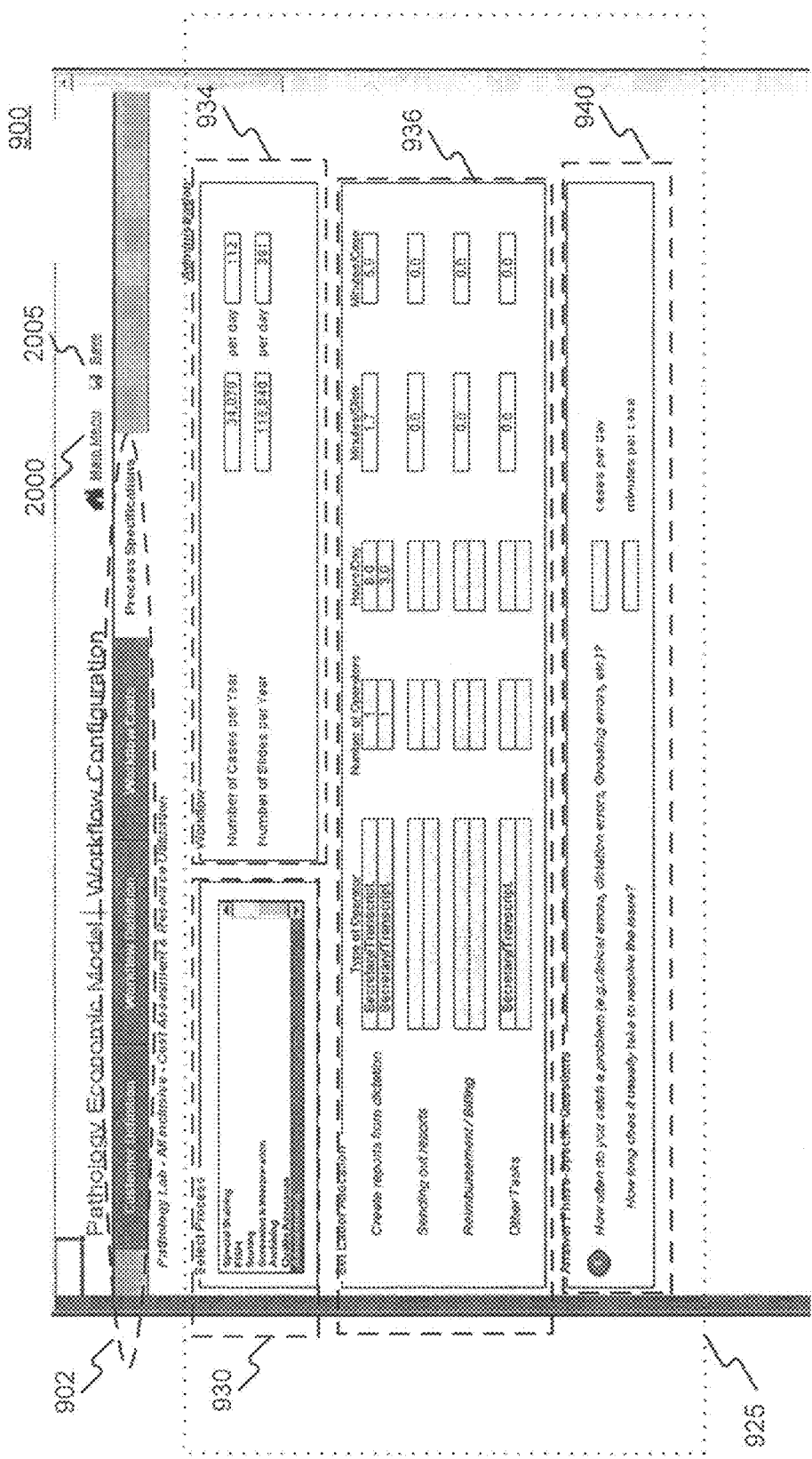
FIG. 9J is an exemplary depiction of a process specification section highlighting setup of the administration process of an interface enabling user definition of an existing workflow.

As shown in FIGS. 9G and 9H, process specific device controls 938 may enable a user to provide specific information about one or more laboratory devices present within the workflow being defined. For example, one or more stainers may be present within the workflow and, therefore, a user may provide information such as the number of runs per day, stainer capacity, and percent loaded, among other things. In some embodiments, information related to a stainer may be known based on commonly available product specifications and may be auto populated by analysis tool 300. Alternatively, a user may edit and/or manually provide such information. While the example of a stainer was used to describe process specific device controls 938, one of ordinary skill in the art will recognize that other devices (e.g., microtomes, imaging devices, etc.) may also be customized and described via process specific device controls 938.

Process specific question controls 940 may enable a user to input various additional data that may be helpful for improving precision associated with analysis tool 300. Each process selected within process selector control 930 may include a different series of process specific questions that may be displayed and answered within process specific question controls 940. For example, upon selection of a grossing process within process selector control 930, process specific question controls 940 may provide a list of questions including, a percentage of complex specimens, machine time associated with tissue processing, and frequency of complications at the grossing station. As noted, such questions may vary by process and the questions highlighted herein are intended to be exemplary only. Any process specific questions which may assist analysis tool 300 or a user of analysis tool 300 in making workflow based determinations may be implemented.

Once the current workflow has been defined within first interface 900, analysis tool 300 may calculate performance data associated with the modeled pathology lab workflow (step 410). Such performance data may include current cost information, current time utilization, current success rate, and current error cost, among other things. For example, current cost information may be provided as a cost per specimen output piece (e.g., a slide, a specimen cassette, etc.).

Figure 5:
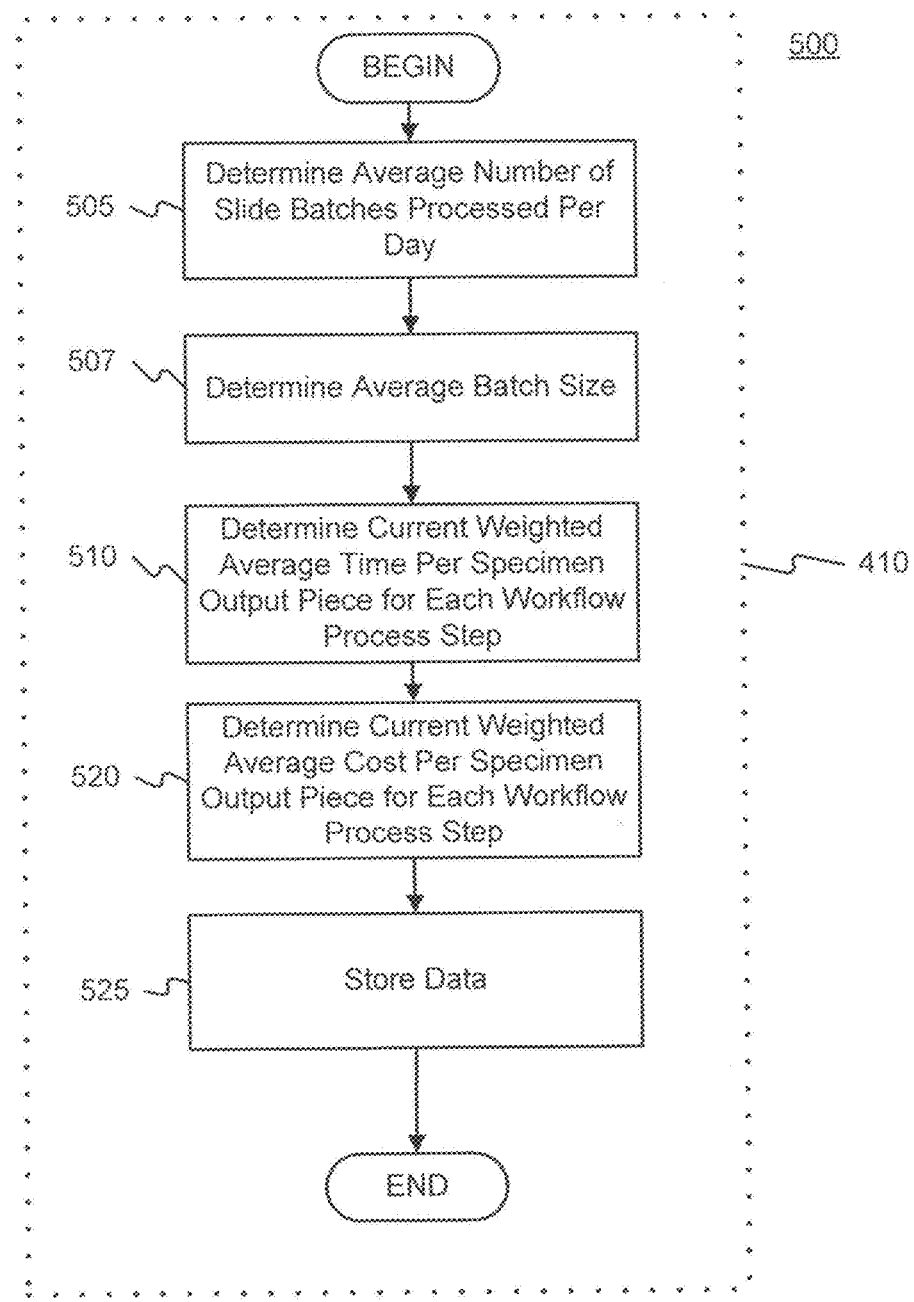
FIG. 5 is a block diagram showing an exemplary method for accurately determining performance data associated with an existing workflow.

FIG. 5 is a block diagram showing an exemplary method for accurately determining performance data associated with an existing workflow as shown at step 410. Current performance data may be calculated via PEM calculation module 320 following return of data from data module 330, database module 345, and/or control module 310, among others.

The following Table 1 may be referenced throughout the following discussion for purposes of clarity. The values included in Table 1 are provided for example only and are not intended to be limiting.

TABLE 1

Exemplary Workflow Values

| | |
|---|---:|
| H&E Output Pieces/year | 101,000 |
| IHC Output Pieces/year | 7,200 |
| Special Stain Output Pieces/year | 10,000 |
| ISH Output Pieces/year | 500 |
| Cases/year | 34,000 |
| Specimens/year | 51,000 |
| Blocks/year | 79,000 |
| Histotech Salary/year | $55,000 |
| Histotech Hours Embedding | 6.5 |
| Histotech Hours Staining Setup | 1.5 |
| Accessionist Salary | $57,000 |
| Accessionist Hours in Accessioning | 8.0 |
| Lab Days/year | 240 |

Because staining is generally performed in "batches" (i.e., collections of output pieces processed simultaneously), stainer cost allocation may be illustrated based on a per batch and/or per output piece basis, among others. Therefore, analysis tool 300 may first determine an average number of batches processed per day through each staining station within staining stations 132 based on the currently modeled workflow (step 505). Calculation of the average number of batches per stainer per day may be based on the workflow scale defined in workflow scale controls 908 and workflow devices defined in equipment cost controls 914 (e.g., stainers). For example, the average number of batches per day for IHC staining station 135 may calculated based on the number of primary specimen output pieces processed at H&E staining station 135 per year, the number of days the lab was in operation for the year, and the capacity of stainers available at IHC staining station 135. The number of batches per staining station per day can be approximated based on the known stainer capacity and the number of slides per staining station per day. For example, the number of slides processed per day at IHC staining station 135 may be 30 based on exemplary data in Table 1. Two stainers may be present at IHC staining station 135, each with a capacity of 28 slides. Therefore, because neither stainer is configured to run 30 slides, the average number of slide batches processed per day may equal 2.

Analysis tool 300 may then calculate an average batch size associated with each stainer (step 507). A "load factor" may be utilized for determining the average batch size and average loading of each stainer. Calculations may be based on the capacity of each stainer within a staining station and the number of slides processed per day. For example, based on the data in Table 1, an average of 30 slides per day (7,200 slides/240 lab days) may be processed by IHC staining station 135, which, for example, may include two or more stainers. As discussed, the exemplary stainers may each have a 28 slide capacity and therefore would process 15 slides each per day (i.e., to make 30 slides). Therefore, where both stainers are in operation, a load factor of approximately 53.5 percent may be assumed for each of the available stainers, resulting in an average batch size of 15 slides. In other words, each stainer can be assumed to run 1 batch at 53.5 percent of full capacity.

One of ordinary skill in the art will recognize that various average batch sizes and load factors may be utilized depending on a particular workflow configuration and operator habits, among others, without departing from the scope of the present disclosure. For example, different load factors may be assigned to each of one or more stainers assigned to a staining station to more closely approximate the actual use of a particular stainer.

Once batch information has been determined, analysis tool 300 may determine average weighted time and cost per primary and other specimen output pieces within the lab process (steps 510 and 520). The weighted average costs may be determined for each of the lab stations individually, or, alternatively, one or more of the lab stations may be grouped together depending on the workflow configuration. Determinations may be made based on the information provided during workflow configuration, such as the workflow costs and process specification sections.

Returning to Table 1 for exemplary data, during process specification, a user may indicate that one full time equivalent of a histotech operates at tissue processing and embedding station 120, and spends 6.5 hours per day embedding specimens. A salary of $55,000/year may also have been provided for the full time equivalent histotech during workflow configuration and labor cost controls 912. Therefore, the labor costs associated with the embedding process may be allocated by determining the fraction of the full time equivalent histotech's daily salary allocated to the 6.5 hours spent embedding. For example, where 6.5 hours associated with a full time equivalent histotech are allocated to embedding tissue 240 full time days per year, and at a full time equivalent salary of $55,000/year, a daily labor cost of approximately $187 for embedding results. Therefore, a total daily average specimen output piece (e.g., slides) from staining stations 132 is based on the output pieces in table 1 above (i.e., 118,700) equals the yearly total divided by days in operation, or approximately 494 slides/day. Dividing the $187 daily embedding cost by the number of daily slides yields a daily embedding cost per staining process output piece of 38 cents. Additionally, it may be desired to calculate the cost per tissue processing process output piece (e.g., blocks). Therefore, the number of yearly blocks (e.g., 79,000) divided by the number of lab days (e.g., 240) results in 329 blocks per day. Thus, an average daily labor cost per block at tissue processing and embedding station 120 is approximately equal to 57 cents. One of ordinary skill in the art will recognize that similar calculations and allocations may be made for any of the pre-staining and post-staining processes 215 and 219.

Additionally, consumable costs for consumables utilized (e.g., knives, formaldehyde, etc.) at pre- and post-stain lab stations 215 and 219 may be allocated to a staining station output piece based on similar calculations to those described with regard to labor determinations. Consumable costs for pre- and post-stain lab stations 215 and 219 may be determined and allocated on a station-by-station basis (i.e., only consumables used in a particular pre- or post-stain lab station are allocated to that lab station) and/or may be determined and allocated on a laboratory basis (i.e., all consumables except for staining consumables rolled up and allocated across all staining output pieces). One of ordinary skill in the art will understand that each station may have its associated labor allocated in a similar fashion to that describe above.

Average cost per specimen output piece associated with staining processes 232 at staining stations 132, may be determined similarly to the methods described above; however, for purposes of providing a weighted average cost and time per primary specimen output piece, the costs (e.g., labor costs, consumable costs, machine costs, service costs, etc.) may be allocated only to those slides processed in a particular staining station 132. This may improve accuracy of a performance analysis and mitigate the need to track detailed activities at each station, because costs vary primarily depending on which staining process is applied to any given primary specimen output piece. For example, variations in cost per primary specimen output piece between H&E staining 130 and IHC staining station 135 can vary by 400 percent or more. However, in many pathology labs, the number of primary specimen output pieces processed via IHC staining station 135 is less than the number of slides processed by H&E staining station 130, thereby resulting in significant disparity if a straight average based on a number of primary output pieces were to be used. Therefore, for purposes of obtaining accurate cost information, proper allocation of costs is desirable.

As noted above, during configuration of a workflow, the number of primary specimen output pieces from each staining process within staining stations 132 (e.g., H&E staining station 130, ISH staining station 133, IHC staining station 135, and special staining station 140) may be entered by a user via workflow scale controls 908. Based on the average batch size and number of batches calculated above for each of staining stations 132, actual costs for each of the staining stations (e.g., H&E staining station 130, ISH staining station 133, IHC staining station 135, and special staining station 140) may be allocated only to those primary specimen output pieces that were processed through a particular staining station, thereby allowing an accurate determination of weighted total cost and time per specimen output piece.

For example, based on exemplary data in Table 1 above, the 101,000 primary specimen output pieces resulting from H&E staining station 130 may be allocated costs associated with H&E staining station 130 calculated in a similar manner to the methods described above. Likewise, 7,200 primary specimen output pieces may be allocated costs associated with ISH staining station 133, 10,000 primary specimen output pieces may be allocated costs associated with special staining station 140, and 500 primary specimen output pieces allocated costs from ISH staining station 133. A fully weighted total cost per primary specimen output piece for the entire lab may then be determined accordingly based on the pre- and post-stain costs and the costs allocated to the output pieces from each of staining stations 132.

Once time allocation and average weighted cost per primary specimen output piece has been calculated, it may be possible to calculate numerous other secondary values based on the weighted cost. For example, error costs may be calculated based on a percentage of failed specimen output pieces and error time calculated based on a number of failed output pieces and the time allocated to creation of such output pieces. Further, values may be broken down into their component parts based on the determined weighted cost per specimen output piece and machine times and service intervals may be determined, among other things. One of ordinary skill in the art will recognize that numerous values may be determined based on the average weighted cost determined by methods described herein, and may be used to represent value and performance data to a user.

The results of the determinations described above, as may then be stored, for example at workflow database 160 (step 525).

It is important to note that the calculations described herein are exemplary and one of ordinary skill in the art will recognize that, based on this information, additional determinations may be made. For example, based on the calculations described above it may be possible to determine and provide instrument costs, overhead costs, error costs, error rates, labor costs, consumables costs, waste costs, and service costs, among other things, all on a per lab station, per lab device, per specimen output piece (i.e., from any station), per batch (for primary specimen output pieces), etc.

Returning to FIG. 4, once the current performance data for the current workflow has been calculated and stored, a user may wish to view output related to current performance of the pathology lab (step 415). FIGS. 10A-10J provide exemplary representations of such output related to the performance data of a pathology lab based on a current workflow. Such output may be generated by PEM interface module 315, presentation generator module 335, control module 310, and GUI module 305, among others. Current results interface 1000 may include current result navigation tabs 1002, current result display area 1004, analysis selector 1006, view selector 1008, stain selector 1009, chart displays 1010, and current result tabular display 1012. Similar to navigation tabs 902, current result navigation tabs 1002 may enable a user to navigate through the result displays of analysis tool 300 by clicking or otherwise actuating any of the associated tabs. For example, current result navigation tabs 1002 may include tabs for an executive summary view, an overview, a detailed view, success rate view, and a stainer comparison view. Upon clicking or otherwise actuating any of current result navigation tabs 1002, a user may be provided a particular section of current results interface 1000 consistent with the actuated tab's title. One of ordinary skill in the art will recognize that more or fewer tabs and/or views may be used as desired.

Figure 10A:
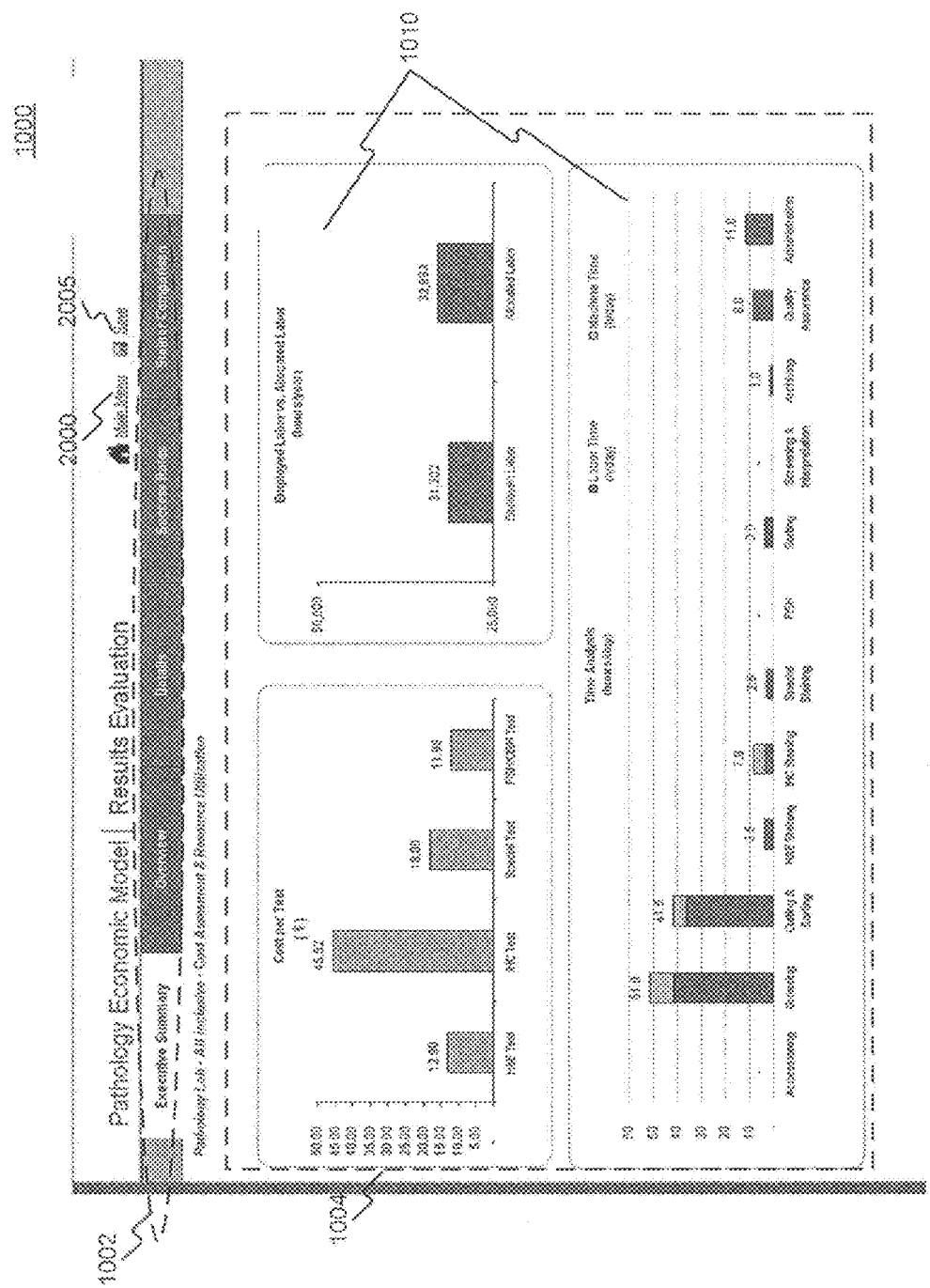
FIG. 10A is an exemplary representation of an interface providing an executive summary of a performance evaluation of an existing workflow.

Current results display area 1004 may be configured to provide a display showing a set of results related to the current performance data associated with the lab. For each tab present in current result navigation tabs 1002, current results display area 1004 may include one or more controls for providing a representation of the current performance data. Current results display area 1004 may include current result chart display 1010, and current result tabular display 1012, among other things, for purposes of providing such output. For example, as shown in FIG. 10A, an executive summary section of current results interface 1000 includes current results display area 1004 including several exemplary chart displays 1010 demonstrating an executive summary of the determined current performance. Exemplary charts include a current cost per test, a labor allocation comparison, and a time analysis (e.g., labor to machine time).

Analysis selector 1006 may be configured to enable a user to select a particular type of analysis for display of results from analysis tool 300 based on the currently selected tab from current result navigation tabs 1002. Analysis selector 1006 may include a list box control, a drop down control, a hyperlink control, or any other suitable control for making a selection. Upon making a selection of a desired analysis, current result display area 1004 may provide the desired view based on the selection of analysis selector 1006.

In addition, a selection of analysis selector 1006 may result in additional controls for further view customization within current results interface 1000 and current result display area 1004, among others. Such controls may include, for example, view selector 1008 and stain selector 1009, each enabling a user to further customize the view of results based on the selection.

Figure 10B:
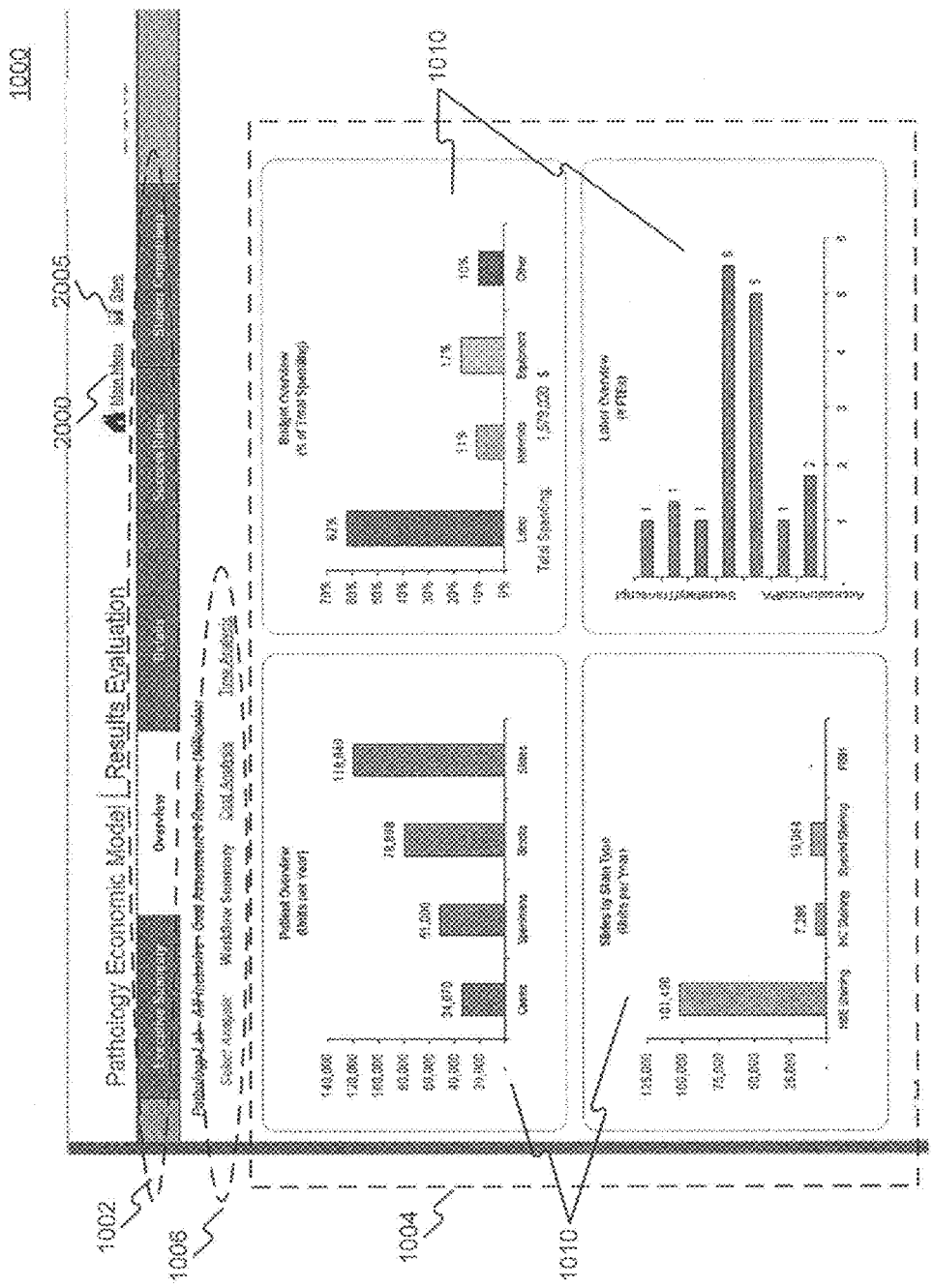
FIG. 10B is an exemplary representation of an interface providing an overview of a performance evaluation in workflow summary mode for an existing workflow.

For example, FIG. 10B shows an exemplary overview section of current results interface 1000 with current results display area 1004 including several exemplary chart displays enabling display of an overview of the current performance data associated with the pathology lab. In addition, analysis selector 1006 is provided enabling a user to determine which type of overview to view. Exemplary overview types include a workflow summary overview, a cost analysis overview, and a time analysis overview, among others. As shown in FIG. 10B, a workflow summary overview may include exemplary chart displays 1010 showing a staff overview, a budget overview including a total spending analysis, a number of specimen output pieces by station, and a labor overview.

Figure 10C:
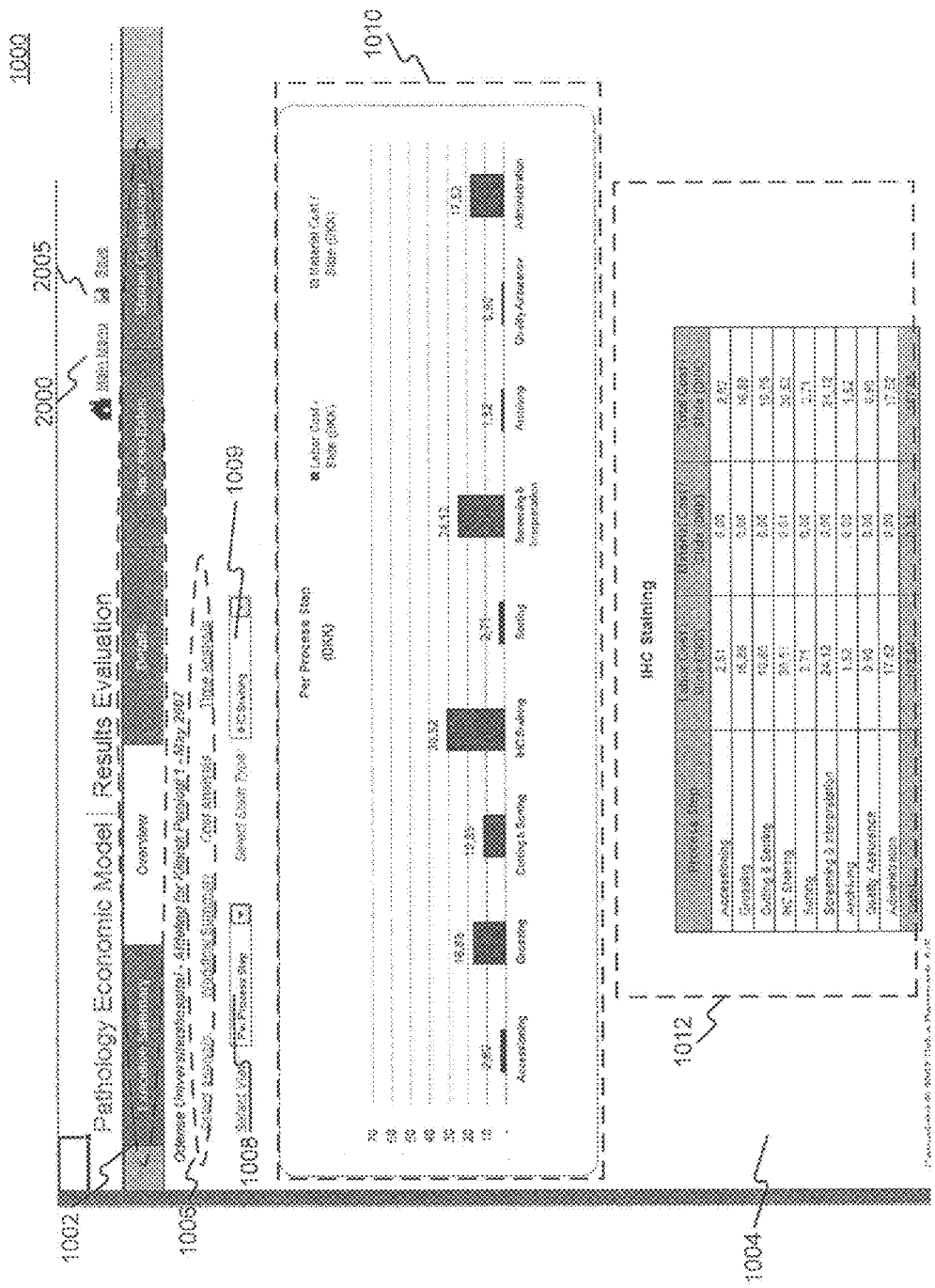
FIG. 10C is an exemplary representation of an interface providing an overview of a performance evaluation in cost analysis mode for labor cost allocation for each process in an existing workflow.
Figure 10D:
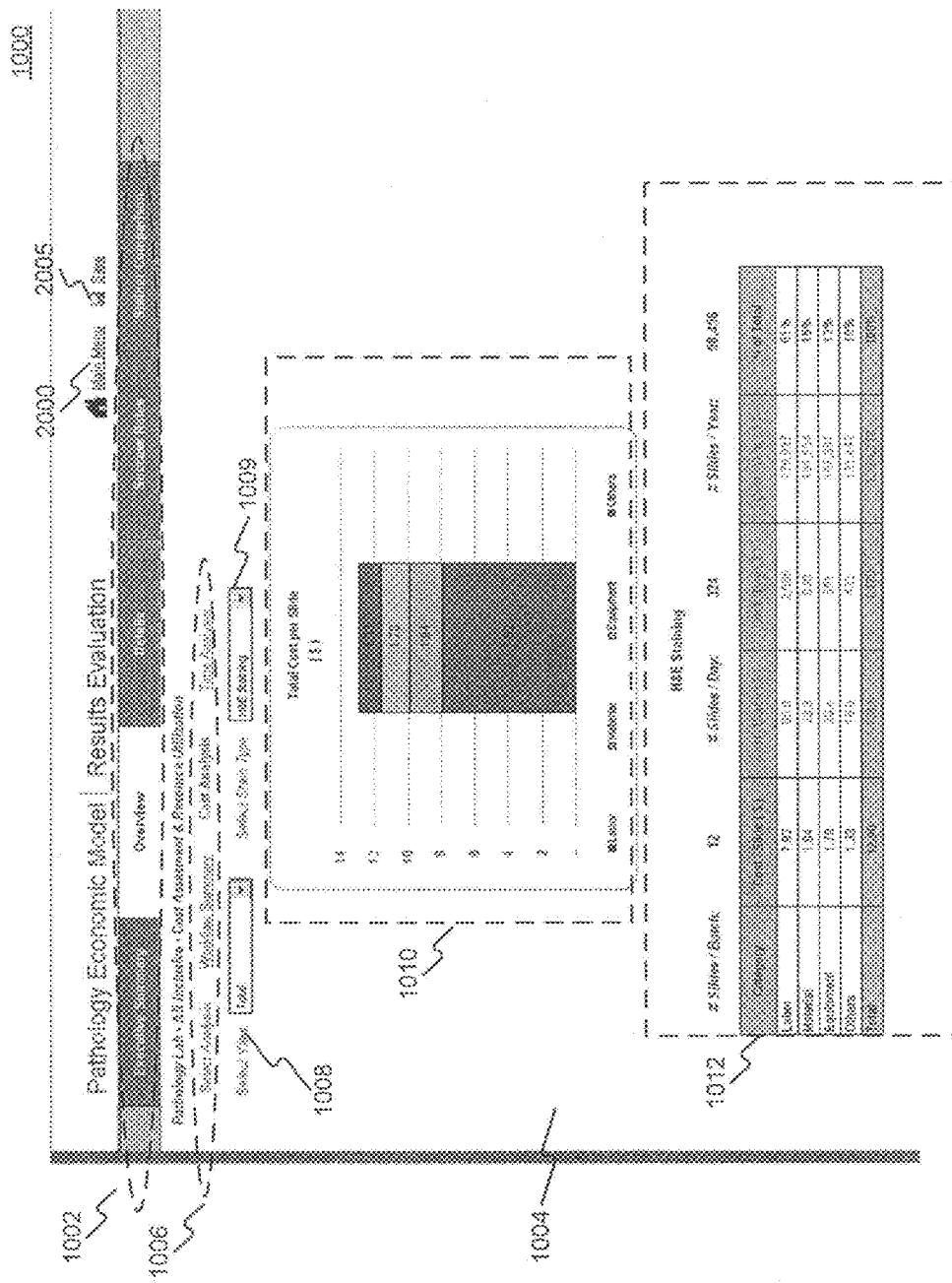
FIG. 10D is an exemplary representation of an interface providing an overview of a performance evaluation in cost analysis mode for the H&E staining process of an existing workflow.
Figure 10E:
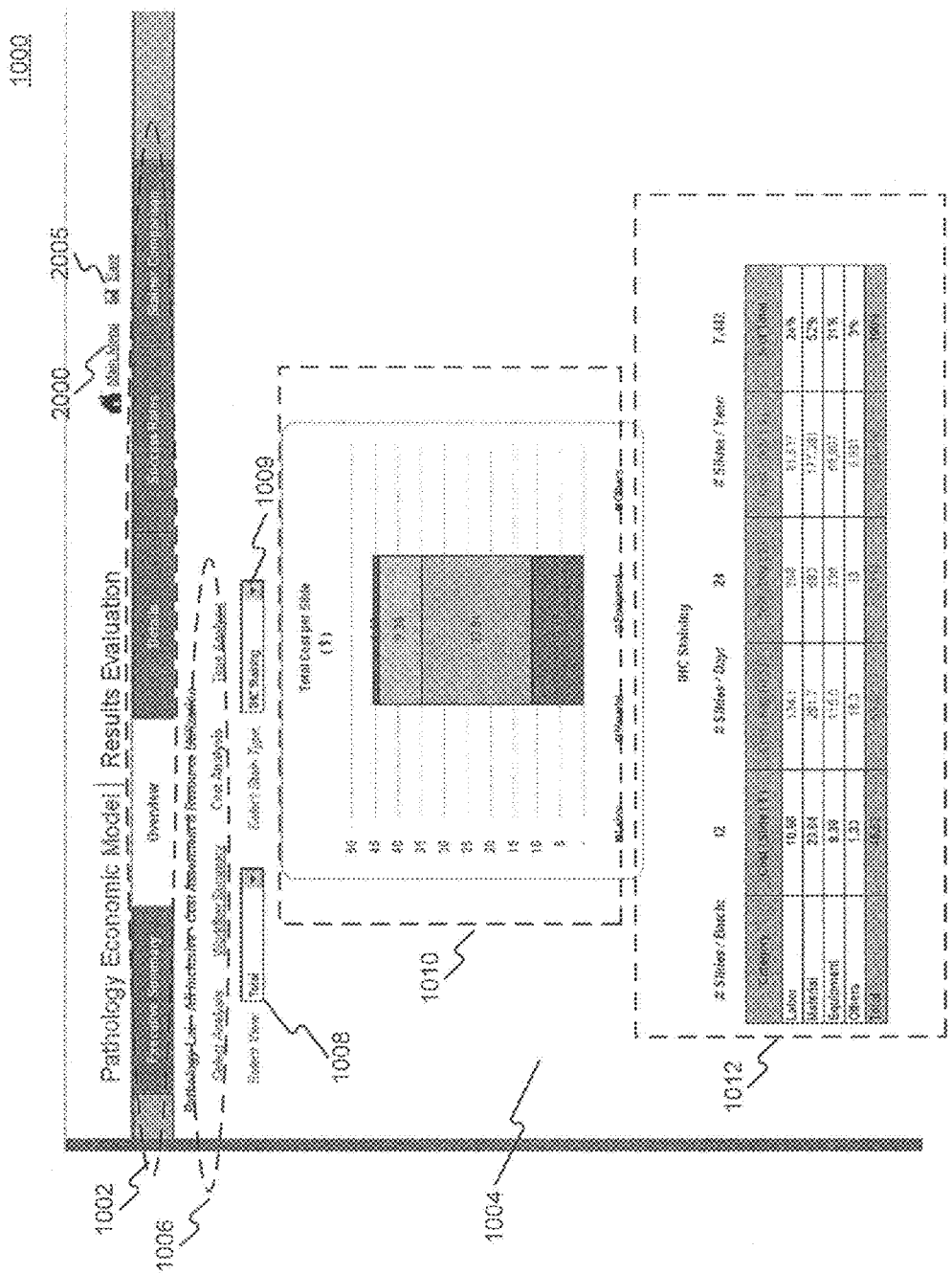
FIG. 10E is an exemplary representation of an interface providing an overview of a performance evaluation in cost analysis mode for the IHC staining process of an existing workflow.
Figure 10F:
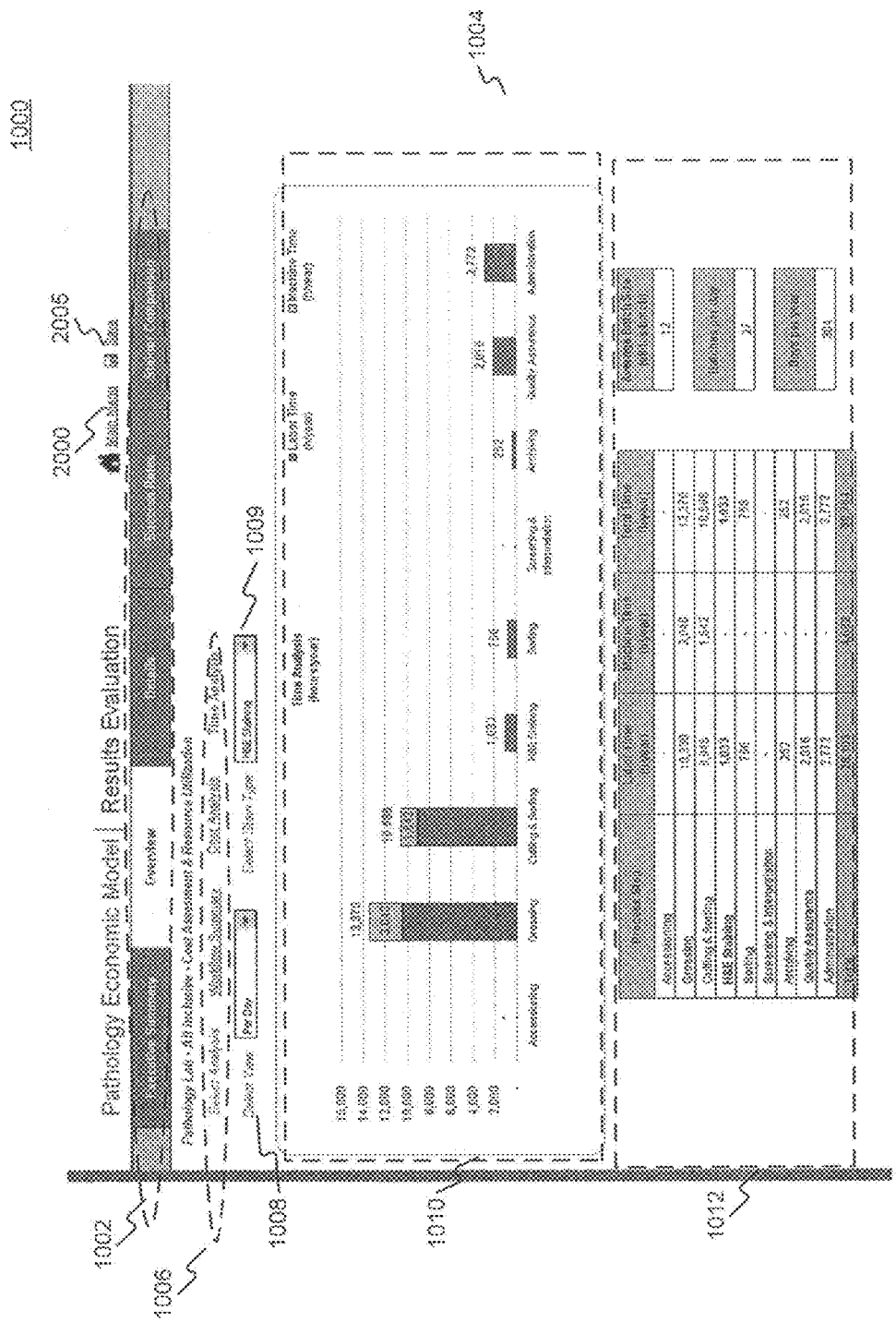
FIG. 10F is an exemplary representation of an interface providing an overview of a performance evaluation in time analysis mode for the H&E staining process of an existing workflow.
Figure 10G:
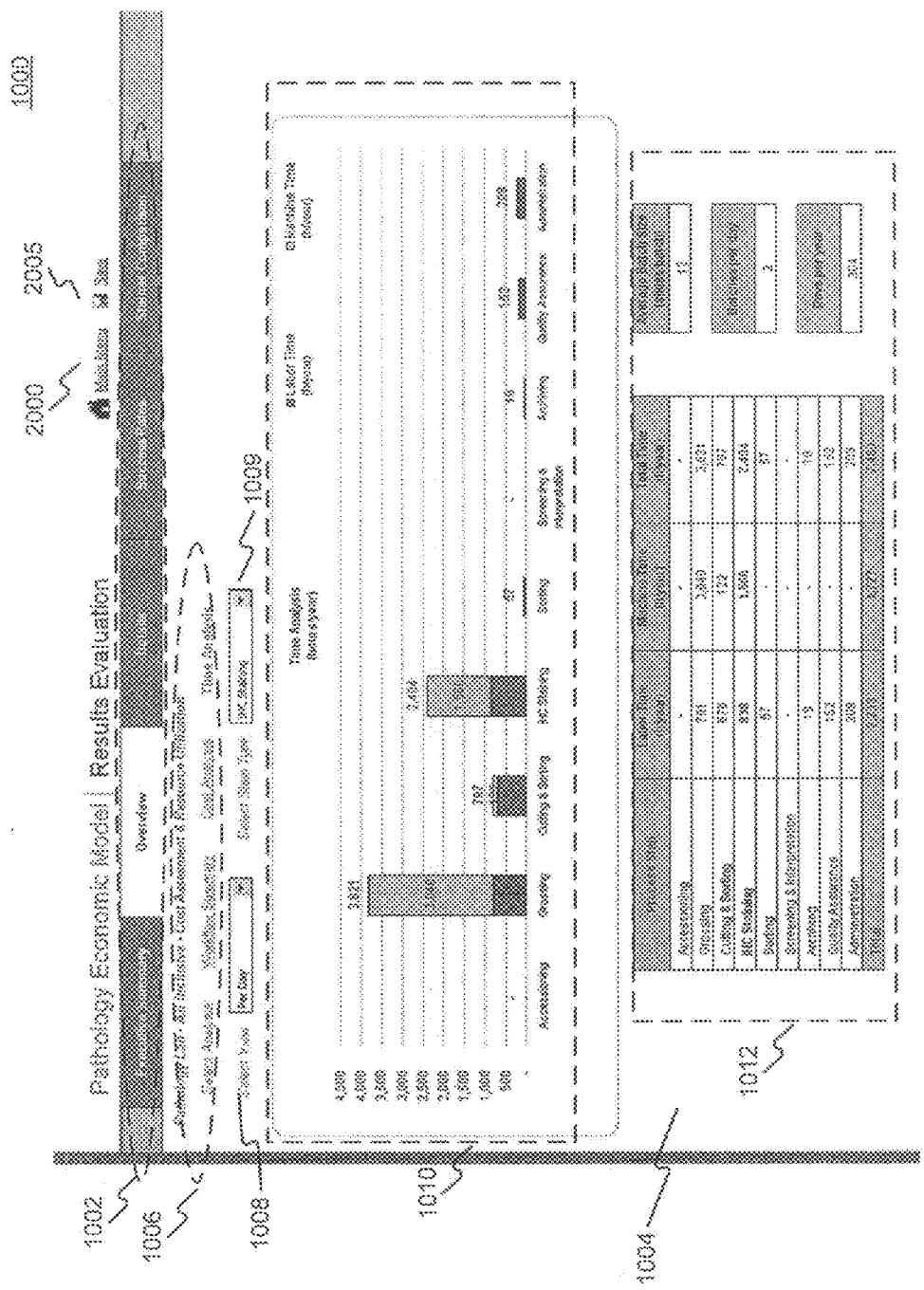
FIG. 10G is an exemplary representation of an interface providing an overview of a performance evaluation in time analysis mode for the IHC staining process of an existing workflow.
Figure 10H:
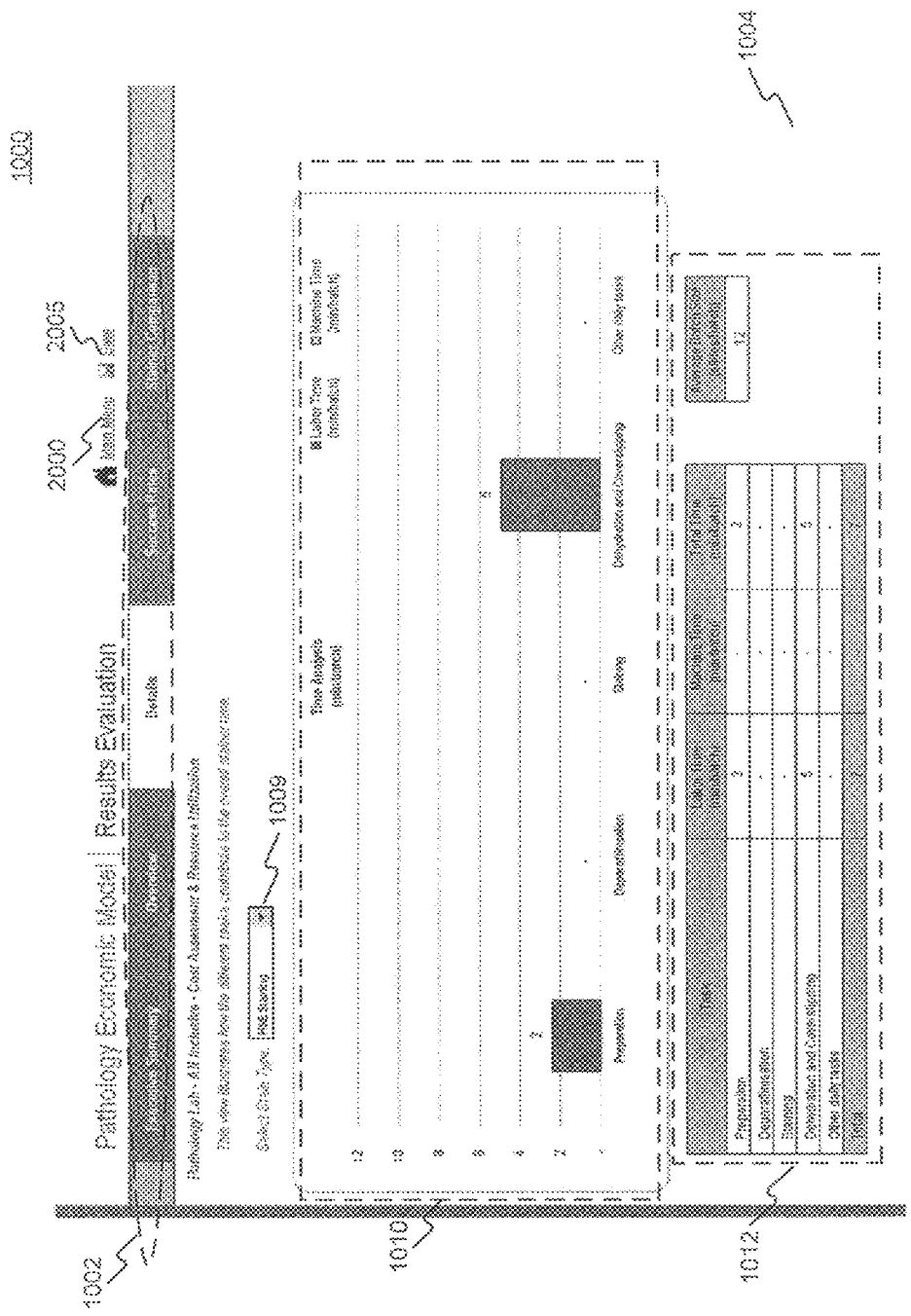
FIG. 10H is an exemplary representation of an interface providing a detailed view of a performance evaluation for the H&E staining process of an existing workflow.
Figure 10I:
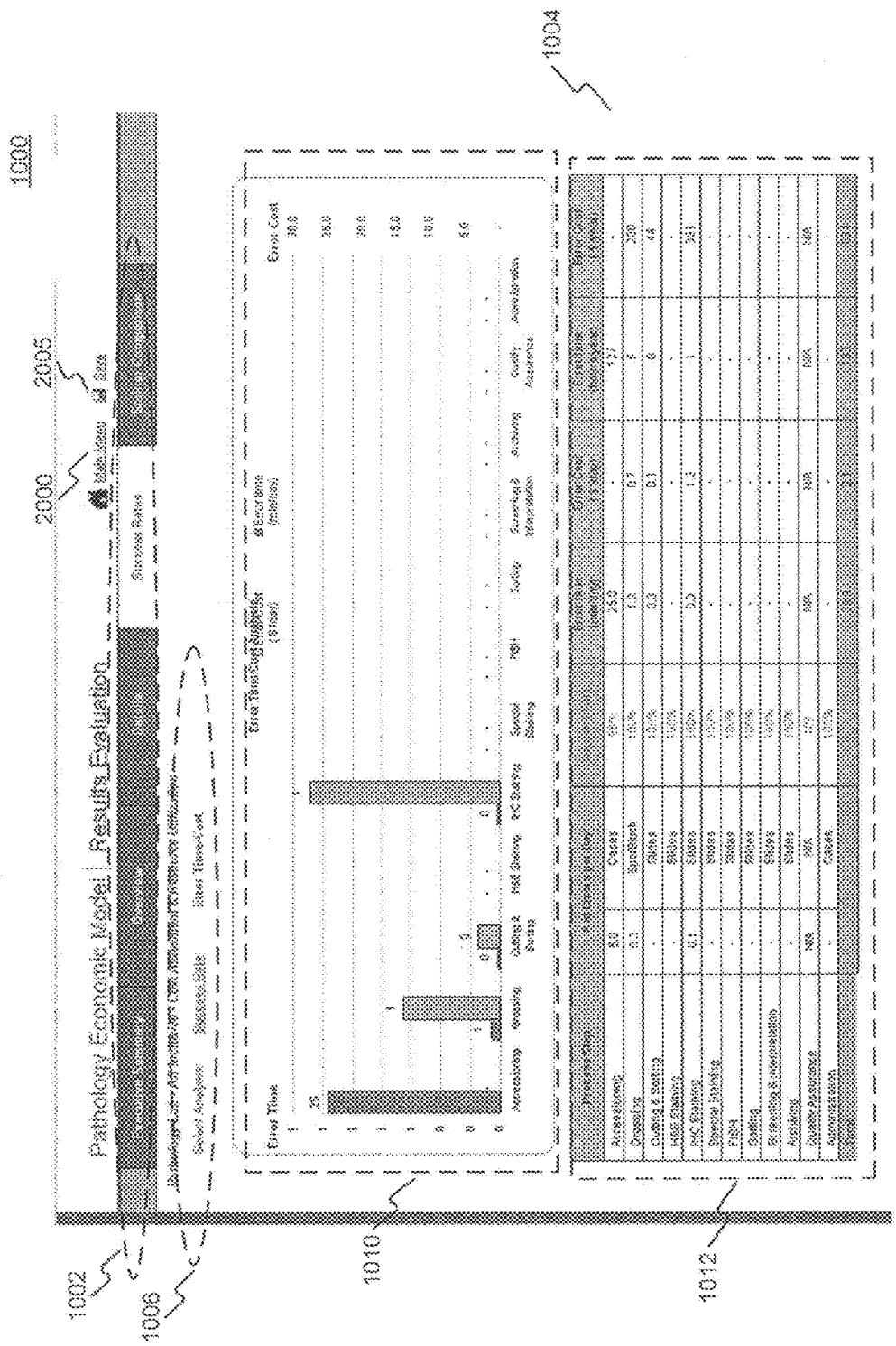
FIG. 10I is an exemplary representation of an interface providing a view of success rate analysis in error time cost mode for an existing workflow.

FIG. 10C and FIG. 10D show exemplary overviews upon user selection of a cost analysis mode from analysis selector 1006. As can be seen, view selector 1008 and stain selector 1009 are provided. View selector 1008 may enable a user to customize the display based on a view type (e.g., totals, per workflow process, etc.), while stain selector 1009 may enable a user to customize the display based on a particular staining process. For example, FIG. 10C shows an overview for labor cost allocation for each process step in an existing workflow, while FIG. 10D shows a totals view based on the H&E staining process. Chart display 1010 may display an exemplary bar chart highlighting the data associated with costs per specimen output piece for the H&E staining process of an existing workflow while tabular display 1012 may display the data in a tabular manner. In FIG. 10E, a totals view based on the IHC staining process is shown. Again, chart display 1010 may provide a bar and/or any other type of chart demonstrating costs per specimen output piece while tabular display 1012 may provide related data in tabular form.

It is important to note that options available through analysis selector 1006, view selector 1008, and staining selector 1009, among others, may vary as a result of selections of, for example, tabs in current result navigation tabs 1002, analysis selector 1006, view selector 1008, and staining selector 1009. In other words, the options available in each of the selectors may be dependent on one another.

Figure 10J:
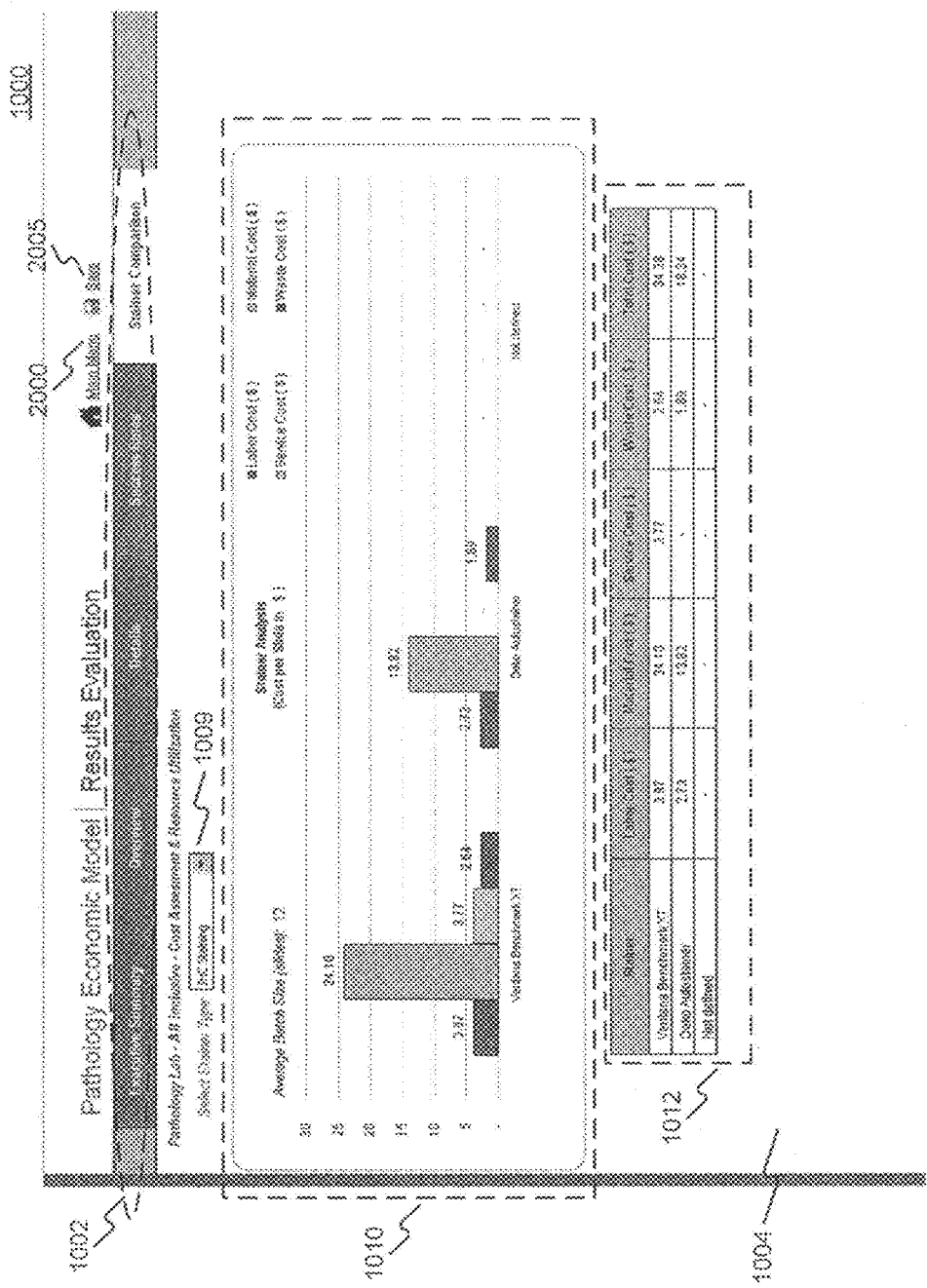
FIG. 10J is an exemplary representation of an interface providing a stainer comparison for the IHC staining process of an existing workflow.

FIGS. 10F-10J show various other output information related to current performance data associated with a pathology lab which may be presented through current results display area 1004, chart displays 1010, and tabular display 1012, and customized with analysis selector 1006, view selector 1008 and stain selector 1009. These output displays include a per day time analysis overview of the H&E staining process (FIG. 10F), a per day time analysis of the IHC staining process (FIG. 10G), a detailed view of the H&E staining process (FIG. 10H), an error time cost analysis of the current workflow (FIG. 10I), and a stainer analysis for the IHC staining process based on current stainers in the workflow (FIG. 10J). One of ordinary skill in the art will recognize that upon review of these figures, more or fewer views of results may be provided based on the desires of a user. Further, one of ordinary skill in the art will recognize that results of the performance calculations can be displayed in any other suitable format without departing from the scope of the present disclosure.

Other functionality related to the results may also be provided. For example, in addition to viewing current performance results from within analysis tool 300, analysis tool 300 may provide functionality enabling a user to export the output to one or more formats, such as, for example, Microsoft PowerPoint, Microsoft Word, OpenOffice Impress, etc.

A user may wish to propose one or more changes to the workflow based on the current performance data and a desired change, or alternatively, in response to another user's request to review effects of a revised workflow. A user may thus utilize a second interface for providing one or more modifications to the current workflow (step 420). Such modifications may take the form of adding one or more new laboratory devices to the existing workflow and/or replacing one or more laboratory devices in the current workflow. For example, where a current workflow calls for manually cutting tissue samples at sectioning station 125, an automated microtome may be introduced as a proposed revision to the current workflow. In another example, where a current workflow includes several staining devices, a proposed modification may include replacing one or more of the several staining devices with different staining devices. One of skill in the art will recognize that the modifications described herein are exemplary only and numerous other modifications to a workflow may be possible. For example, devices enabling rapid identification and labeling of specimens may be included in the workflow as well as image sharing software and various other items. Any such modifications to a workflow are intended to fall within the scope of the present disclosure.

Figure 11A:
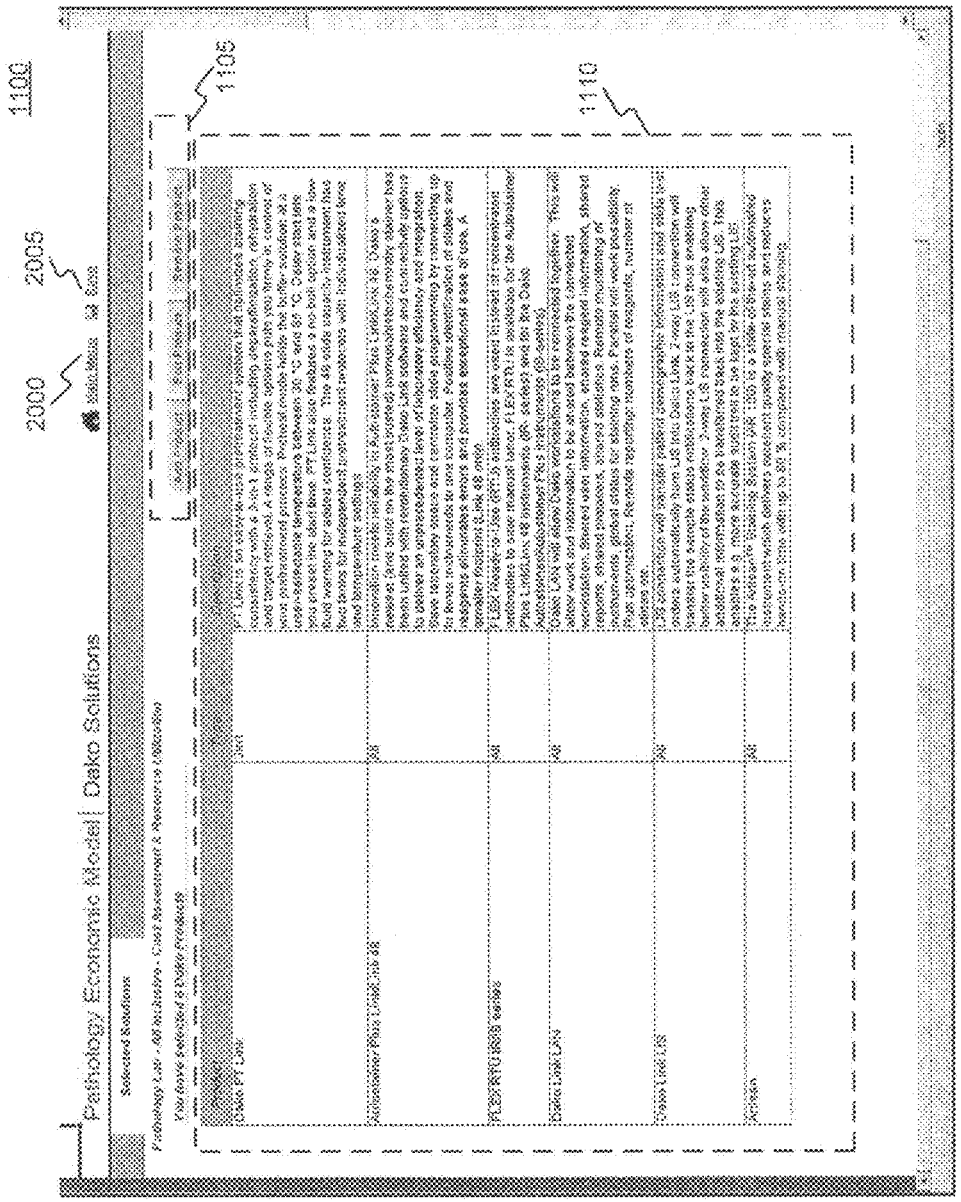
FIG. 11A is an exemplary depiction of an interface displaying proposed workflow modifications to an existing workflow.
Figure 11B:
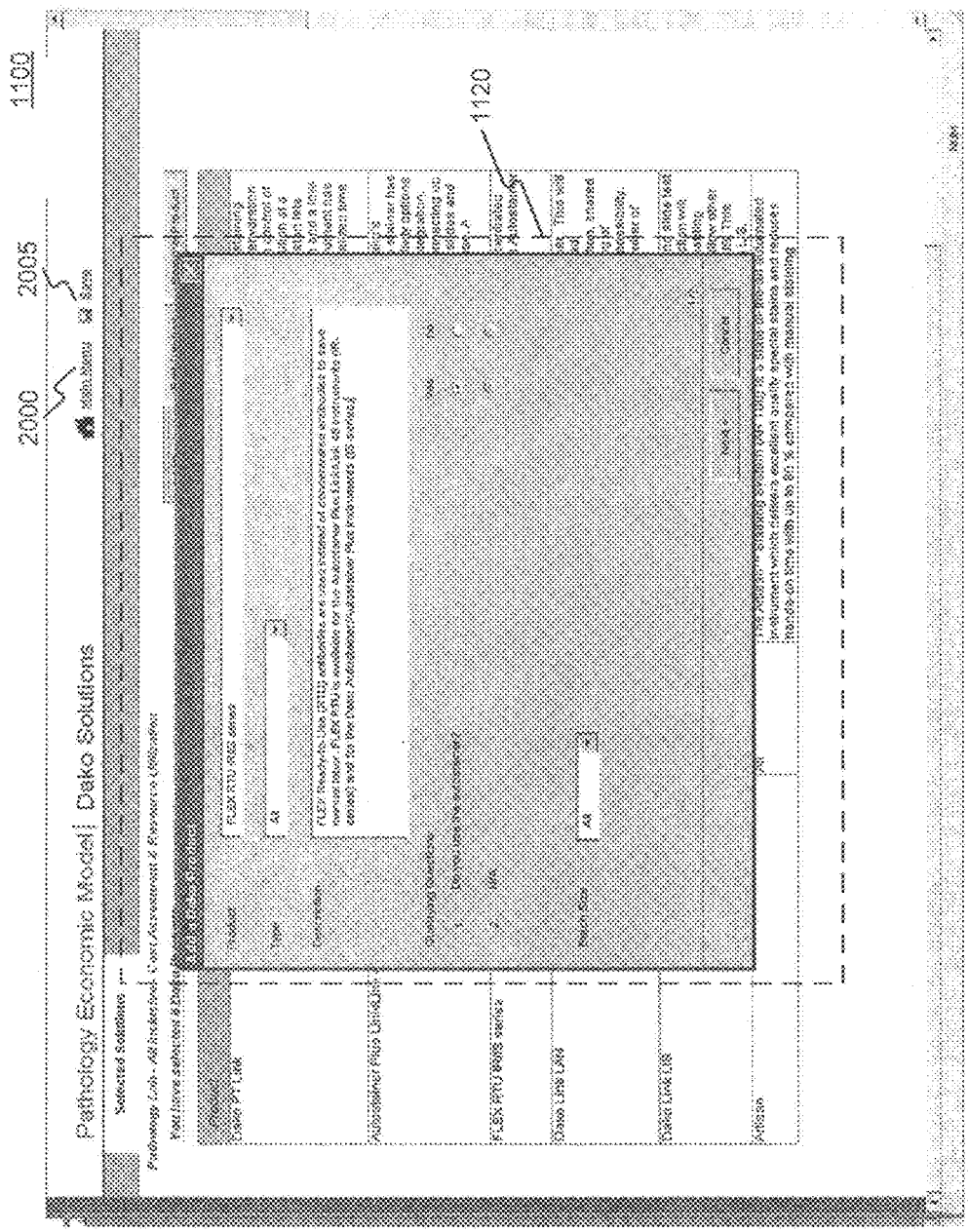
FIG. 11B is an exemplary depiction of a modification dialog enabling a user to add a proposed modification to an existing workflow.
Figure 11C:
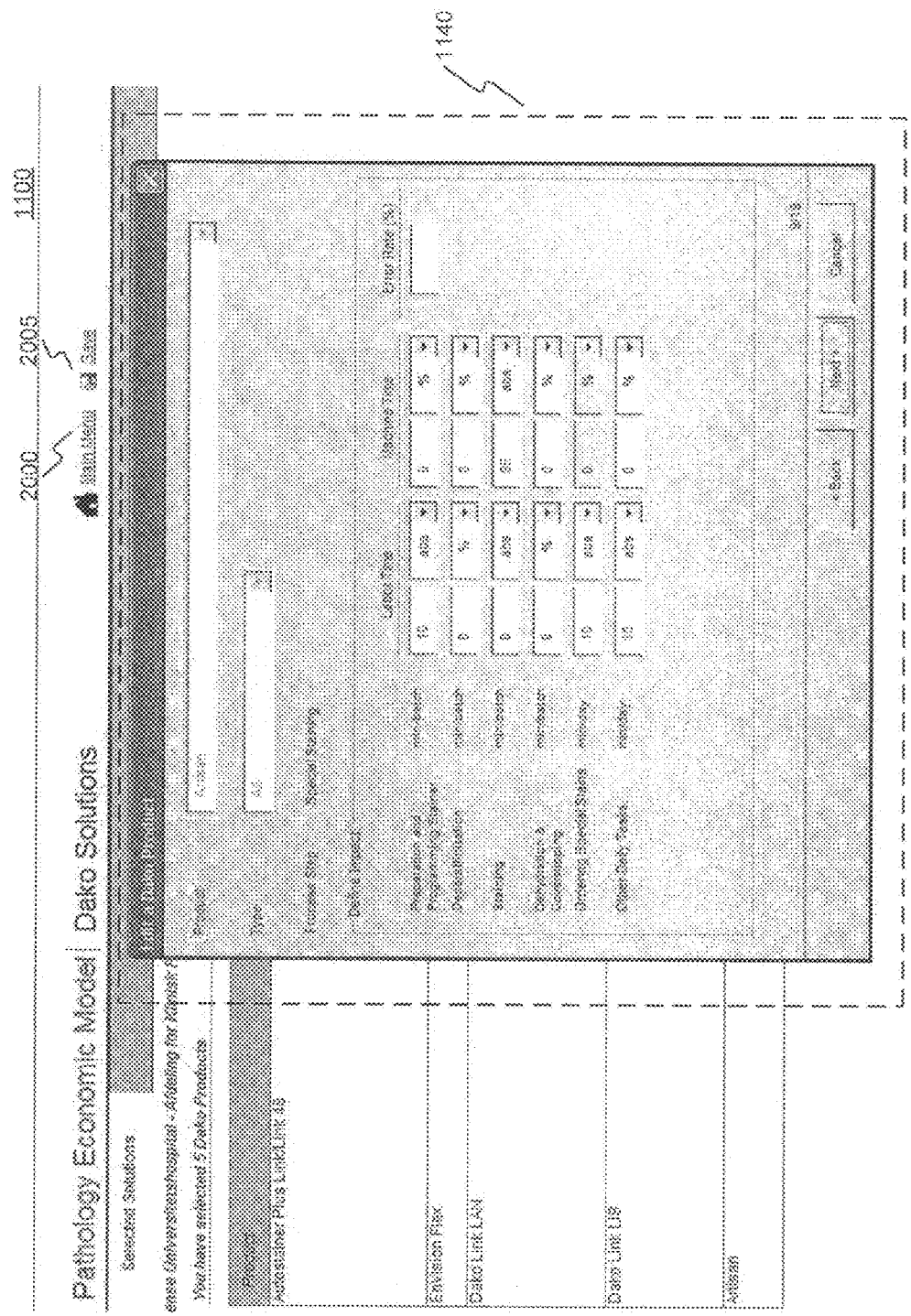
FIG. 11C is an exemplary depiction of an edit dialog enabling user customization of a proposed modification to an existing workflow.

FIGS. 11A-11C provide an exemplary view of second interface 1100 for proposing modifications to a workflow. Second interface may be generated by PEM interface module 315, presentation generator module 335, control module 310, and GUI module 305, among others. FIG. 11A is an exemplary depiction of second interface 1100 displaying proposed workflow modifications to an existing workflow. Action buttons 1105 may enable a user to add, edit, or delete a modification from a proposed list of modifications displayed at proposal display 1110. For example, a user may review currently proposed modifications to a workflow, if any, displayed in proposal display 1110. If the user desires to add a modification to the workflow (e.g., a different autostainer), the user may select the add button from action buttons 1105. The user may then be presented a dialog enabling addition of a workflow modification, such as that shown at FIG. 11B.

FIG. 11B is an exemplary depiction of a modification dialog 1120 enabling a user to add a proposed modification to an existing workflow. Upon accessing such a dialog, product definition module 325 may cause data module 330 to retrieve a list of laboratory devices and associated parameters available for modifying a currently configured workflow. Such a list may include autostainer devices, microtome devices, specimen identifying devices, specimen marking devices, image sharing devices, image analysis devices, cover slipping devices, slide pretreatment devices, tissue processing devices, and information display devices (e.g., computing devices 111), among other things. Each of these devices may have one or more parameters associated (e.g., labor time, machine time, and error rate, among others), which may define operation and potential benefit of addition of such a device to a workflow. Such data may be presented as a percentage benefit, an absolute change, or incremental delta. Presentation generator module 335 may then cause one or more controls to be displayed to a user within modification dialog 1120 enabling a user to review and select one or more proposed revisions to the workflow. For example, a user may view an autostainer with parameters indicating that a 20 percent reduction in setup time may be realized by implementing such a stainer in a currently configured workflow. Therefore, the user may elect to make such a modification and add the stainer via modification dialog 1120. The proposed modification may then be provided to data module 330 for updating a proposed workflow and proposal display 1110. This procedure may be repeated for each additional device a user wishes to include in the proposed modifications.

A user also may make modifications to the one or more laboratory devices available for modifying a workflow. For example, where security module 355 indicates that a user may modify parameters associated with laboratory devices the user may access edit modification dialog 1140, enabling configuration of one or more laboratory devices. FIG. 11C is an exemplary depiction of an edit dialog enabling user customization of a proposed modification to an existing workflow.

Edit modification dialog may enable a user to review parameters stored in workflow database 160 and provided via product definition module 350 associated with the available laboratory devices. For example, a user may modify labor time, machine time, and error rate, etc. It is important to note that often, a user will have empirically determined parameters related to one or more laboratory devices stored in workflow database 160. However, the ability to modify and/or create a new device enables a user to compare potentially competing devices where, for example, only a white paper is available for the competing device.

Figure 6:
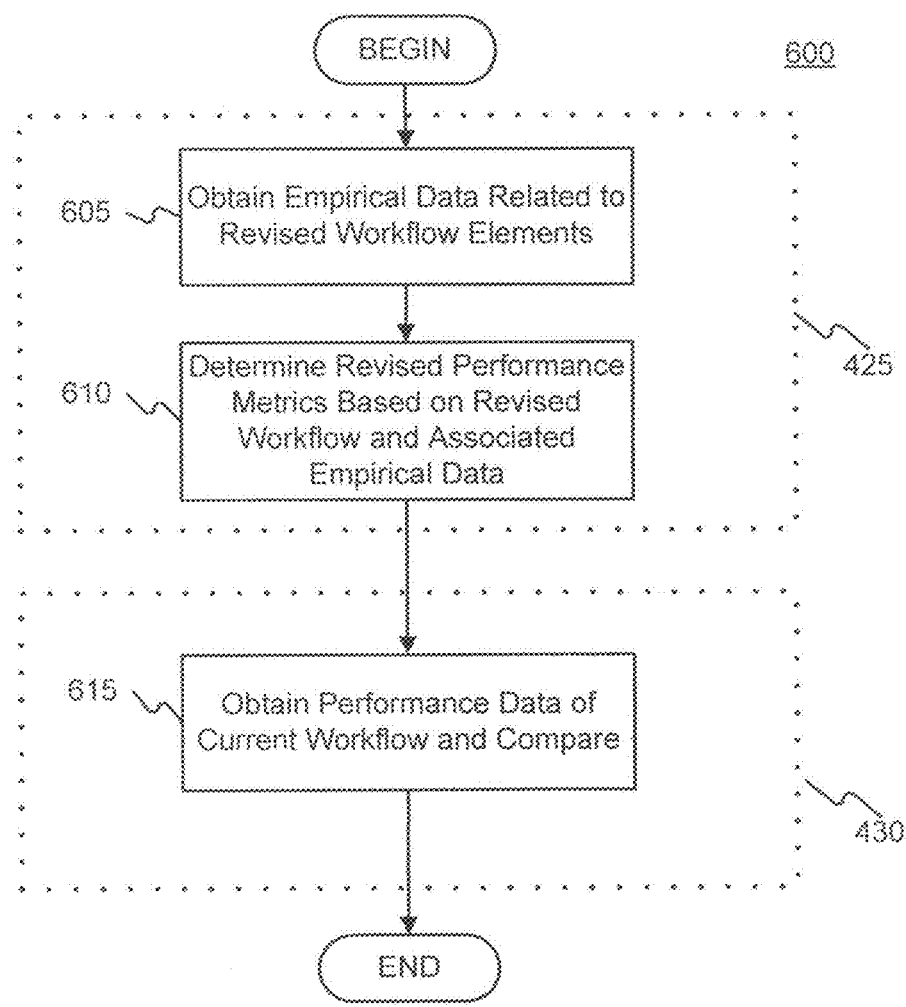
FIG. 6 is a block diagram showing an exemplary method for determining revised performance data based on one or more modifications to an existing workflow and providing output based on a comparison.

Once a user has proposed modifications to a workflow, analysis tool 300 may execute a second analysis resulting in calculation of revised and forecasted performance data based on the workflow and proposed modifications (step 425) and compare the forecasted performance data with the results related to the current performance data determined above (step 430). FIG. 6 is a block diagram showing an exemplary method for determining revised performance data based on one or more modifications to an existing workflow, and providing output based on a comparison. Analysis tool 300 may retrieve empirical and/or user input data related to the one or more proposed modifications to the current workflow selected at step 420 (step 605). Such information may include labor time, machine time, and error rate, among other things and may be retrieved via data module 330, product definition module 325, and/or any other suitable module.

Following retrieval of the parameters related to proposed modifications, analysis tool 300 may determine, based on the proposed modifications and the current workflow, forecasted performance data for the revised workflow (step 610). Such calculations may be carried out in a similar fashion to those described in regard to step 410, however, such calculations may utilize the revised parameters where the one or more proposed workflow modifications have replaced originally defined workflow configurations. For example, where an original stainer with a labor set up time of 2 hours has been replaced by a stainer having a labor set up time of 1.5 hours, such time difference may be factored into the calculation of the forecasted performance data.

Analysis tool 300 may then retrieve data related to the originally generated performance data of the pathology lab for comparison with the newly forecasted performance data (step 615). For example, each workflow station may be compared based on, for example, instrument costs, revised overhead costs, error costs, labor costs, consumables costs, waste costs, and service costs, among other things. Further, the results may be combined for the lab as a whole and/or broken out into various categories for analysis as described below (e.g., costs per specimen output piece, costs per stainer, etc.).

Returning to FIG. 4, once a performance analysis has been run with the one or more proposed workflow modifications and the results compared, a user may review an output of the comparison in a third interface (step 440). FIGS. 12A-12I show exemplary representations of a third interface 1200 providing output of the results of a comparison between current performance data and revised performance data. Third interface may be generated by PEM interface module 315, presentation generator module 335, control module 310, and GUI module 305, among others. Third interface 1200 may include comparison display navigation tabs 1202, comparison display area 1204, analysis selector 1206, view selector 1208, stain selector 1209, chart displays 1210, and comparison result tabular display 1212. Similar to navigation tabs 902, comparison display navigation tabs 1202 may enable a user to navigate through the result displays of analysis tool 300 by clicking or otherwise actuating any of the associated tabs. For example, comparison display navigation tabs 1202 may include tabs for an executive summary view, a time analysis view, a success rate view, and a stainer comparison view. One of ordinary skill in the art will recognize that more or fewer tabs and views may be provided as desired. Upon clicking or otherwise actuating any of comparison display navigation tabs 1202, a user may be provided a particular section of third interface 1200 consistent with the actuated tab's title or other suitable identifier.

Figure 12A:
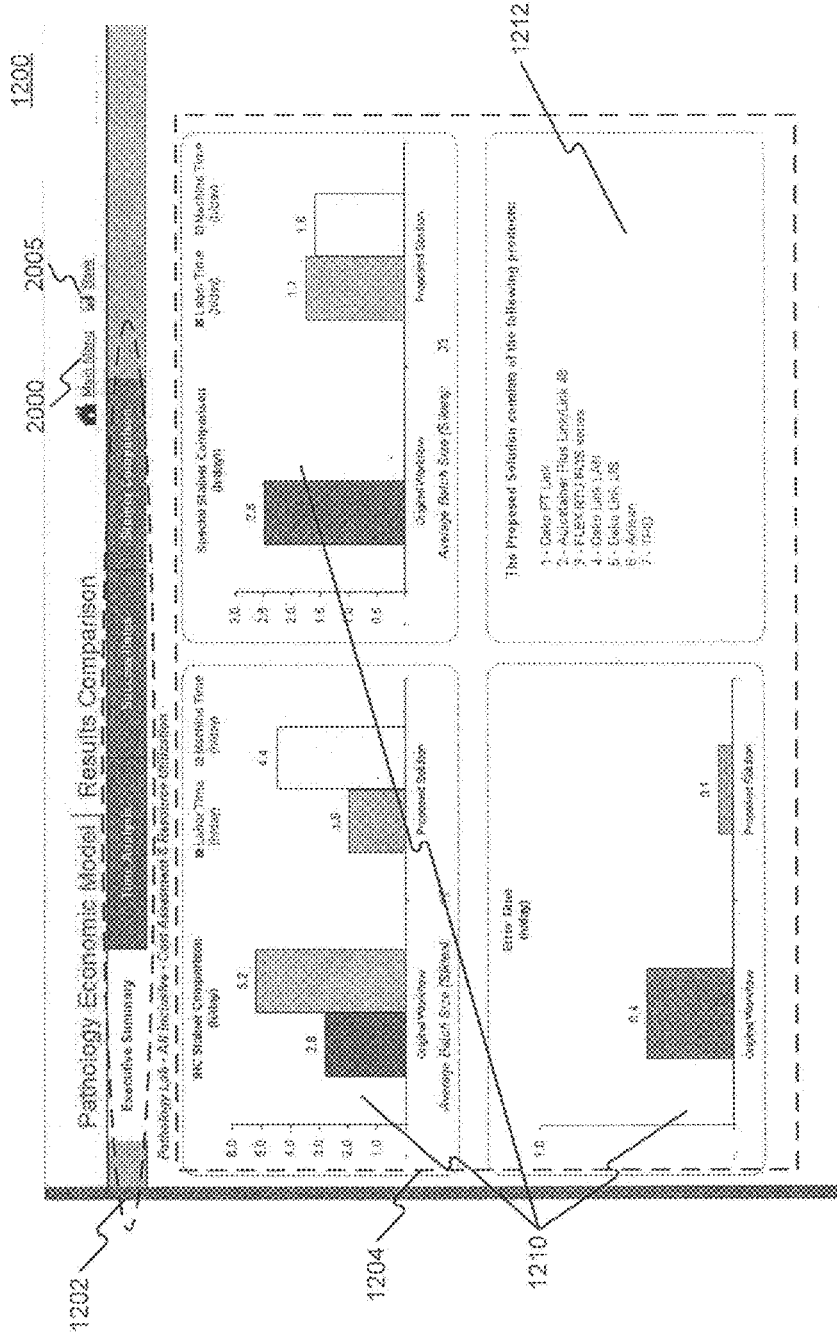
FIG. 12A is an exemplary representation of an interface providing an executive summary of a comparison between the performance evaluation of an existing workflow and a proposed workflow.

Comparison results display area 1204 may be configured to provide a display showing a set of results related to the comparison between current performance data associated with the lab and forecasted performance data based on the one or more proposed modifications to the current workflow. It is important to note that for each tab present in comparison display navigation tabs 1202, comparison results display area 1204 may include one or more varying controls for providing a representation of the comparison between current performance data and forecasted performance data based on the one or more proposed workflow modifications. In some exemplary embodiments, comparison display area 1204 may include comparison result chart display 1210, and comparison result tabular display 1212, among other things for purposes of providing output. For example, as shown in FIG. 12A, an executive summary section of third interface 1200 includes comparison results display area 1204 including several exemplary chart displays 1210 demonstrating an executive summary of the comparison. Exemplary charts include an IHC stainer comparison, a special stainer comparison, and an error time comparison. Note that each exemplary chart displays throughout the disclosure may include multiple comparisons, for example, a chart may compare both labor time and machine time in an existing workflow and a proposed workflow. Further, display of comparison data may be limited to showing comparisons where workflow modifications were proposed, or, alternatively, a user may be enabled to view all aspects of a work flow regardless of whether a change was proposed or not.

Analysis selector 1206 may be configured to enable a user to select a particular type of analysis for display of results from analysis tool 300 based on the currently selected tab from comparison display navigation tabs 1202. Analysis selector 1206 may include a list box control, a drop down control, a hyperlink control, or any other suitable control for making a selection. Exemplary options for analysis selector 1206 may include a view per batch, view per day, view per year, per specimen output piece (e.g., slide), etc. Upon making a selection of a desired analysis, comparison display area 1204 may provide the desired view based on the selection of analysis selector 1206.

In addition, a selection of analysis selector 1206 may result in additional controls for further view customization within third interface 1200 and comparison display area 1204, among others. Such controls may include, for example, stain selector 1209 and metric selector 1211 each enabling a user to further customize the view of results based on the selection. Exemplary options for stain selector 1209 may include H&E staining, IHC staining, special staining, and ISH staining, among others. Exemplary options for metric selector 1211 may include labor time and machine time, among others.

Figure 12B:
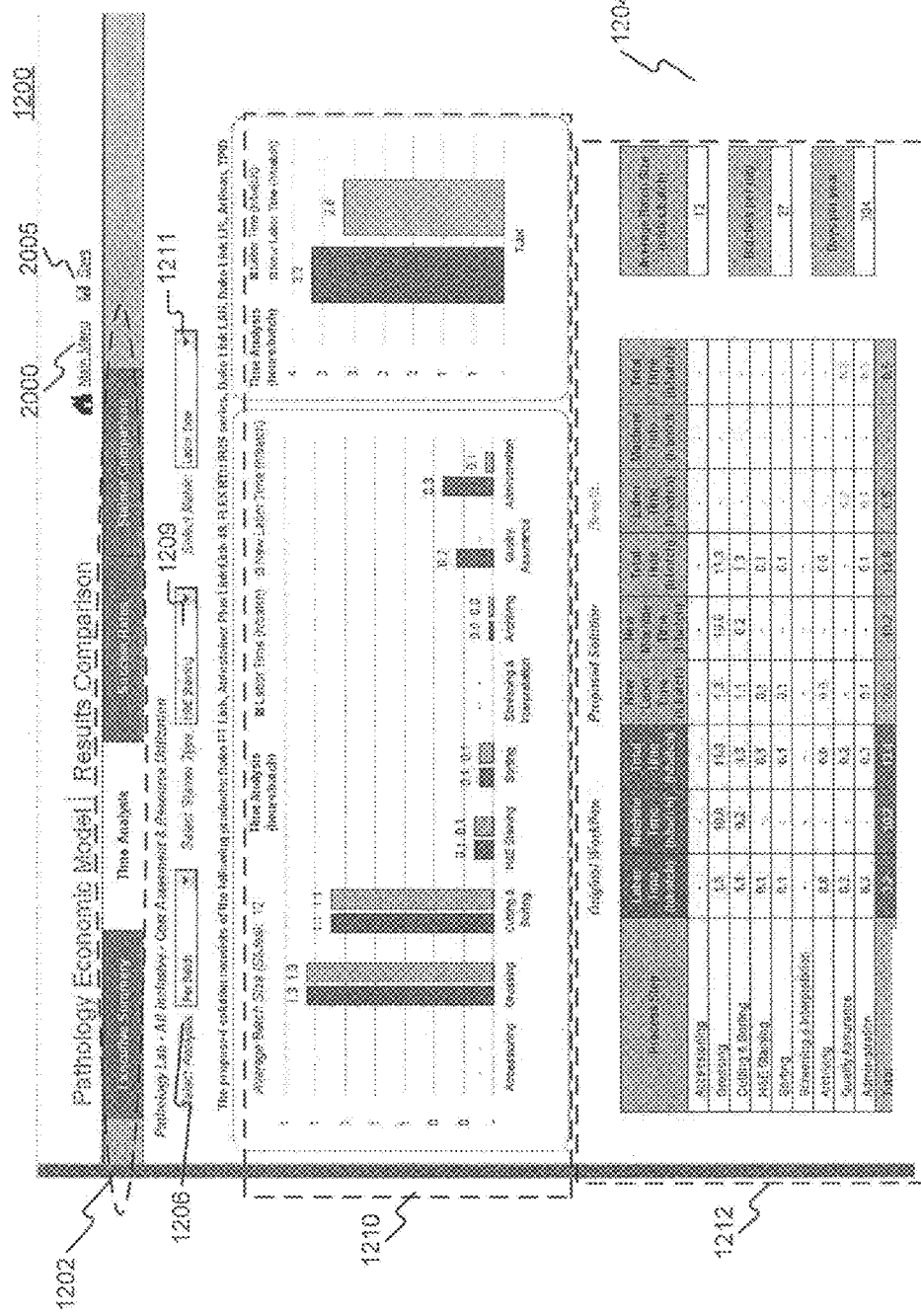
FIG. 12B is an exemplary representation of an interface providing a time analysis comparison between the performance evaluation of an existing workflow and a proposed workflow for the H&E staining process, based on labor time.
Figure 12C:
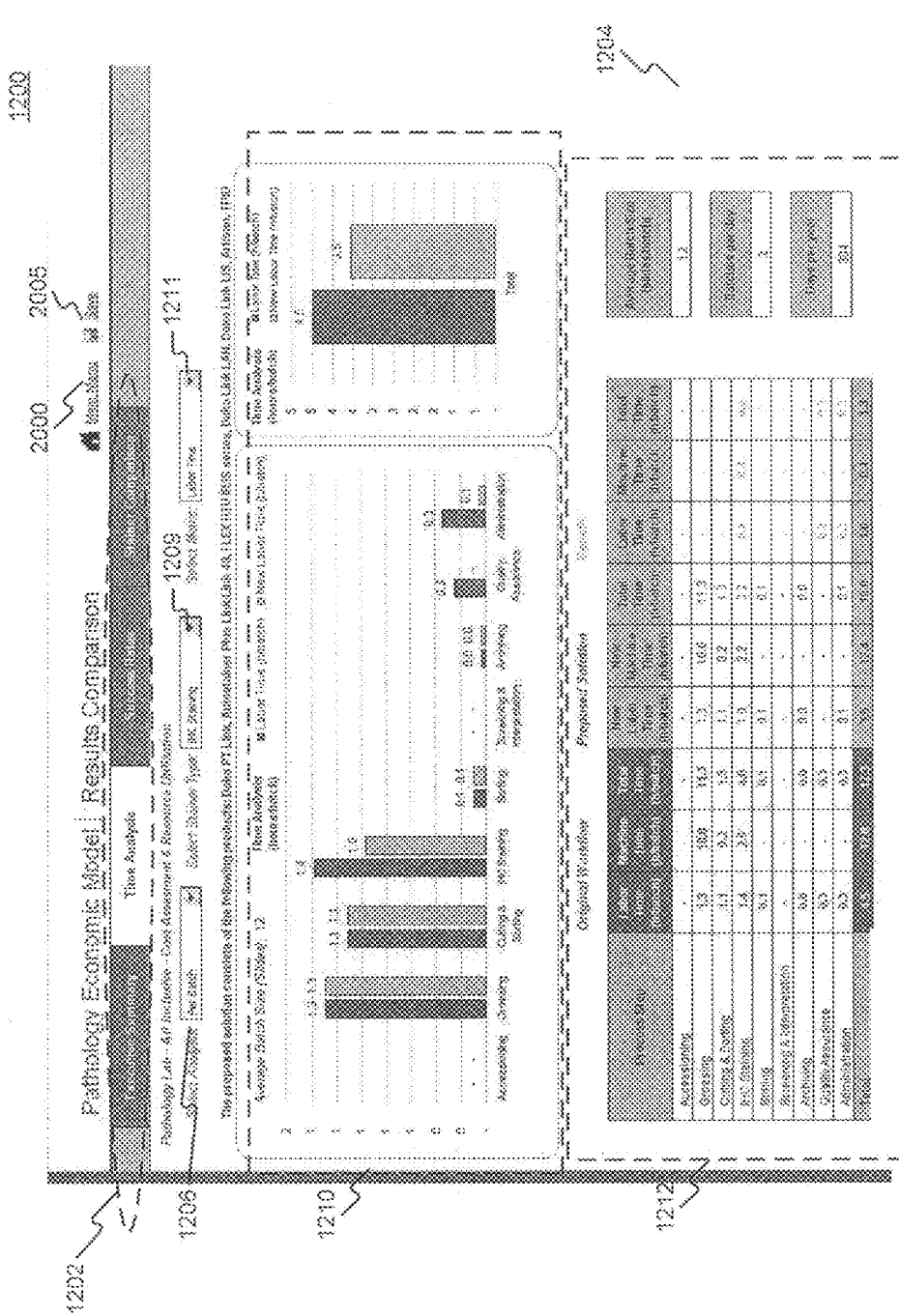
FIG. 12C is an exemplary representation of an interface providing a time analysis comparison between the performance evaluation of an existing workflow and a proposed workflow for the IHC staining process, based on labor time.
Figure 12D:
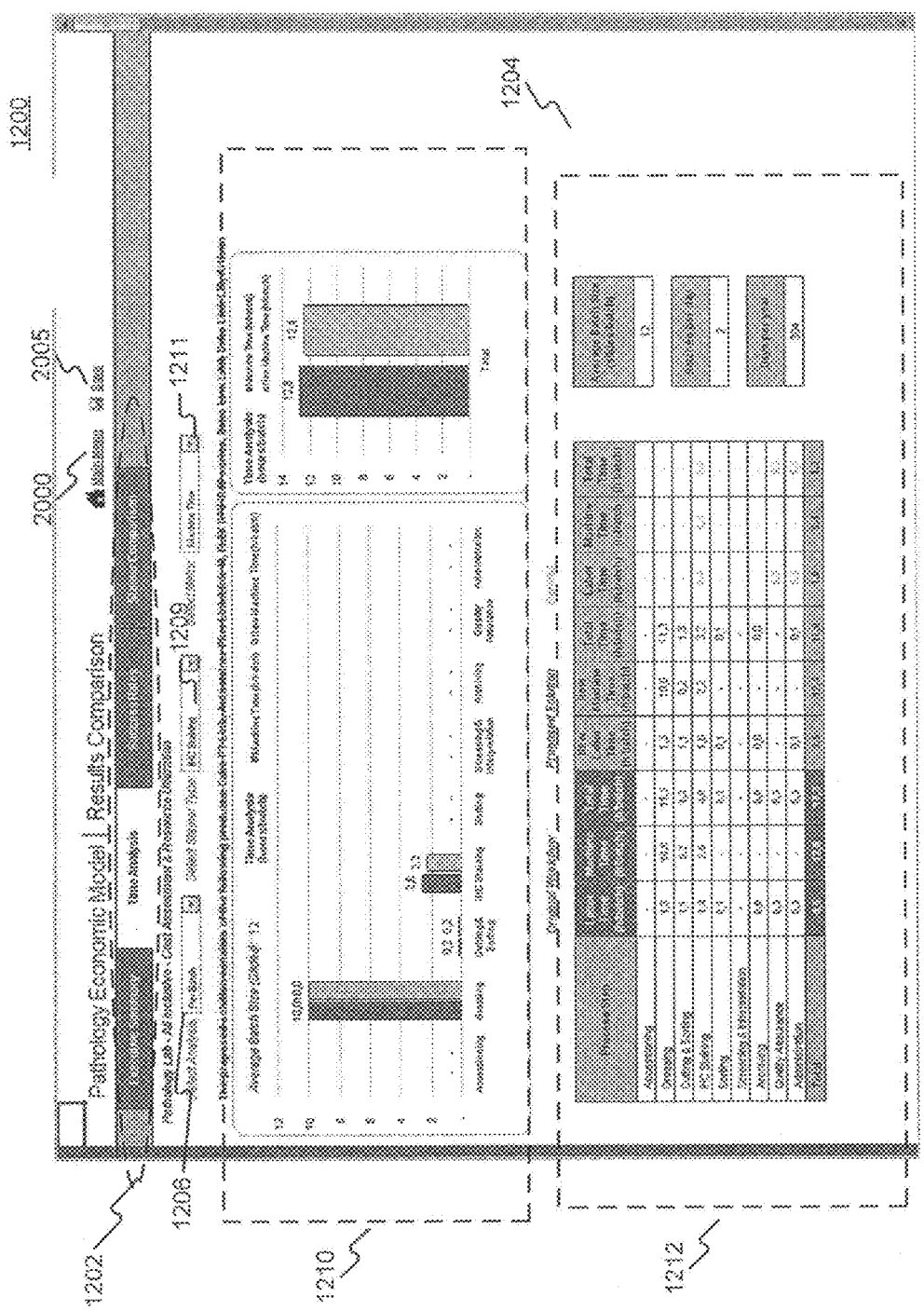
FIG. 12D is an exemplary representation of an interface providing a time analysis comparison between the performance evaluation of an existing workflow and a proposed workflow for the IHC staining process, based on machine time.
Figure 12E:
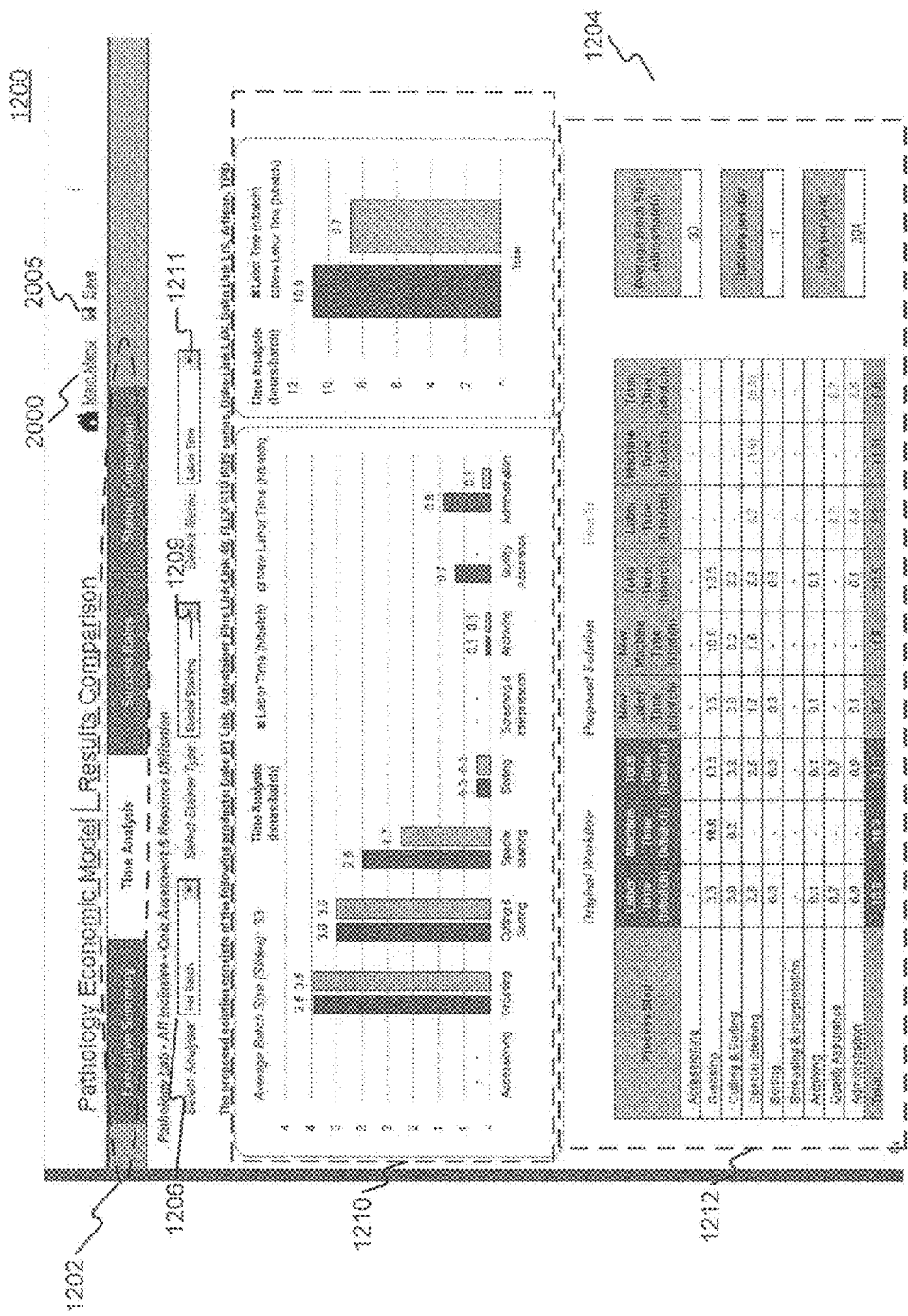
FIG. 12E is an exemplary representation of an interface providing a time analysis comparison between the performance evaluation of an existing workflow and a proposed workflow for the special staining process, based on labor time.
Figure 12F:
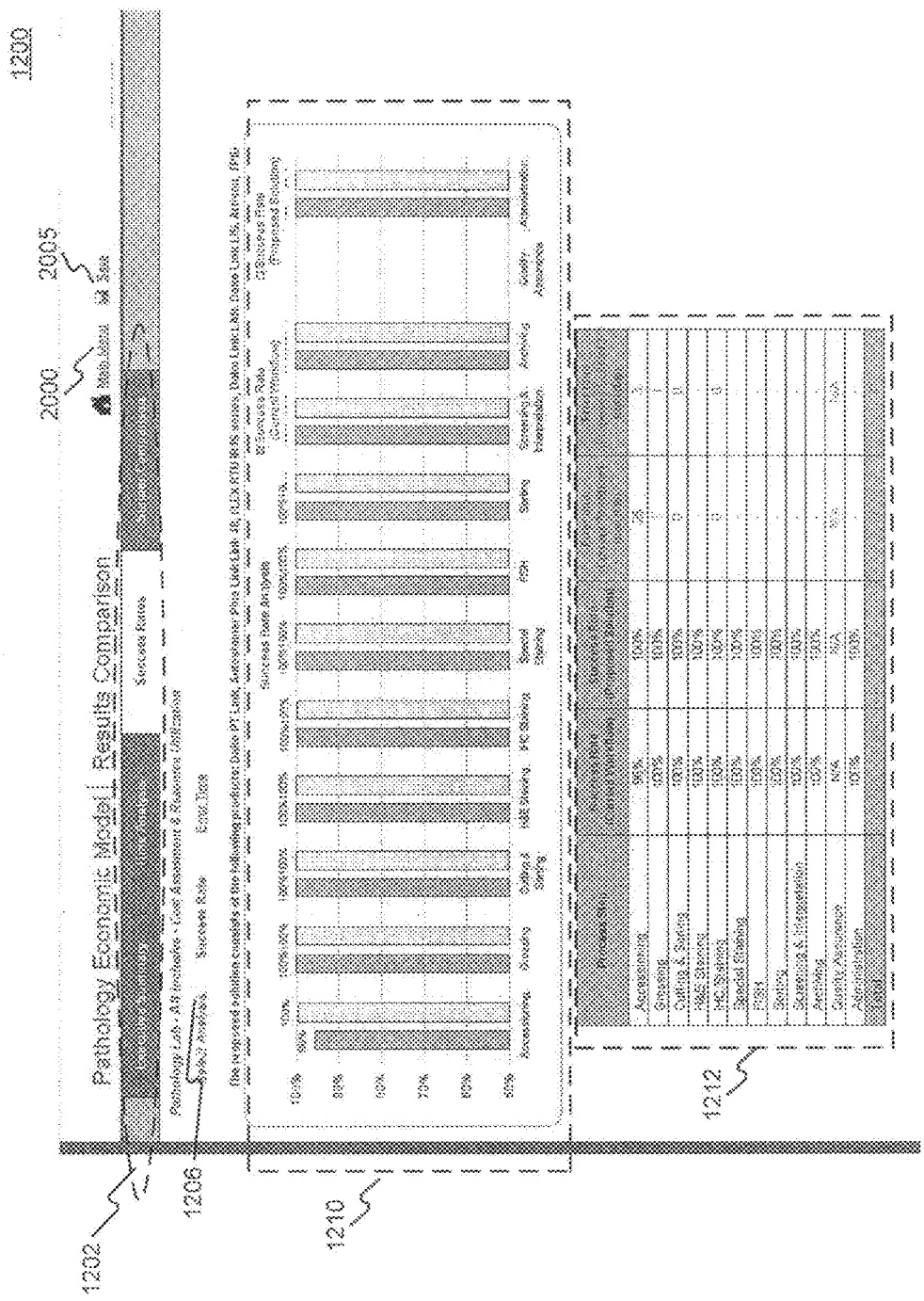
FIG. 12F is an exemplary representation of an interface providing a success rate analysis comparison between the performance evaluation of an existing workflow and a proposed workflow.
Figure 12G:
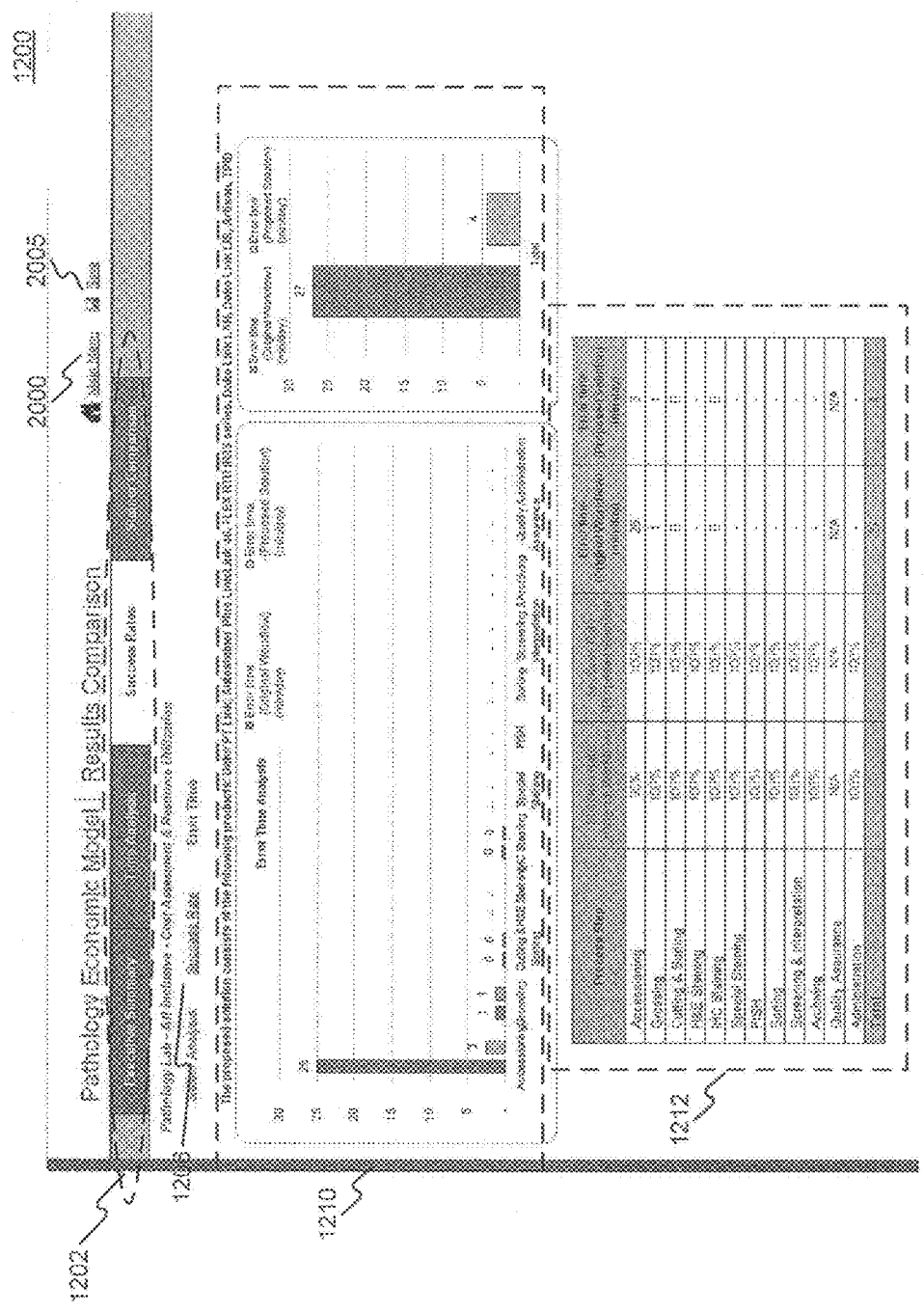
FIG. 12G is an exemplary representation of an interface providing a success rate analysis comparison between the performance evaluation of an existing workflow and a proposed workflow, based on error times.
Figure 12H:
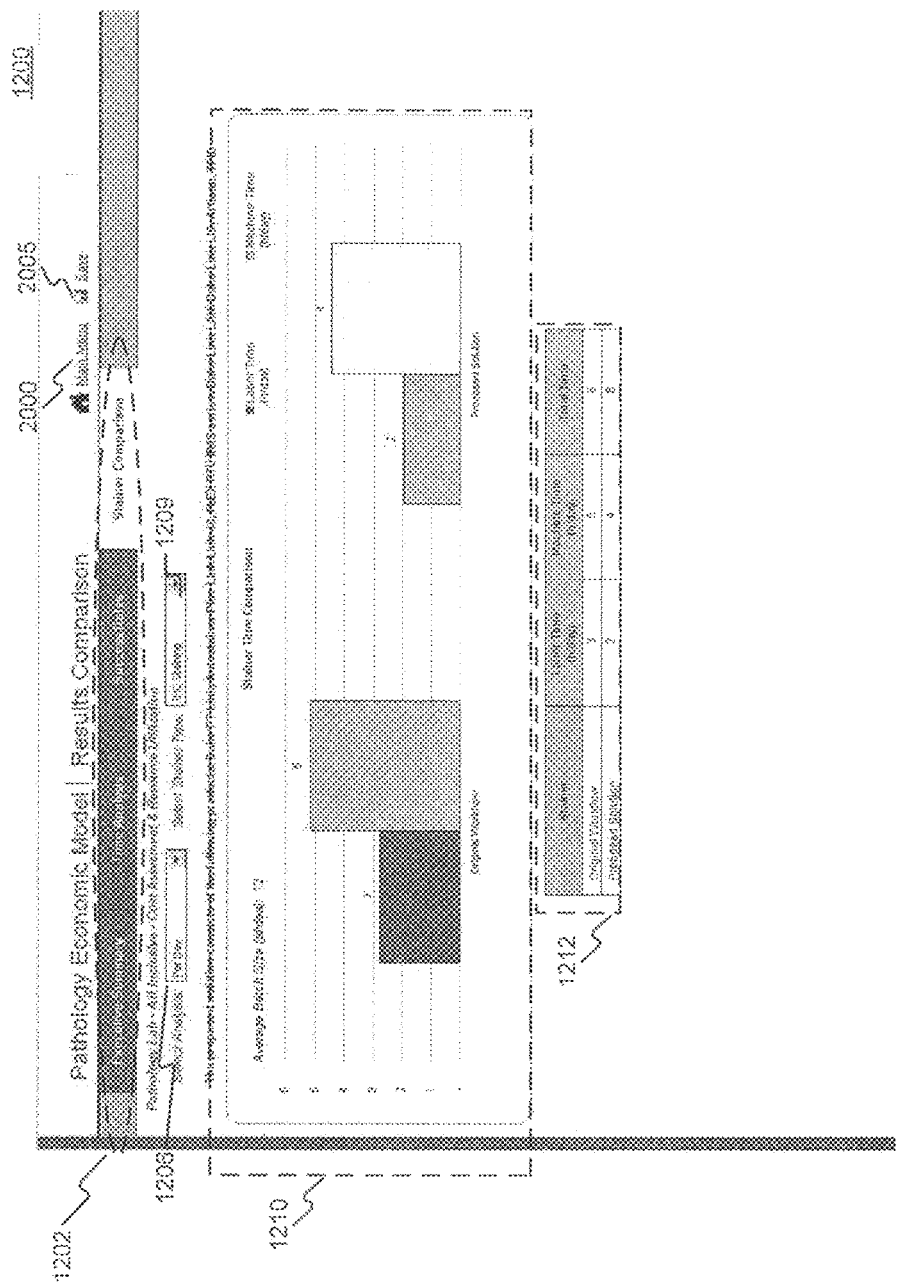
FIG. 12H is an exemplary representation of an interface providing a performance stainer comparison between an existing workflow and a proposed new stainer for the IHC staining process of an existing workflow.
Figure 12I:
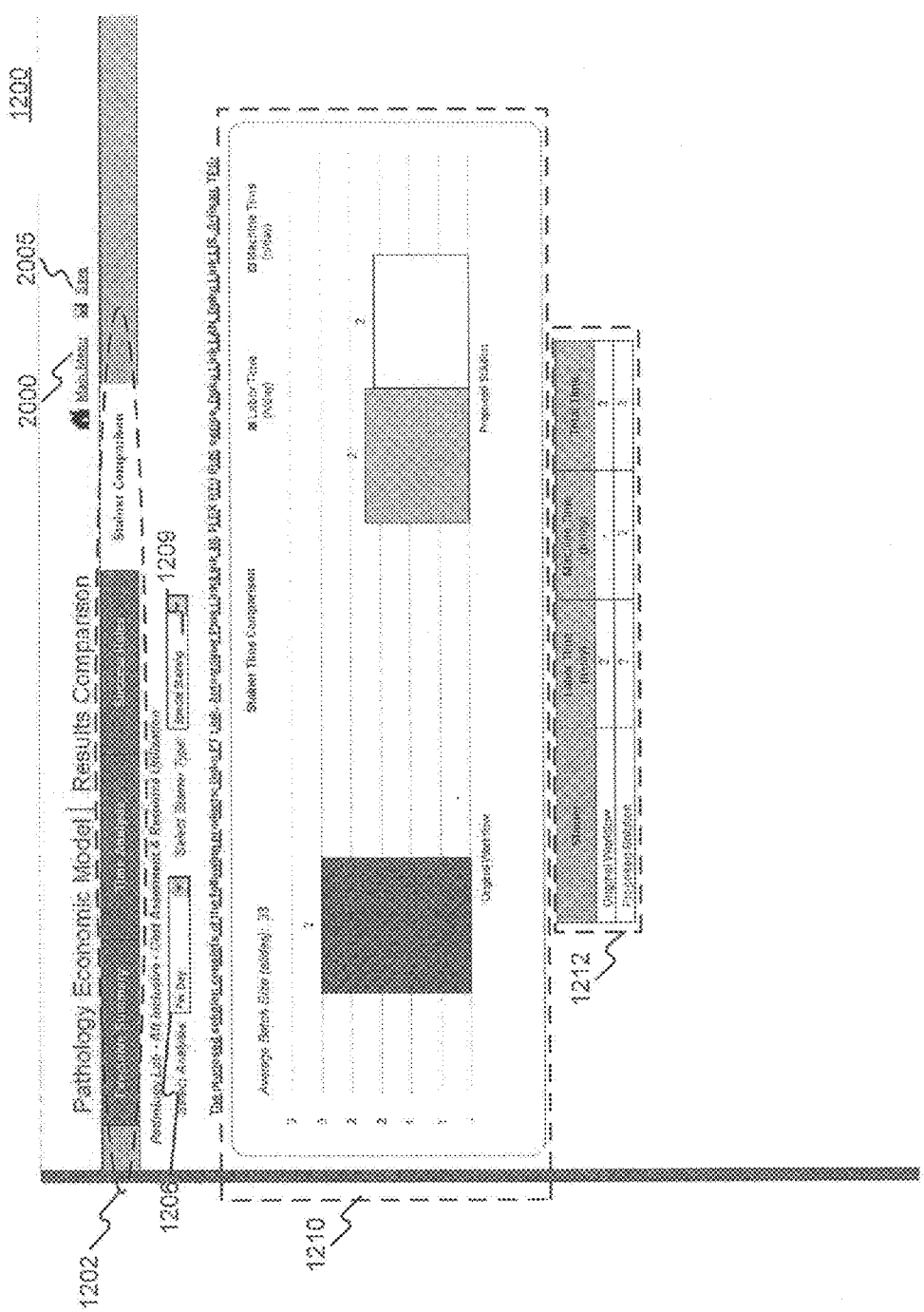
FIG. 12I is an exemplary representation of an interface providing a performance stainer comparison between an existing workflow and a proposed new stainer for the special staining process of an existing workflow.

For example, FIGS. 12B-12E show exemplary time analysis section of third interface 1200 with comparison results display area 1204 including several exemplary chart displays enabling display of comparison results based on selections at analysis selector 1206, stain selector 1209, and metric selector 1211. FIG. 12B is an exemplary representation of third interface 1200 providing a time analysis comparison between the performance evaluation of an existing workflow and a proposed workflow for the H&E staining process, based on labor time. FIG. 12C is an exemplary representation of third interface 1200 providing a time analysis comparison between the performance evaluation of an existing workflow and a proposed workflow for the IHC staining process based on labor time, while FIG. 12D is an exemplary representation of third interface 1200 providing a time analysis comparison between the performance evaluation of an existing workflow and a proposed workflow for the IHC staining process based on machine time. FIG. 12E is an exemplary representation of third interface 1200 providing a time analysis comparison between the performance evaluation of an existing workflow and a proposed workflow for the special staining process based on labor time.

FIGS. 12F-12I show various other output information related to a comparison of current performance data with forecasted performance data associated with a pathology lab. Such output information may be presented through comparison results display area 1204, chart displays 1210, and tabular display 1212, and customized with analysis selector 1206 and stain selector 1209. These output displays include success rate comparisons by success rate (FIG. 12F) and by error time (FIG. 12G), and stainer comparisons for IHC staining (FIG. 12H) and special staining (FIG. 12I) both on a per day basis. One of ordinary skill in the art will recognize that upon review of these figures, more or fewer views of results may be provided based on the desires of a user. Further, one of ordinary skill in the art will recognize that results of the performance calculations can be displayed in any other suitable format without departing from the scope of the present disclosure.

Other functionality related to the comparison results may also be provided. For example, in addition to viewing the comparison results from within analysis tool 300, analysis tool 300 may provide functionality through utility module 355 enabling a user to export the output to one or more formats, such as, for example, Microsoft PowerPoint, Microsoft Word, OpenOffice Impress, etc., among other things.

Figure 7:
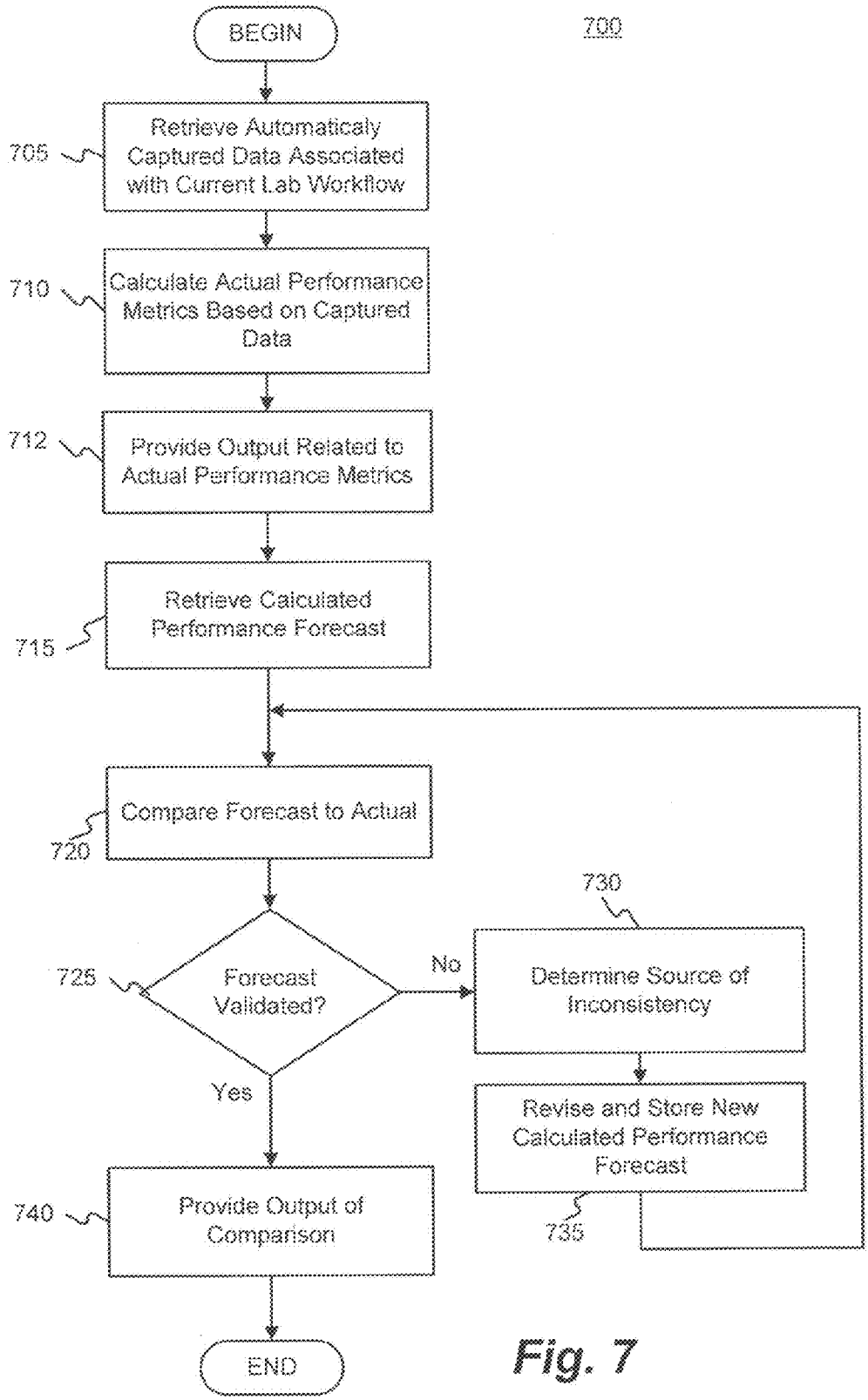
FIG. 7 is a block diagram showing an exemplary method for validating a forecasted workflow based on data obtained from laboratory equipment.

In some embodiments, analysis tool 300 may provide functionality related to validation of previous performance forecasts based on automatically stored data. FIG. 7 is a block diagram showing an exemplary method for validating a forecasted workflow based on data obtained from laboratory equipment, for example, via TPID module 362. As described above, laboratory devices present in a current or revised workflow may be configured to provide information related to their operation to workflow server 155 or other suitable device for storage. Such information may include station timestamp information (e.g., a specimen arrival timestamp and a specimen departure timestamp), machine time (e.g., the amount of time a device took to execute a process), and a number of output pieces from the station, among other things. This data may be automatically captured by TPID module 362 and/or workflow server 155 and stored in workflow database 160 and/or other suitable location.

The stored information may be retrieved from workflow database 160 for purposes of validating previously forecasted performance data and/or other purposes (step 705). For example, data module 330 may retrieve data related to the operation of the one or more laboratory devices over a particular time period, for example, a previous month. In such an example, the retrieved data may include the number of cases during the month, the number of specimen output pieces from H&E staining station 130 during the month, the number of specimen output pieces from IHC staining station 135 during the month, the number of specimen output pieces from special staining station 140, the number of specimen output pieces from ISH staining station 133 during the month, and a number of blocks processed during the month. In addition, machine times for each of the laboratory devices, timestamps related to specimens, operator IDs related to operators, and various other data may be retrieved.

Based on the retrieved data, analysis tool 300 may calculate, via PEM calculation module 320, or other suitable module, the actual performance data of the pathology laboratory for the month for which data was retrieved (step 710). The calculations may be similar to those discussed in relation to FIG. 5 above, resulting in data such as cost information including instrument costs, overhead costs, error costs, labor costs, consumables costs, waste costs, and service costs. Further, a success rate and error rate may also be calculated, among others. However, because data is actual stored data, averaging calculations may be used as actual labor times may be derived at each station by utilizing work hours associated with the lab, actual recorded machine times, and recorded timestamp data. For example, timestamp information may indicate that a specimen spent 3 hours in IHC staining station 135, with 2 hours of that time indicated by machine time. Therefore, a simple inference may be drawn that labor time within IHC staining was approximately 1 hour for set up and initiation of the IHC staining process. One of ordinary skill in the art will recognize that timestamp information may be compensated for work hours, for example, when a timestamp indicates a specimen arrived at a lab station 8:00 PM, and did not leave until 10:00 AM the following day, labor time may be compensated knowing that the lab closed at 8:30 PM the previous night and reopened at 7:00 AM. Further one of ordinary skill in the art will recognize that more or fewer data may be stored and analyzed based on the complexity of analysis tool 300 desired.

Once actual performance data has been calculated based on the captured data, output may be provided related to the current actual performance data (step 712). Presentation of the data may be provided similarly to the techniques described above with reference to step 415 and FIGS. 10A-10J. One of ordinary skill in the art will recognize that variations in labeling and presentation are intended to fall within the scope of the present disclosure.

Following a review of the actual performance data of the lab based on the actual stored data from one or more laboratory devices, a user may wish to compare the actual performance data with a performance forecast previously made using analysis tool 300 as described above with reference to steps 420 and 425 and FIGS. 11A-12I. In such a case, analysis tool 300 may retrieve the stored data related to the previously calculated performance forecast (step 715). Retrieved data may include revised cost information including a revised instrument cost, a revised overhead cost, a revised error cost, a revised labor cost, a revised consumables cost, a revised waste cost, and a revised service cost. Further, such data may include a revised success rate, a revised labor time, and a revised device time, among others.

Once the forecasted performance data has been retrieved, the data may be compared with the actual data calculated at step 710 (step 720). Such a comparison may be a direct comparison of like values between the actual values and the previously forecast values to determine a delta, if any, between the actual and forecast values. For example, an actual cost per specimen output piece (e.g., slide costs of $1.37) and an actual success rate (e.g., 99.92%) may be compared to a previously forecasted cost per specimen output piece and forecasted success rate, and deltas between the values determined. A predetermined margin value (e.g., 2 cents, 0.05%, etc.) may be stored with analysis tool for comparison with the deltas. If, for example, the delta between the actual cost per output piece and the forecasted cost per output piece is greater than the predetermined margin value, then the forecast may be considered not validated (step 725:no). Upon determining that the forecast has not been validated, analysis tool 300 may attempt to determine a source of the inconsistency (step 730). For example, analysis tool 300 may iteratively examine data points associated with the one or more proposed modifications to a workflow to determine where, based on the actual data retrieved from workflow database 160, the previous forecast was off. Once the source of the inconsistency has been identified, analysis tool 300 may revise the identified parameter and may store the identified information for future modification to analysis tool 300, the workflow, and/or parameters associated with the forecasted outlook. For example, if analysis tool 300 determines that a calculation error led to the inconsistency, analysis tool 300 may store the calculation error in workflow database 160 (step 735). In addition, analysis tool 300 may be enabled to report the error via network 101, and/or, for example, the internet. Analysis tool 300 may then repeat the comparison with corrected information to determine if future forecasts are more likely to be correct (return to step 720).

Where the comparison indicates that the forecast and the actual performance data are validated (step 725:yes), output of the comparison may be displayed via GUI module 305 similarly to that described above with reference to FIGS. 12A-12I (step 740). In such a case, the actual data may be substituted in place of the calculated current performance data of the pathology laboratory.

Figure 8:
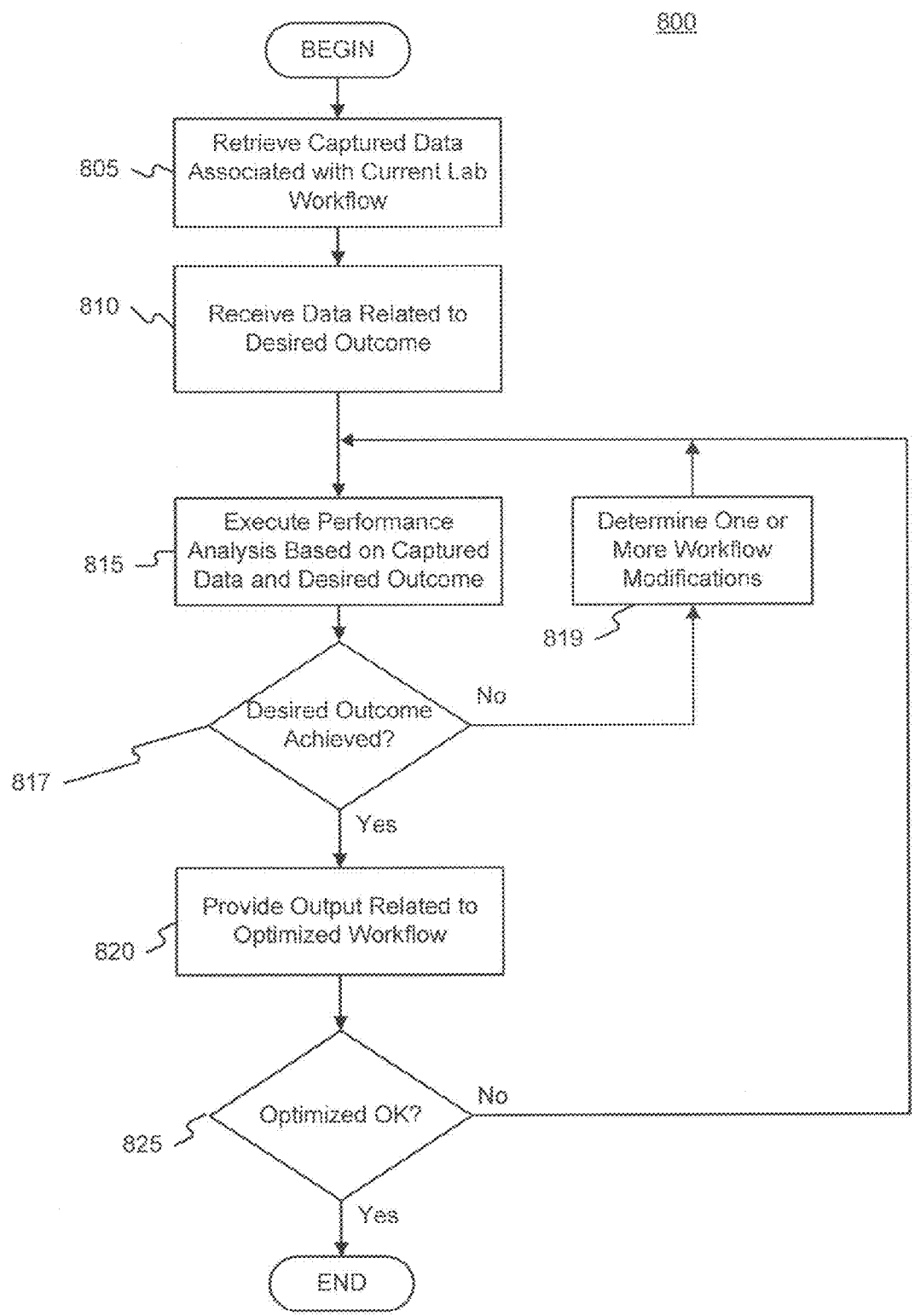
FIG. 8 is a block diagram showing an exemplary method for optimizing a laboratory workflow based on user desired outcome.

In some other embodiments, analysis tool 300 may enable optimization of a workflow based on current workflow data and one or more desires of a user (e.g., a lab manager). FIG. 8 is a block diagram showing an exemplary method for optimizing a laboratory workflow based on a user desired outcome (e.g., a specimen review schedule, a desired processing time, a desired specimen receipt time, a desired cost savings, a desired success rate, etc.). In such embodiments, actual data associated with a pathology lab may be retrieved, for example, from workflow server 155 and/or workflow database 160 (step 805). Such information may include station timestamp information (e.g., a specimen arrival timestamp and a specimen departure timestamp), machine time (e.g., the amount of time a device took to execute a process), and a number of output pieces from the station, among other things.

A user may then provide data related to a desired outcome in the pathology lab (step 810). For example, a user may desire that specimens be ready for review upon arrival of the pathologist at 3:00 PM. Therefore, the user may input such information into analysis tool 300. Some other examples of user desired outcomes may include a desire that total processing time for a specimen be less than 8 hours, a desire for a specific cost savings throughout the lab of $10,000, and/or a desired success rate of 99.97%. One of ordinary skill in the art will recognize that analysis tool 300 may be configured to receive any user desired outcome for purposes of attempting to meet that outcome.

After parameters related to a user outcome have been provided to analysis tool 300, analysis tool 300 may execute one or more performance analyses utilizing the actual data (step 815). Once a first performance analysis has been performed, analysis tool 300 may determine whether the user's desired outcome has been met by the existing workflow (step 817). For example, where a user desires an increased success rate of 99.97 percent, analysis tool 300 may determine that a current success rate of 99.8 percent is insufficient (step 817:no) and may then utilize logic to determine one or more proposed revisions to the current workflow to meet the user's desired outcome (step 819). For example, based on data stored within analysis tool 300 (e.g., product parameters), analysis tool 300 may determine that a success rate can be increased through implementation of an automated microtome at sectioning station 125 within the current workflow. Analysis tool 300 may then modify the workflow and run another performance analysis to determine if a forecast success rate meets the user's desired increase in success rate (step 815). If the automatically proposed modification to the workflow results in user's desired outcome being met (e.g., 99.97 percent success rate) (step 817:yes), then output related to the proposed modifications and the optimized workflow may be provided to the user (step 820). If the user's desired outcome has not been met by the automatically proposed modifications to the workflow (step 817:no), then analysis tool 300 may iteratively propose additional modifications until the user's desired outcome is met, or it is determined that the outcome cannot be achieved.

Upon review of the output related to the proposed workflow modifications and optimized workflow, a user may determine whether the proposed changes are acceptable (step 825). For example, if the addition of a microtome is proposed, but the user believes this proposal to be undesired (e.g., too expensive), the user may elect to run the optimization again (step 825:no). Otherwise, the user may print or otherwise export results (step 825:yes).

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

We claim:

1. An analysis tool for validating forecasted performance data associated with a pathology lab workflow, comprising:
    a display;
    a processor configured to:
    retrieve data reflecting a machine time, a number of specimen output pieces, and timestamp information associated with a laboratory device in a pathology lab;
    determine, based on the retrieved data, actual performance data selected from the group consisting of actual cost per specimen, actual success rate, actual processing time, actual receipt time, and actual review time associated with the pathology lab; and
    retrieve previously forecasted performance data selected from the group consisting of forecasted cost per specimen, forecasted success rate, forecasted processing time, forecasted receipt time, and forecasted review time for the pathology lab, wherein the previously forecasted performance data is computed based on proposed workflow modifications;
    validate the forecasted performance data against the actual performance data by comparing the forecasted performance data with the actual performance data; and
    provide an output of the validation to the display.

2. The analysis tool of claim 1, wherein the actual performance data comprises an actual cost per specimen output piece and an actual success rate.

3. The analysis tool of claim 2, wherein the forecasted performance data comprises a forecasted cost per specimen output piece and a forecasted success rate.

4. The analysis tool of claim 3, wherein the validating comprises:

determining a delta between the actual cost per specimen output piece and the forecasted cost per specimen output piece; and determining whether the delta falls below a predetermined threshold value.

5. The analysis tool of claim 4, further comprising:
identifying a source of the delta;
correcting the forecasted performance data based on the source; and
providing a representation of the corrected forecasted performance data to the display.

6. The analysis tool of claim 5, wherein the identified source is stored for future modification of at least one of the analysis tool, the workflow, or a parameter set associated with the forecasted outlook.

7. The analysis tool of claim 3, wherein the validating comprises:
determining a delta between the actual success rate and the forecasted success rate; and
determining whether the delta falls below a predetermined threshold value.

8. The analysis tool of claim 7, further comprising:
identifying a source of the delta;
correcting the forecasted performance data based on the source; and
providing a representation of the corrected forecasted performance data to the display.

9. The analysis tool of claim 8, wherein the identified source is stored for future modification of at least one of the analysis tool, the workflow, or a parameter set associated with the forecasted outlook.

10. The analysis tool of claim 2, wherein the specimen output piece comprises a specimen slide.

11. A computer implemented method for optimizing a pathology lab workflow based on one or more user parameters, comprising:
receiving one or more user parameters related to a desired outcome for a pathology lab wherein the user parameters include at least one of a desired processing time, a desired specimen receipt time, a desired cost savings, a desired review time, or a desired success rate;
retrieving captured data related to a current pathology lab workflow;
executing with a processor a performance analysis tool to determine a current performance based on the retrieved captured data;
executing with a processor a performance analysis tool to compare the one or more user parameters to the current performance;
determining a revision to the current pathology lab workflow based on the comparison between the one or more user parameters and the current performance, wherein the revised workflow reflects a laboratory device and achieves the desired outcome; and
providing on a display an output related to the revision.

12. The method of claim 11, wherein the captured data is automatically received from a laboratory device in the pathology lab.

13. The method of claim 11, wherein the laboratory device comprises at least one of an autostainer device, a microtome device, a specimen identifying device, a specimen marking device, an image sharing device, an image analysis device, a cover slipping device, a slide pretreatment device, a tissue processing device, or an information display device.

14. An analysis tool for validating forecasted performance data associated with a pathology lab workflow, comprising:
a display;
a processor configured to:
retrieve data reflecting a machine time, a number of specimen output pieces, and timestamp information associated with a laboratory device in a pathology lab;
determine, based on the retrieved data, actual performance data selected from the group consisting of actual cost information, actual error information, actual time utilization information, and actual device utilization information, associated with the pathology lab; and
retrieve previously forecasted performance data selected from the group consisting of forecasted cost information, forecasted error information, forecasted time utilization information, and forecasted device utilization information, for the pathology lab, wherein the previously forecasted performance data is computed based on proposed workflow modifications;
validate the forecasted performance data against the actual performance data by comparing the forecasted performance data with the actual performance data; and
provide an output of the validation to the display.

* * * * *